United States Patent
Bojarski et al.

(10) Patent No.: US 8,439,926 B2
(45) Date of Patent: May 14, 2013

(54) PATIENT SELECTABLE JOINT ARTHROPLASTY DEVICES AND SURGICAL TOOLS

(75) Inventors: Raymond Bojarski, Attleboro, MA (US); Wolfgang Fitz, Sherborn, MA (US); Philipp Lang, Lexington, MA (US)

(73) Assignee: ConforMIS, Inc., Bedford, MA (US)

( * ) Notice: Subject to any disclaimer, the term of this patent is extended or adjusted under 35 U.S.C. 154(b) by 778 days.

(21) Appl. No.: 12/398,753

(22) Filed: Mar. 5, 2009

(65) Prior Publication Data

US 2009/0222014 A1    Sep. 3, 2009

Related U.S. Application Data

(63) Continuation-in-part of application No. 11/671,745, filed on Feb. 6, 2007, and a continuation-in-part of application No. 11/002,573, filed on Dec. 2, 2004, now Pat. No. 7,534,263, which is a continuation-in-part of application No. 10/724,010, filed on Nov. 25, 2003, now Pat. No. 7,618,451, which is a continuation-in-part of application No. 10/305,652, filed on Nov. 27, 2002, now Pat. No. 7,468,075, which is a continuation-in-part of application No. 10/160,667, filed on May 28, 2002, said application No. 11/671,745 is a continuation-in-part of application No. 10/728,731, filed on Dec. 4, 2003, now Pat. No. 7,634,119, said application No. 11/671,745 is a continuation-in-part of application No. 10/681,750, filed on Oct. 7, 2003.

(60) Provisional application No. 61/052,430, filed on May 12, 2008, provisional application No. 61/034,048, filed on Mar. 5, 2008, provisional application No. 60/765,592, filed on Feb. 6, 2006, provisional application No. 60/785, 168, filed on Mar. 23, 2006, provisional application No. 60/788,339, filed on Mar. 31, 2006, provisional application No. 60/293,488, filed on May 25, 2001, provisional application No. 60/363,527, filed on Mar. 12, 2002, provisional application No. 60/380,692, filed on May 14, 2002, provisional application No. 60/380,695, filed on May 14, 2002, provisional application No. 60/431,176, filed on Dec. 4, 2002, provisional application No. 60/467,686, filed on May 2, 2003, provisional application No. 60/416,601, filed on Oct. 7, 2002.

(51) Int. Cl.
*A61B 17/58* (2006.01)

(52) U.S. Cl.
USPC .............................................. 606/88

(58) Field of Classification Search ............... 606/88, 606/87, 80, 76 R, 79, 86 R
See application file for complete search history.

(56) References Cited

U.S. PATENT DOCUMENTS 3,314,420 A    4/1967   Smith et al. ............... 128/92
(Continued)

FOREIGN PATENT DOCUMENTS

DE         2306552        8/1974
(Continued)

OTHER PUBLICATIONS

Andersson et al., "MacIntosh Arthroplasty in Rheumatoid Arthritis," Acta. Orthrop. Scand. 45(2):245-259 (1974).

(Continued)

*Primary Examiner* — Pedro Philogene
(74) *Attorney, Agent, or Firm* — Sunstein Kann Murphy & Timbers LLP

(57) ABSTRACT

Disclosed herein are tools for repairing articular surfaces repair materials and for repairing an articular surface. The surgical tools are designed to be customizable or highly selectable by patient to increase the speed, accuracy and simplicity of performing total or partial arthroplasty.

29 Claims, 40 Drawing Sheets

U.S. PATENT DOCUMENTS

| | | | |
|---|---|---|---|
| 3,605,123 A | 9/1971 | Hahn | 3/1 |
| 3,798,679 A | 3/1974 | Ewald | 3/1 |
| 3,808,606 A | 5/1974 | Tronzo | 3/1 |
| 3,843,975 A | 10/1974 | Tronzo | 3/1 |
| 3,855,638 A | 12/1974 | Pilliar | 3/1 |
| 3,938,198 A | 2/1976 | Kahn et al. | 3/1.912 |
| 3,987,499 A | 10/1976 | Scharbach et al. | 3/1.91 |
| 4,052,753 A | 10/1977 | Dedo | 3/1 |
| 4,055,862 A | 11/1977 | Farling | 3/1.91 |
| 4,085,466 A | 4/1978 | Goodfellow et al. | 3/1.91 |
| 4,098,626 A | 7/1978 | Graham et al. | 149/19.4 |
| 4,203,444 A | 5/1980 | Bonnell et al. | 128/276 |
| 4,213,816 A | 7/1980 | Morris | 156/245 |
| 4,340,978 A | 7/1982 | Buechel et al. | 3/1.911 |
| 4,368,040 A | 1/1983 | Weissman | 433/36 |
| 4,436,684 A | 3/1984 | White | 264/138 |
| 4,501,266 A | 2/1985 | McDaniel | 128/69 |
| 4,502,161 A | 3/1985 | Wall | 3/1.91 |
| 4,586,496 A | 5/1986 | Keller | 128/92 E |
| 4,594,380 A | 6/1986 | Chapin et al. | 524/144 |
| 4,601,290 A | 7/1986 | Effron et al. | 128/305 |
| 4,609,551 A | 9/1986 | Caplan et al. | 424/95 |
| 4,627,853 A | 12/1986 | Campbell et al. | 623/16 |
| 4,715,860 A | 12/1987 | Amstutz et al. | 623/22 |
| 4,721,104 A | 1/1988 | Kaufman et al. | 128/92 |
| 4,759,350 A | 7/1988 | Dunn et al. | 128/92 VW |
| 4,769,040 A | 9/1988 | Wevers | 623/20 |
| 4,841,975 A | 6/1989 | Woolson | 128/653 |
| 4,846,835 A | 7/1989 | Grande | 623/11 |
| 4,865,607 A | 9/1989 | Witzel et al. | 623/20 |
| 4,880,429 A | 11/1989 | Stone | 623/18 |
| 4,936,862 A | 6/1990 | Walker et al. | 623/23 |
| 4,979,949 A | 12/1990 | Matsen, III et al. | 606/53 |
| 5,002,547 A | 3/1991 | Poggie et al. | 606/88 |
| 5,041,138 A | 8/1991 | Vacanti et al. | 623/16 |
| 5,053,039 A | 10/1991 | Hofmann et al. | 606/87 |
| 5,059,216 A | 10/1991 | Winters | 623/20 |
| 5,067,964 A | 11/1991 | Richmond et al. | 623/18 |
| 5,122,144 A | 6/1992 | Bert et al. | 606/88 |
| 5,129,908 A | 7/1992 | Petersen | 606/88 |
| 5,133,759 A | 7/1992 | Turner | 623/20 |
| 5,154,717 A | 10/1992 | Matsen, III et al. | 606/53 |
| 5,162,430 A | 11/1992 | Rhee et al. | 525/54.1 |
| 5,171,322 A | 12/1992 | Kenny | 623/18 |
| 5,197,985 A | 3/1993 | Caplan et al. | 623/16 |
| 5,206,023 A | 4/1993 | Hunziker | 424/423 |
| 5,226,914 A | 7/1993 | Caplan et al. | 623/16 |
| 5,234,433 A | 8/1993 | Bert et al. | 606/88 |
| 5,250,050 A | 10/1993 | Poggie et al. | 606/79 |
| 5,258,032 A | 11/1993 | Bertin | 623/20 |
| 5,270,300 A | 12/1993 | Hunziker | 514/12 |
| 5,288,797 A | 2/1994 | Khalil et al. | 524/872 |
| 5,303,148 A | 4/1994 | Mattson et al. | 364/413.01 |
| 5,306,311 A | 4/1994 | Stone et al. | 623/18 |
| 5,314,482 A | 5/1994 | Goodfellow et al. | 623/20 |
| 5,344,459 A | 9/1994 | Swartz | 623/18 |
| 5,360,446 A | 11/1994 | Kennedy | 623/16 |
| 5,368,858 A | 11/1994 | Hunziker | 424/423 |
| 5,380,332 A | 1/1995 | Ferrante | 606/79 |
| 5,387,216 A | 2/1995 | Thornhill et al. | 606/88 |
| 5,437,676 A | 8/1995 | Bouraly et al. | 606/88 |
| 5,468,787 A | 11/1995 | Braden et al. | 523/113 |
| 5,474,559 A | 12/1995 | Bertin et al. | 606/89 |
| 5,478,739 A | 12/1995 | Slivka et al. | 435/240.23 |
| 5,486,180 A | 1/1996 | Dietz et al. | 606/87 |
| 5,501,687 A | 3/1996 | Willert et al. | 606/94 |
| 5,503,162 A | 4/1996 | Athanasiou et al. | 128/774 |
| 5,523,843 A | 6/1996 | Yamane et al. | 356/363 |
| 5,540,696 A | 7/1996 | Booth, Jr. et al. | 606/88 |
| 5,542,947 A | 8/1996 | Treacy | 606/88 |
| 5,554,190 A | 9/1996 | Draenert | 623/16 |
| 5,556,432 A | 9/1996 | Kubein-Meesenburg et al. | 623/20 |
| 5,571,205 A | 11/1996 | James | 623/24 |
| 5,575,793 A | 11/1996 | Carls et al. | 606/80 |
| 5,578,037 A | 11/1996 | Sanders et al. | 606/80 |
| 5,593,450 A | 1/1997 | Scott et al. | 623/20 |
| 5,597,379 A | 1/1997 | Haines et al. | 606/80 |
| 5,601,563 A | 2/1997 | Burke et al. | 606/86 |
| 5,613,970 A | 3/1997 | Houston et al. | 606/88 |
| 5,616,146 A | 4/1997 | Murray | 606/80 |
| 5,630,820 A | 5/1997 | Todd | 606/90 |
| 5,632,745 A | 5/1997 | Schwartz | 606/75 |
| 5,649,929 A | 7/1997 | Callaway | 606/88 |
| 5,658,290 A | 8/1997 | Techeira | 606/80 |
| 5,671,741 A | 9/1997 | Lang et al. | 128/653.2 |
| 5,681,316 A | 10/1997 | DeOrio et al. | 606/88 |
| 5,682,886 A | 11/1997 | Delp et al. | 128/653.1 |
| 5,683,466 A | 11/1997 | Vitale | 623/18 |
| 5,684,562 A | 11/1997 | Fujieda | 351/212 |
| 5,688,282 A | 11/1997 | Baron et al. | 606/90 |
| 5,728,162 A | 3/1998 | Eckhoff | 623/20 |
| 5,735,277 A | 4/1998 | Schuster | 128/653.1 |
| 5,749,874 A | 5/1998 | Schwartz | 606/75 |
| 5,749,876 A | 5/1998 | Duvillier | 606/88 |
| 5,768,134 A | 6/1998 | Swaelens et al. | 364/468.28 |
| 5,769,899 A | 6/1998 | Schwartz et al. | 623/18 |
| 5,776,137 A | 7/1998 | Katz | 606/88 |
| 5,786,217 A | 7/1998 | Tubo et al. | 435/402 |
| 5,800,438 A | 9/1998 | Tuke et al. | 606/90 |
| 5,827,289 A | 10/1998 | Reiley et al. | 606/86 |
| 5,830,216 A | 11/1998 | Insall et al. | 606/88 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,860,981 A | 1/1999 | Bertin et al. | 606/89 |
| 5,871,018 A | 2/1999 | Delp et al. | 128/898 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia, III et al. | 364/578 |
| 5,885,296 A | 3/1999 | Masini | 606/86 |
| 5,885,297 A | 3/1999 | Matsen, III | 606/87 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,934 A | 5/1999 | Grande et al. | 435/325 |
| 5,911,723 A | 6/1999 | Ashby et al. | 606/88 |
| 5,916,220 A | 6/1999 | Masini | 606/88 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,972,385 A | 10/1999 | Liu et al. | 424/486 |
| 5,995,738 A | 11/1999 | DiGioia, III et al. | 395/500.32 |
| 6,001,895 A | 12/1999 | Harvey et al. | 523/113 |
| 6,002,859 A | 12/1999 | DiGioia, III et al. | 395/500.32 |
| 6,007,537 A | 12/1999 | Burkinshaw et al. | 606/66 |
| 6,010,509 A | 1/2000 | Delgado et al. | 606/88 |
| 6,013,103 A | 1/2000 | Kaufman et al. | 623/20 |
| 6,046,379 A | 4/2000 | Stone et al. | 623/11 |
| 6,056,754 A | 5/2000 | Haines et al. | 606/80 |
| 6,056,756 A | 5/2000 | Eng et al. | 606/87 |
| 6,057,927 A | 5/2000 | Lévesque et al. | 356/432 T |
| 6,077,270 A | 6/2000 | Katz | 606/88 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,096,043 A | 8/2000 | Techiera et al. | 606/88 |
| 6,102,916 A | 8/2000 | Masini | 606/88 |
| 6,106,529 A | 8/2000 | Techiera | 606/88 |
| 6,110,209 A | 8/2000 | Stone | 623/16.11 |
| 6,120,541 A | 9/2000 | Johnson | 623/14.12 |
| 6,126,690 A | 10/2000 | Ateshian et al. | 623/18 |
| 6,139,578 A | 10/2000 | Lee et al. | 623/16.11 |
| 6,156,069 A | 12/2000 | Amstutz | 623/22.11 |
| 6,161,080 A | 12/2000 | Aouni-Ateshian | 703/11 |
| 6,187,010 B1 | 2/2001 | Masini | 606/86 |
| 6,200,606 B1 | 3/2001 | Peterson et al. | 424/574 |
| 6,203,546 B1 | 3/2001 | MacMahon | 606/87 |
| 6,203,576 B1 | 3/2001 | Afriat et al. | 623/20.27 |
| 6,205,411 B1 | 3/2001 | DiGioia, III et al. | 703/11 |
| 6,206,927 B1 | 3/2001 | Fell et al. | 623/20.29 |
| 6,214,369 B1 | 4/2001 | Grande et al. | 424/423 |

| | | | | | |
|---|---|---|---|---|---|
| 6,217,894 B1 | 4/2001 | Sawhney et al. ............. 424/426 | 8,122,582 B2 | 2/2012 | Burdulis, Jr. et al. ........ 29/527.1 |
| 6,219,571 B1 | 4/2001 | Hargreaves et al. .......... 600/410 | RE43,282 E | 3/2012 | Alexander et al. ............ 600/427 |
| 6,224,632 B1 | 5/2001 | Pappas et al. ............. 623/20.34 | 2001/0001120 A1 | 5/2001 | Masini ............................ 606/86 |
| 6,235,060 B1 | 5/2001 | Kubein-Meesenburg et al. ............................ 623/20.31 | 2001/0010023 A1 | 7/2001 | Schwartz et al. .......... 623/23.72 |
| | | | 2001/0039455 A1 | 11/2001 | Simon et al. ................ 623/23.51 |
| 6,251,143 B1 | 6/2001 | Schwartz et al. .......... 623/23.72 | 2002/0013626 A1 | 1/2002 | Geistlich et al. ........... 623/23.57 |
| 6,277,151 B1 | 8/2001 | Lee et al. ..................... 623/23.61 | 2002/0029038 A1 | 3/2002 | Haines ........................... 606/54 |
| 6,281,195 B1 | 8/2001 | Rueger et al. ..................... 514/21 | 2002/0045940 A1 | 4/2002 | Giannetti et al. ........... 623/11.11 |
| 6,283,980 B1 | 9/2001 | Vibe-Hansen et al. ........ 606/151 | 2002/0059049 A1 | 5/2002 | Bradbury et al. ............... 703/11 |
| 6,296,646 B1 | 10/2001 | Williamson ..................... 606/90 | 2002/0068979 A1 | 6/2002 | Brown et al. ................. 623/20.3 |
| 6,299,905 B1 | 10/2001 | Peterson et al. .............. 424/486 | 2002/0072821 A1 | 6/2002 | Baker ............................ 700/98 |
| 6,322,588 B1 | 11/2001 | Ogle et al. ..................... 623/1.46 | 2002/0079601 A1 | 6/2002 | Russell et al. .............. 264/40.1 |
| 6,328,765 B1 | 12/2001 | Hardwick et al. ............ 623/23.72 | 2002/0082703 A1 | 6/2002 | Repicci ...................... 623/20.29 |
| 6,344,043 B1 | 2/2002 | Pappas ........................... 606/96 | 2002/0087274 A1 | 7/2002 | Alexander et al. .............. 702/19 |
| 6,344,059 B1 | 2/2002 | Krakovits et al. .......... 623/20.31 | 2002/0106625 A1 | 8/2002 | Hung et al. .................... 435/1.1 |
| 6,352,558 B1 | 3/2002 | Spector ....................... 623/18.11 | 2002/0115647 A1 | 8/2002 | Halvorsen et al. ............ 514/171 |
| 6,358,253 B1 | 3/2002 | Torrie et al. ..................... 606/96 | 2002/0120274 A1 | 8/2002 | Overaker et al. ............... 606/72 |
| 6,365,405 B1 | 4/2002 | Salzmann et al. ............. 435/366 | 2002/0120281 A1 | 8/2002 | Overaker ...................... 606/151 |
| 6,371,958 B1 | 4/2002 | Overaker ........................ 606/72 | 2002/0127264 A1 | 9/2002 | Felt et al. ...................... 424/423 |
| 6,373,250 B1 | 4/2002 | Tsoref et al. ................... 324/309 | 2002/0133230 A1 | 9/2002 | Repicci ....................... 623/14.12 |
| 6,375,658 B1 | 4/2002 | Hangody et al. ............... 606/80 | 2002/0143402 A1 | 10/2002 | Steinberg ................... 623/22.16 |
| 6,379,367 B1 | 4/2002 | Vibe-Hansen et al. ........ 606/151 | 2002/0151986 A1 | 10/2002 | Asculai et al. ................ 424/484 |
| 6,382,028 B1 | 5/2002 | Wooh et al. ....................... 73/602 | 2002/0156150 A1 | 10/2002 | Asculai et al. ............. 623/23.75 |
| 6,383,228 B1 | 5/2002 | Schmotzer ................. 623/23.35 | 2002/0173852 A1 | 11/2002 | Felt et al. .................... 623/20.32 |
| 6,387,131 B1 | 5/2002 | Miehlke et al. ............. 623/20.15 | 2002/0183850 A1 | 12/2002 | Felt et al. .................... 623/20.16 |
| 6,429,013 B1 | 8/2002 | Halvorsen et al. ............. 435/377 | 2003/0028196 A1 | 2/2003 | Bonutti ........................... 606/87 |
| 6,443,988 B2 | 9/2002 | Felt et al. ...................... 623/17.12 | 2003/0055500 A1 | 3/2003 | Fell et al. .................... 623/14.12 |
| 6,443,991 B1 | 9/2002 | Running ...................... 623/20.27 | 2003/0055501 A1 | 3/2003 | Fell et al. .................... 623/14.12 |
| 6,444,222 B1 | 9/2002 | Asculai et al. ................ 424/484 | 2003/0055502 A1 | 3/2003 | Lang et al. .................. 623/16.11 |
| 6,459,948 B1 | 10/2002 | Ateshian et al. ............... 700/117 | 2003/0060882 A1 | 3/2003 | Fell et al. .................... 623/14.12 |
| 6,468,314 B2 | 10/2002 | Schwartz et al. .......... 623/23.72 | 2003/0060883 A1 | 3/2003 | Fell et al. .................... 623/14.12 |
| 6,478,799 B1 | 11/2002 | Williamson ..................... 606/90 | 2003/0060884 A1 | 3/2003 | Fell et al. .................... 623/14.12 |
| 6,479,996 B1 | 11/2002 | Hoogeveen et al. ........... 324/309 | 2003/0060885 A1 | 3/2003 | Fell et al. .................... 623/14.12 |
| 6,510,334 B1 | 1/2003 | Schuster et al. ............... 600/407 | 2003/0100907 A1 | 5/2003 | Rosa et al. ..................... 606/86 |
| 6,520,964 B2 | 2/2003 | Tallarida et al. ............... 396/567 | 2003/0100953 A1 | 5/2003 | Rosa et al. ................... 623/20.3 |
| 6,558,421 B1 | 5/2003 | Fell et al. ...................... 623/14.12 | 2003/0120347 A1 | 6/2003 | Steinberg ................... 623/22.17 |
| 6,560,476 B1 | 5/2003 | Pelletier et al. ................ 600/410 | 2003/0158558 A1 | 8/2003 | Horn .............................. 606/87 |
| 6,575,980 B1 | 6/2003 | Robie et al. ..................... 606/88 | 2003/0158606 A1 | 8/2003 | Coon et al. ................. 623/20.15 |
| 6,575,986 B2 | 6/2003 | Overaker ........................ 606/151 | 2003/0163137 A1 | 8/2003 | Smucker et al. ............... 606/87 |
| 6,620,168 B1 | 9/2003 | Lombardo et al. .............. 606/88 | 2003/0173695 A1 | 9/2003 | Monkhouse et al. ......... 264/40.1 |
| 6,626,945 B2 | 9/2003 | Simon et al. ................ 623/17.19 | 2003/0216669 A1 | 11/2003 | Lang et al. ..................... 600/587 |
| 6,626,948 B2 | 9/2003 | Storer et al. ................ 623/23.14 | 2003/0225457 A1 | 12/2003 | Justin et al. ................ 623/20.14 |
| 6,632,225 B2 | 10/2003 | Sanford et al. ................. 606/87 | 2003/0236521 A1 | 12/2003 | Brown et al. ................... 606/80 |
| 6,632,235 B2 | 10/2003 | Weikel et al. .................. 606/192 | 2004/0098133 A1 | 5/2004 | Carignan et al. ........... 623/20.35 |
| 6,652,587 B2 | 11/2003 | Felt et al. .................... 623/20.16 | 2004/0102852 A1 | 5/2004 | Johnson et al. ............ 623/20.15 |
| 6,673,077 B1 | 1/2004 | Katz ................................ 606/88 | 2004/0122521 A1 | 6/2004 | Lee et al. .................... 623/20.15 |
| 6,679,917 B2 | 1/2004 | Ek ............................... 623/20.14 | 2004/0133276 A1 | 7/2004 | Lang et al. .................. 623/14.12 |
| 6,712,856 B1 | 3/2004 | Carignan et al. ........... 623/20.35 | 2004/0138754 A1 | 7/2004 | Lang et al. .................. 623/20.14 |
| 6,905,514 B2 | 6/2005 | Carignan et al. ........... 623/20.35 | 2004/0147927 A1 | 7/2004 | Tsougarakis et al. ........... 606/53 |
| 6,916,341 B2 | 7/2005 | Rolston ........................ 623/20.3 | 2004/0153079 A1 | 8/2004 | Tsougarakis et al. ........... 606/77 |
| 6,928,742 B2 | 8/2005 | Broers et al. .................... 33/512 | 2004/0153162 A1 | 8/2004 | Sanford et al. ............... 623/20.3 |
| 6,969,393 B2 * | 11/2005 | Pinczewski et al. ............. 606/88 | 2004/0153164 A1 | 8/2004 | Sanford et al. ............ 623/20.29 |
| 7,008,430 B2 | 3/2006 | Dong et al. ...................... 606/80 | 2004/0167390 A1 | 8/2004 | Alexander et al. ............ 600/410 |
| 7,060,074 B2 | 6/2006 | Rosa et al. ..................... 606/88 | 2004/0167630 A1 | 8/2004 | Rolston ...................... 623/20.14 |
| 7,104,997 B2 | 9/2006 | Lionberger et al. .............. 606/88 | 2004/0193280 A1 | 9/2004 | Webster et al. ............. 623/20.33 |
| 7,115,131 B2 | 10/2006 | Engh et al. ....................... 606/79 | 2004/0204644 A1 | 10/2004 | Tsougarakis et al. ......... 600/410 |
| 7,117,027 B2 | 10/2006 | Zheng et al. .................... 600/426 | 2004/0204760 A1 | 10/2004 | Fitz et al. .................... 623/14.12 |
| 7,141,053 B2 | 11/2006 | Rosa et al. ..................... 606/86 | 2004/0236424 A1 | 11/2004 | Fitz et al. .................... 623/14.12 |
| 7,184,814 B2 | 2/2007 | Lang et al. ...................... 600/416 | 2004/0249386 A1 | 12/2004 | Faoro ............................. 606/88 |
| 7,239,908 B1 | 7/2007 | Alexander et al. ............ 600/427 | 2005/0015153 A1 | 1/2005 | Goble et al. ................ 623/23.46 |
| 7,245,697 B2 | 7/2007 | Lang ................................. 378/54 | 2005/0021039 A1 | 1/2005 | Cusick et al. ................... 606/88 |
| 7,282,054 B2 | 10/2007 | Steffensmeier et al. ......... 606/96 | 2005/0043807 A1 | 2/2005 | Wood ......................... 623/20.14 |
| 7,292,674 B2 | 11/2007 | Lang ................................. 378/54 | 2005/0055028 A1 | 3/2005 | Haines ............................ 606/79 |
| 7,379,529 B2 | 5/2008 | Lang ................................. 378/54 | 2005/0085920 A1 | 4/2005 | Williamson ................. 623/20.14 |
| 7,467,892 B2 | 12/2008 | Lang et al. ....................... 378/207 | 2005/0107883 A1 | 5/2005 | Goodfried et al. .......... 623/20.15 |
| 7,468,075 B2 | 12/2008 | Lang et al. .................. 623/16.11 | 2005/0107884 A1 | 5/2005 | Johnson et al. ............ 623/20.15 |
| 7,534,263 B2 | 5/2009 | Burdulis, Jr. et al. ....... 623/14.12 | 2005/0119664 A1 | 6/2005 | Carignan et al. ............... 606/96 |
| 7,618,451 B2 | 11/2009 | Berez et al. .................. 623/14.12 | 2005/0143745 A1 | 6/2005 | Hodorek et al. ................ 606/87 |
| 7,747,305 B2 | 6/2010 | Dean et al. ...................... 600/407 | 2005/0148843 A1 | 7/2005 | Roose ............................ 600/407 |
| 7,806,896 B1 | 10/2010 | Bonutti ........................ 606/86 R | 2005/0171545 A1 | 8/2005 | Walsh et al. ..................... 606/72 |
| 7,881,768 B2 | 2/2011 | Lang et al. ....................... 600/407 | 2005/0171612 A1 | 8/2005 | Rolston ...................... 623/20.19 |
| 7,981,158 B2 | 7/2011 | Fitz et al. ......................... 128/92 | 2005/0192588 A1 | 9/2005 | Garcia ............................ 606/88 |
| 7,983,777 B2 | 7/2011 | Melton et al. ..................... 700/98 | 2005/0216305 A1 | 9/2005 | Funderud ........................ 705/2 |
| 8,036,729 B2 | 10/2011 | Lang et al. ....................... 600/407 | 2005/0234461 A1 | 10/2005 | Burdulis et al. ................ 606/79 |
| 8,062,302 B2 | 11/2011 | Lang et al. ....................... 606/87 | 2005/0267584 A1 | 12/2005 | Burdulis et al. ............ 623/20.19 |
| 8,066,708 B2 | 11/2011 | Lang et al. ....................... 606/88 | 2006/0052795 A1 | 3/2006 | White ............................ 606/102 |
| 8,083,745 B2 | 12/2011 | Lang et al. ....................... 606/87 | 2006/0111722 A1 | 5/2006 | Bouadi ............................ 606/79 |
| 8,105,330 B2 | 1/2012 | Fitz et al. .......................... 606/88 | 2006/0149283 A1 | 7/2006 | May et al. ....................... 606/96 |
| 8,112,142 B2 | 2/2012 | Alexander et al. ............ 600/407 | 2006/0200162 A1 | 9/2006 | Farling et al. ................... 606/88 |

| Publication No. | Date | Inventor | Class |
|---|---|---|---|
| 2006/0235421 A1 | 10/2006 | Rosa et al. | 606/88 |
| 2007/0015995 A1 | 1/2007 | Lang | 600/407 |
| 2007/0073305 A1 | 3/2007 | Lionberger et al. | 606/87 |
| 2007/0118141 A1 | 5/2007 | Marchyn et al. | 606/88 |
| 2007/0198022 A1 | 8/2007 | Lang et al. | 606/88 |
| 2007/0203430 A1 | 8/2007 | Lang et al. | 600/587 |
| 2007/0233151 A1 | 10/2007 | Chudik | 606/96 |
| 2007/0233156 A1 | 10/2007 | Metzger | 606/130 |
| 2007/0276224 A1 | 11/2007 | Lang et al. | 600/410 |
| 2007/0293868 A1 | 12/2007 | Delfosse et al. | 606/88 |
| 2008/0004709 A1 | 1/2008 | O'Neill et al. | 623/20.35 |
| 2008/0015433 A1 | 1/2008 | Alexander et al. | 600/427 |
| 2008/0025463 A1 | 1/2008 | Lang | 378/54 |
| 2008/0031412 A1 | 2/2008 | Lang et al. | 378/54 |
| 2008/0058613 A1 | 3/2008 | Lang et al. | 600/300 |
| 2008/0058945 A1 | 3/2008 | Hajaj et al. | 623/20.14 |
| 2008/0097794 A1 | 4/2008 | Arnaud et al. | 705/3 |
| 2008/0114370 A1 | 5/2008 | Schoenefeld | 606/96 |
| 2008/0170659 A1 | 7/2008 | Lang et al. | 378/56 |
| 2008/0195216 A1 | 8/2008 | Lang | 623/18.11 |
| 2008/0219412 A1 | 9/2008 | Lang | 378/207 |
| 2008/0243127 A1 | 10/2008 | Lang et al. | 606/87 |
| 2008/0275452 A1 | 11/2008 | Lang et al. | 606/88 |
| 2008/0281328 A1 | 11/2008 | Lang et al. | 606/87 |
| 2008/0281329 A1 | 11/2008 | Fitz et al. | 623/17.16 |
| 2008/0281426 A1 | 11/2008 | Fitz et al. | 623/17.16 |
| 2009/0076371 A1 | 3/2009 | Lang et al. | 600/407 |
| 2009/0087276 A1* | 4/2009 | Rose | 409/79 |
| 2009/0088753 A1* | 4/2009 | Aram et al. | 606/79 |
| 2009/0088758 A1* | 4/2009 | Bennett | 606/82 |
| 2009/0099567 A1 | 4/2009 | Zajac | 606/79 |
| 2009/0131941 A1 | 5/2009 | Park et al. | 606/87 |
| 2009/0131942 A1 | 5/2009 | Aker et al. | 606/88 |
| 2009/0222014 A1 | 9/2009 | Bojarski et al. | 606/88 |
| 2009/0307893 A1 | 12/2009 | Burdulis, Jr. et al. | 29/527.1 |
| 2010/0160917 A1 | 6/2010 | Fitz et al. | 606/88 |
| 2010/0168754 A1 | 7/2010 | Fitz et al. | 606/88 |
| 2010/0281678 A1 | 11/2010 | Burdulis, Jr. et al. | 29/592 |
| 2010/0298894 A1 | 11/2010 | Bojarski et al. | 606/86 R |
| 2010/0305573 A1 | 12/2010 | Fitz et al. | 606/87 |
| 2010/0305574 A1 | 12/2010 | Fitz et al. | 606/88 |
| 2011/0066193 A1 | 3/2011 | Lang et al. | 606/86 R |
| 2011/0071581 A1 | 3/2011 | Lang et al. | 606/86 R |
| 2011/0213368 A1 | 9/2011 | Fitz et al. | 606/80 |
| 2011/0213373 A1 | 9/2011 | Fitz et al. | 606/87 |
| 2011/0213374 A1 | 9/2011 | Fitz et al. | 606/87 |
| 2011/0213377 A1 | 9/2011 | Lang et al. | 606/89 |
| 2011/0213427 A1 | 9/2011 | Fitz et al. | 606/86 R |
| 2011/0213428 A1 | 9/2011 | Fitz et al. | 606/86 R |
| 2011/0213429 A1 | 9/2011 | Lang et al. | 606/86 R |
| 2011/0213430 A1 | 9/2011 | Lang et al. | 606/86 R |
| 2011/0213431 A1 | 9/2011 | Fitz et al. | 606/86 R |
| 2011/0218539 A1 | 9/2011 | Fitz et al. | 606/87 |
| 2011/0218584 A1 | 9/2011 | Fitz et al. | 606/86 R |
| 2011/0230888 A1 | 9/2011 | Lang et al. | 606/87 |
| 2011/0238073 A1 | 9/2011 | Lang et al. | 606/89 |
| 2011/0313423 A1 | 12/2011 | Lang et al. | 606/87 |
| 2011/0319897 A1 | 12/2011 | Lang et al. | 606/79 |
| 2011/0319900 A1 | 12/2011 | Lang et al. | 606/87 |
| 2012/0029520 A1 | 2/2012 | Lang et al. | 606/89 |
| 2012/0041446 A1 | 2/2012 | Wong et al. | 606/96 |
| 2012/0066892 A1 | 3/2012 | Lang et al. | 29/592 |
| 2012/0071881 A1 | 3/2012 | Lang et al. | 606/87 |
| 2012/0071882 A1 | 3/2012 | Lang et al. | 606/88 |
| 2012/0071883 A1 | 3/2012 | Lang et al. | 606/88 |
| 2012/0072185 A1 | 3/2012 | Lang et al. | 703/1 |
| 2012/0101503 A1 | 4/2012 | Lang et al. | 606/87 |
| 2012/0143197 A1 | 6/2012 | Lang et al. | 606/87 |
| 2012/0151730 A1 | 6/2012 | Fitz et al. | 29/407.01 |
| 2012/0158001 A1 | 6/2012 | Burdulis, Jr. et al. | 606/88 |

FOREIGN PATENT DOCUMENTS

| | | |
|---|---|---|
| DE | 3516743 | 11/1986 |
| DE | 44 34 539 | 4/1996 |
| DE | 20303498 | 8/2003 |
| EP | 0337901 | 10/1989 |
| EP | 0528080 | 2/1993 |
| EP | 0 704 193 | 4/1996 |
| EP | 0626156 | 7/1997 |
| EP | 0613380 | 12/1999 |
| EP | 0993807 | 4/2000 |
| EP | 1074229 | 2/2001 |
| EP | 1077253 | 2/2001 |
| EP | 1120087 | 8/2001 |
| EP | 1129675 | 9/2001 |
| EP | 1132061 | 9/2001 |
| EP | 0732091 | 12/2001 |
| EP | 0896825 | 7/2002 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| EP | 0530804 | 6/2004 |
| FR | 2819714 | 7/2002 |
| GB | 1451283 | 9/1976 |
| GB | 2291355 | 1/1996 |
| GB | 2348373 | 10/2000 |
| JP | 1-249049 | 10/1989 |
| JP | 8-173465 | 7/1996 |
| JP | 9-206322 | 8/1997 |
| JP | 2002-102236 | 4/2002 |
| WO | WO 87/02882 | 5/1987 |
| WO | WO 90/09769 | 9/1990 |
| WO | WO 93/04710 | 3/1993 |
| WO | WO 93/09819 | 5/1993 |
| WO | WO 93/25157 | 12/1993 |
| WO | WO 95/27450 | 10/1995 |
| WO | WO 95/28688 | 10/1995 |
| WO | WO 95/30390 | 11/1995 |
| WO | WO 95/32623 | 12/1995 |
| WO | WO 96/24302 | 8/1996 |
| WO | WO 97/25942 | 7/1997 |
| WO | WO 97/26847 | 7/1997 |
| WO | WO 97/27885 | 8/1997 |
| WO | WO 97/38676 | 10/1997 |
| WO | WO 98/12994 | 4/1998 |
| WO | WO 98/20816 | 5/1998 |
| WO | WO 98/30617 | 7/1998 |
| WO | WO 98/32384 | 7/1998 |
| WO | WO 99/02654 | 1/1999 |
| WO | WO 99/08598 | 2/1999 |
| WO | WO 99/08728 | 2/1999 |
| WO | WO 99/40864 | 8/1999 |
| WO | WO 99/42061 | 8/1999 |
| WO | WO 99/47186 | 9/1999 |
| WO | WO 99/51719 | 10/1999 |
| WO | WO 99/56674 | 11/1999 |
| WO | WO 00/09179 | 2/2000 |
| WO | WO 00/15153 | 3/2000 |
| WO | WO 00/35346 | 6/2000 |
| WO | WO 00/48550 | 8/2000 |
| WO | WO 00/59411 | 10/2000 |
| WO | WO 00/74554 | 12/2000 |
| WO | WO 01/10356 | 2/2001 |
| WO | WO 01/17463 | 3/2001 |
| WO | WO 01/19254 | 3/2001 |
| WO | WO 01/35968 | 5/2001 |
| WO | WO 01/45764 | 6/2001 |
| WO | WO 01/66021 | 9/2001 |
| WO | WO 01/68800 | 9/2001 |
| WO | WO 01/70142 | 9/2001 |
| WO | WO 01/91672 | 12/2001 |
| WO | WO 02/00270 | 1/2002 |
| WO | WO 02/00275 | 1/2002 |
| WO | WO 02/02158 | 1/2002 |
| WO | WO 02/22013 | 3/2002 |
| WO | WO 02/22014 | 3/2002 |
| WO | WO 02/23483 | 3/2002 |
| WO | WO 02/34310 | 5/2002 |
| WO | WO 02/36147 | 5/2002 |
| WO | WO 02/096268 | 12/2002 |
| WO | WO 03/007788 | 1/2003 |
| WO | WO 03/037192 | 5/2003 |
| WO | WO 03/047470 | 6/2003 |
| WO | WO 03/051210 | 6/2003 |
| WO | WO 03/055400 | 7/2003 |
| WO | WO 2004/043305 | 5/2004 |

| | | |
|---|---|---|
| WO | WO 2004/049981 | 6/2004 |
| WO | WO 2005/051239 | 6/2005 |
| WO | WO 2005/051240 | 6/2005 |
| WO | WO 2006/060795 | 6/2006 |
| WO | WO 2006/127283 | 11/2006 |
| WO | WO 2007/041375 | 4/2007 |
| WO | WO 2007/092841 | 8/2007 |
| WO | WO 2008/112996 | 9/2008 |
| WO | WO 2008/117028 | 10/2008 |
| WO | WO 2008/157412 | 12/2008 |
| WO | WO 2009/111639 | 9/2009 |
| WO | WO 2010/121147 | 10/2010 |

OTHER PUBLICATIONS

Aragenson et al., "Is There a Place for Patellofemoral Arthroplasty?," Clinical Orthopaedics and Related Research No. 321, pp. 162-167 (1995).

Blum et al., "Knee Arthroplasty in Patients with Rheumatoid Arthritis," Ann. Rheum. Dis. 33 (1): 1-11 (1974).

Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).

Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).

Cameron, et al., "Review of a Failed Knee Replacement and Some Observations on the Design of a Knee Resurfacing Prosthesis," Arch. Orthop Trauma Surg. 97(2):87-89 (1980).

Carr et al., "Surface Interpolation with Radial Basis Functions for Medical Imaging," IEEE Transactions on Medical Imaging, IEEE, Inc. New York, vol. 16, pp. 96-107 (Feb. 1997).

Clary et al., "Experience with the MacIntosh Knee Prosthesis," South Med. J. 65(3):265-272 (1972).

Conaty, et al., "Surgery of the Hip and Knee in Patients with Rheumatoid Arthritis," J. Bone Joint Surg. Am. 55(2):301-314 (1973).

De Winter et al., "The Richards Type II Patellofemoral Arthroplasty", Acta Orthop Scand 2001; 72 (5): 487-490.

Ghelman et al., "Kinematics of the Knee After Prosthetic Replacements", Clin. Orthop. May 1975: (108): 149-157.

Hastings et al., "Double Hemiarthroplasty of the Knee in Rheumatoid Arthritis," A Survey of Fifty Consecutive Cases, J. Bone Joint Surg. Br. 55(1):112-118 (1973).

Henderson et al., "Experience with the Use of the Macintosh Prosthesis in Knees of Patients with Pheumatoid Arthritis," South. Med. J. 62(11):1311-1315 (1969).

Jessop et al., "Follow-up of the MacIntosh Arthroplasty of the Knee Joint," Rheumatol Phys. Med. 11(5):217-224 (1972).

Kates, et al., "Experiences of Arthroplasty of the Rheumatoid Knee Using MacIntosh Prostheses," Ann. Rheum. Dis. 28(3):328 (1969).

Kay et al., The MacIntosh Tibial Plateau Hemiprosthesis for the Rheumatoid Knee, J. Bone Joint Surg. Br. 54(2):256-262 (1972).

Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).

Kshirsagar et al., "Measurement of Localized Cartilage Volume and Thickness of Human Knee Joints by Computer Analysis of Three-Dimensional Magnetic Resonance Images", Invest Radiol. May 1998, 33(5): 289-299 T. 111, V. 111.

Lam et al., "X-Ray Diagnosis: A Physician's Approach", Editor Lam, 1998, Springer-Verlag publishers, Title page and Table of Contents pgs. Only (ISBN 9813083247).

Leenslag et al., "A Porous Composite for Reconstruction of Meniscus Lesions," Biological and Biomechanical Perform. of Biomaterials, Elsevier Science Publishers Amsterdam pp. 147-152 (1986).

MacIntosh, "Arthroplasty of the Knee in Rheumatoid Arthritis," Proceedings and Reports of Councils and Assotions, J. Bone & Joint Surg., vol. 48B No. (1): 179 (Feb. 1996).

MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).

MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).

MacIntosh, "Hemiarthroplasty of the Knee Using a Space Occupying Prosthesis for Painful Varus and Valgus Deformities," J. Bone Joint Surg. Am. Dec. 1958:40-A:1431.

Matsen, III et al., "Robotic Assistance in Orthopaedic Surgery: A Proof of Principle Using Distal Femoral Arthroplasty", Clinical Ortho. and Related Research, 296:178-186 (1993).

McCollum, et al., "Tibial Plateau Prosthesis in Arthroplasty of the Knee," J. Bone Joint Surg. Am. 1970 52(4):827-8 (Feb. 1996).

McKeever, "The Classic Tibial Plateau Prosthesis," Clin. Orthop. Relat. Res. (192):3-12 (1985).

Nelson et al., "Arthroplasty and Arthrodesis of the Knee Joint," Orthop. Clin. North Am. 2 (1): 245-64 (1971).

Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).

Porter et al., "MacIntosh Arthroplasty: A Long-Term Review," J. R. Coll. Surg. Edin. (192):199-201 (1988).

Portheine et al., "CT-Based Planning and Individual Template Navigation in TKA", Navigation and Robotics in Total Joint and Spine Surgery, Springer, 48:336-342 (2004).

Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.

Potter, "Arthroplasty of the Knee With Tibial Metallic Implants of the McKeever and MacIntosh Design," Sug. Clin. North Am. 49(4):903-915 (1969).

Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).

Radermacher, Helmholtz Institute of Biomedical Technology, "Computer-Assisted Planning and Execution of Orthopedic Surgery Using Individual Surgical Templates", May 18, 1999.

Radermacher, German Version: Helmholtz Institute of Biomedical Technology, "Computer-Assisted Planning and Execution of Orthopedic Surgety Using Individual Surgical Templates", May 18, 1999.

Radermacher, "Computer Assisted Orthopaedic Surgery With Image Based Individual Templates" Clinical Orthopaedics, Sep. 1998, vol. 354, pp. 28-38.

Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-616, 1997.

Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.

Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.

Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.

Ranawat et al., "MacIntosh Hemiarthroplasty in Rheumatoid Knee," Acta Orthop Belg., 39 (1): 1-11 (1973).

Schorn et al., "MacIntosh Arthroplasty in Rheumatoid Arthritis," Rheumatol Rehabil. Aug. 1978:17(3):155-163.

Slone et al., "Body CT: A Practical Approach", Editor Slone, 1999 McGraw-Hill publishers, Title page and Table of Contents pgs. Only (ISBN 007058219).

Stauffer et al., "The MacIntosh Prosthesis. Prospective Clinical and Gait Evaluation," Arch. Surg. 110(6):717-720 (1975).
Stout et al., "X-Ray Structure Determination: A Practical Guide", 2nd Ed. Editors Stout and Jensen, 1989, John Wiley & Sons, Title page and Table of Contents pgs. Only (ISBN 0471607118).
Taha et al., "Modeling and Design of a Custom Made Cranium Implant for Large Skull Reconstruction Before A Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.
Vandeberg et al., "Assessment of Knee Cartilage in Cadavers With Dual-Detector Spiral CT Arthrography and MR Imaging", Radiology, Feb. 2002: 222(2): 430-435 T.195, V.V.
Wordsworth et al., "MacIntosh Arthroplasty for the Rheumatoid Knee: A 10-year Follow Up," Ann. Rheum. Dis. 44(11):738-741 (1985).
International Searching Authority, International Search Report—International Application No. PCT/US03/38158, dated Feb. 23, 2005, 7 pages.
International Searching Authority, European Search Report—Application No. EP 03790194, dated Jul. 13, 2006, 7 pages.
International Searching Authority, International Search Report—International Application No. PCT/US03/32123, dated Mar. 17, 2004, 7 pages.
International Searching Authority, International Search Report—International Application No. PCT/US04/39616, dated Mar. 28, 2005, together with the Written Opinion of the International Searching Authority, 6 pages.
International Searching Authority, International Search Report—International Application No. PCT/US04/39714, dated May 13, 2005, together with the Written Opinion of the International Searching Authority, 8 pages.
International Searching Authority, International Search Report—International Application No. PCT/US2005/044008, dated Mar. 30, 2006, together with the Written Opinion of the International Searching Authority, 12 pages.
International Searching Authority, International Search Report—International Application No. PCT/US2006/045172, dated Apr. 19, 2007, 5 pages.
International Searching Authority, International Search Report—International Application No. PCT/US2007/061681, dated Sep. 7, 2007, together with the Written Opinion of the International Searching Authority, 12 pages.
European Patent Office, Supplementary European Search Report—Application No. 04812187.5, dated Sep. 27, 2007, 3 pages.
International Searching Authority, International Preliminary Report on Patentability—International Application No. PCT/US2005/044008, dated Jun. 14, 2007, together with the Written Opinion of the International Searching Authority, 8 pages.
United States Patent and Trademark Office, Office Action dated Jun. 15, 2007, pertaining to U.S. Appl. No. 09/882,363, 9 pages.
Bromberg & Sunstein LLP, Response to Office Action dated Jun. 15, 2007, pertaining to U.S. Appl. No. 09/882,363, 12 pages.
United States Patent and Trademark Office, Office Action dated Mar. 21, 2008, pertaining to U.S. Appl. No. 09/882,363, 12 pages.
Bromberg & Sunstein LLP, Response to Office Action dated Jan. 30, 2007, pertaining to U.S. Appl. No. 09/882,363, 7 pages.
International Searching Authority, International Search Report—International Application No. PCT/US2008/066994, dated Feb. 19, 2009, together with the Written Opinion of the International Searching Authority, 16 pages.
Bromberg & Sunstein LLP, Amendment dated Sep. 22, 2008, pertaining to U.S. Appl. No. 09/882,363, 15 pages.
United States Patent and Trademark Office, Office Action dated Jan. 6, 2009, pertaining to U.S. Appl. No. 09/882,363, 9 pages.
Bromberg & Sunstein LLP, Request for Continued Examination dated Jul. 6, 2009, pertaining to U.S. Appl. No. 09/882,363, 16 pages.
Bromberg & Sunstein LLP—U.S. Appl. No. 12/361,213, filed Jan. 28, 2009, 76 pages.

Bromberg & Sunstein LLP—U.S. Appl. No. 12/398,753, filed Mar. 5, 2009 141 pages.
International Searching Authority, International Search Report—International Application No. PCT/US2009/036189, dated Jul. 13, 2009, together with the Written Opinion of the International Searching Authority, 11 pages.
International Searching Authority, International Search Report—International Application No. PCT/US2008/057045, dated Jul. 15, 2008, together with the Written Opinion of the International Searching Authority, 13 pages.
United States Patent and Trademark Office, Office Action dated Oct. 20, 2010, pertaining to U.S. Appl. No. 12/135,719, 10 pages.
Sunstein Kann Murphy & Timbers LLP, Response to Office Action dated Aug. 26, 2010, pertaining to U.S. Appl. No. 12/361,213, 22 pages.
United States Patent and Trademark Office, Office Action dated Feb. 28, 2011, pertaining to U.S. Appl. No. 12/048,764, 12 pages.
European Patent Office, Extended European Search Report—European Application No. 101871743.5-2310, dated Mar. 11, 2011, 6 pages.
Delp et al., "A Graphics-Based Software System to Develop and Analyze Models of Musculoskeletal Structures," Comput. Biol. Med., vol. 25, No. 1, pp. 21-34, 1995.
Farrar et al., "Computed Tomography Scan Scout Film for Measurement of Femoral Axis in Knee Arthroplasty," J. Arthroplasty, vol. 14, No. 8, pp. 1030-1031, 1999.
Kim et al., "Measurement of Femoral Neck Anteversion in 3D. Part 1: 3D Imaging Method," Med. And Viol. Eng. And Computing, vol. 38, No. 6, pp. 603-609, 2000.
Lam et al., "Varus/Valgus Alignment of the Femoral Component in Total Knee Arthroplasty," The Knee, vol. 10, pp. 237-241, 2003.
Lu et al., "In vitro degradation of porous poly(L-lactic acid) foams", Biomaterials, 21(15):1595-1605, Aug. 2000.
Mahaisavariya et al., "Morphological Study of the Proximal Femur: A New Method of Geometrical Assessment Using 3 Dimensional Reverse Engineering," Med. Eng. And Phys., vol. 24, pp. 617-622, 2002.
Marler et al., "Soft-Tissue Augmentation with Injectable Alginate and Syngeneic Fibroblasts", Plastic & Reconstructive Surgery, 105(6):2049-2058, May 2000.
Testi et al., "Border Tracing Algorithm Implementation for the Femoral Geometry Reconstruction," Comp. Meth. And Programs in Biomed., vol. 65, pp. 175-182, 2001.
Wiese et al., "Biomaterial properties and biocompatibility in cell culture of a novel self-inflating hydrogel tissue expander", J. Biomedical Materials Research Part A, 54(2):179-188, Nov. 2000.
Yusof et al., "Preparation and characterization of chitin beads as a wound dressing precursor", J. Biomedical Materials Research Part A, 54(1):59-68, Oct. 2000.
International Searching Authority, Invitation to Pay Additional Fees, and Where Applicable, Protest Fee—International Application No. PCT/US2008/066994, dated Oct. 21, 2008, 5 pages.
Sunstein Kann Murphy & Timbers LLP, Supplemental Amendment dated Sep. 18, 2009, pertaining to U.S. Appl. No. 09/882,363, 11 pages.
United States Patent and Trademark Office, Office Action dated May 5, 2008, pertaining to U.S. Appl. No. 10/724,010, 13 pages.
Bromberg & Sunstein LLP, Request for Continued Examination and Response dated Nov. 4, 2008, pertaining to U.S. Appl. No. 10/724,010, 15 pages.
United States Patent and Trademark Office, Office Action dated Jan. 29, 2009, pertaining to U.S. Appl. No. 10/724,010, 9 pages.
Bromberg & Sunstein LLP, Response to Office Action dated Jan. 29, 2009, pertaining to U.S. Appl. No. 10/724,010, 16 pages.
United States Patent and Trademark Office, Office Action dated Nov. 26, 2007, pertaining to U.S. Appl. No. 11/002,573, 15 pages.
Bromberg & Sunstein LLP, Request for Continued Examination and Response dated Feb. 27, 2008, pertaining to U.S. Appl. No. 11/002,573, 19 pages.
United States Patent and Trademark Office, Office Action dated May 9, 2008, pertaining to U.S. Appl. No. 11/002,573, 17 pages.
Bromberg & Sunstein LLP, Amendment dated Aug. 12, 2008, pertaining to U.S. Appl. No. 11/002,573, 25 pages.

Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
United States Patent and Trademark Office, Office action dated Jan. 26, 2010, pertaining to U.S. Appl. No. 11/671,745, 9 pages.
International Searching Authority, International Search Report—International Application No. PCT/US10/31415, dated Jun. 29, 2010, together with the Written Opinion of the International Searching Authority, 9 pages.
Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).
Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).
CAOS, "MIS meets CAOS Spring 2005 Symposium Schedule", *CAOS Spring 2005 Symposium*, pp. 1-9, May 19, 2005.
Chelule et al., "Patient-Specific Template to Preserve Bone Stock in Total Knee Replacement: Preliminary Results", *15th Annual ISTA Symposium*, Sep. 2002, 1 page.
Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).
Hafez et al., "Computer-assisted Total Knee Arthroplasty Using Patient-specific Templating," *Clinical Orthopaedics and Related Research*, No. 444, pp. 184-192 (Mar. 2006).
Radermacher et al., "Computer Assisted Orthopedic Surgery by Means of Individual Templates • Aspects and Analysis of Potential Applications ." *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).
Schiffers et al., In German: "Planning and execution of orthopedic surgery using individualized templates," *Der Orthopäde*, Springer-Verlag, vol. 29, No. 7, pp. 636-640, (Jul. 2000).
Schiffers et al., English Translation with Certification: "Planning and execution of orthopedic surgery using individualized templates," *Der Orthopäde*, Springer-Verlag, vol. 29, No. 7, pp. 636-640, (Jul. 2000).
Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., In German: "Custom-made knee endoprosthetics using subtraction data of three-dimensional CT scans—A new approach," *Der Orthopäde*, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," *Der Orthopäde*, Springer-Verlag, vol. 29, No. 7, pp. 641-644, (Jul. 2000).
United States Patent and Trademark Office, Office Action dated Apr. 20, 2011, pertaining to U.S. Appl. No. 12/135,612, 13 pages.
United States Patent and Trademark Office, Office Action dated Sep. 26, 2011 pertaining to U.S. Appl. No. 12/048,764, 9 pages.
United States Patent and Trademark Office, Office Action dated Oct. 23, 2009, pertaining to U.S. Appl. No. 10/764,010, 13 pages.
United States Patent and Trademark Office, Office Action dated Jan. 9, 2009, pertaining to U.S. Appl. No. 10/764,010 11 pages.
Bromberg & Sunstein LLP, Response to Office Action dated Jan. 9, 2009, pertaining to U.S. Appl. No. 10/764,010, 25 pages.
United States Patent and Trademark Office, Office Action dated May 17, 2010, pertaining to U.S. Appl. No. 10/764,010, 12 pages.
Sunstein Kann Murphy & Timbers LLP, Response to Office Action dated May 17, 2010, pertaining to U.S. Appl. No. 10/764,010, 21 pages.
United States Patent and Trademark Office, Notice of Allowance dated Dec. 16, 2010, pertaining to U.S. Appl. No. 10/764,010, 11 pages.
United States Patent and Trademark Office, Notice of Allowance dated Aug. 5, 2011, pertaining to U.S. Appl. No. 10/764,010, 14 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.
Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Preliminary Amendment dated Aug. 12, 2011, pertaining to U.S. Appl. No. 13/017,886, 13 pages.
United States Patent and Trademark Office, Office Action dated Jun. 23, 2011 pertaining to U.S. Appl. No. 11/410,515, 13 pages.
Birnbaum et al., "Computer-Assisted Orthopedic Surgery With Individual Templates and Comparison to Conventional Operation Method", Spine, vol. 26, No. 4, pp. 365-369, Feb. 2001.
Chelule et al., "Computer Aided Design of Personalized Jigs in Total Knee Replacement", $3^{rd}$ Annual Meeting of CAOS Int'l Proc., Spain, Jun. 18, 21, 2003, pp. 58-59.
Froemel et al., "Computer Assisted Template Based Navigation for Total Knee Replacement", Documents presented at CAOS on Jun. 17, 2001, 4 pages.
Hafez et al., "Computer Assisted Total Knee Replacement: Could a Two-Piece Custom Template Replace the Complex Conventional Instrumentations?", $4^{th}$ Annual Meeting of CAOS Int'l Proc., Chicago, Jun. 16-19, 2004, pp. 63-64.
Hafez et al., "Computer-Assisted Total Hip Arthroplasty: The Present and the Future", Future Rheumatol., vol. 1, pp. 121-131, 2006.
Portheine et al., In German: "Potentials of CT-based Planning and Template-based Procedure in Hip and Knee Surgery", Orth. Prac., vol. 36, pp. 786-791, 2000.
Portheine et al., English Translation with Certification: "Potentials of CT-based Planning and Template-based Procedure in Hip and Knee Surgery", Orth. Prac., vol. 36, pp. 786-791, 2000.
Portheine, In German: "Model-Based Operation Planning in Orthopedic Surgery", Thesis, RWTH Aachen University, Apr. 22, 2004, 90 pages.
Portheine, English Translation with Certification: "Model-Based Operation Planning in Orthopedic Surgery", Thesis, RWTH Aachen University, Apr. 22, 2004, 170 pages.

Radermacher et al., "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.

Radermacher et al., "Computer Assisted Matching of Planning and Execution in Orthopedic Surgery", IEEE, EMBS, San Diego, 1993, pp. 946-947.

Radermacher, "Computer Assisted Matching of Planning and Execution in Orthopedic Surgery", Slide Presentation, San Diego, Nov. 29, 1993, 22 pages.

Radermacher et al., "Computer Integrated Advanced Orthopedics (CIAO)", 2nd European Conference on Eng. And Med., presented Apr. 26, 1993, 12 pages.

Radermacher et al., "Surgical Therapy Technology", Helmholtz-Institut Aachen Research Report, 1993-1994, pp. 189-219.

Radermacher, "Image Guided Orthopedic Surgery with Individual Templates", Helmhotz-Institute for Biomed. Eng., 2 pages, 1997.

Radermacher et al., In German: "Computer-assisted operative interventions in orthopedics—are there prospects for endoprosthetics as well?", Prac. Ortho., vol. 27, pp. 149-164, 1997.

Radermacher et al., English Translation with Certification: "Computer-assisted operative interventions in orthopedics—are there prospects for endoprosthetics as well?", Prac. Ortho., vol. 27, pp. 1-17, 1997.

Radermacher et al., "Computer Based Decision Support for the Planning of Contact Faces for Manual Registration with Individual Templates", Helmholtz-Institute for Biomed. Eng., 7 pages, 1997-98.

Radermacher, In German: "Computer-Based Decision Support in the Selection and Evaluation of Contact Surfaces for Manual Referencing", Lecture presented at Helmholtz Meeting '98 and OSS '98, 7 pages.

Radermacher, English Translation with Certification: "Computer-Based Decision Support in the Selection and Evaluation of Contact Surfaces for Manual Referencing", Lecture presented at Helmholtz Meeting '98 and OSS '98, 8 pages.

Radermacher et al., In German: "Computer-Assisted Planning and Operation in Orthopedics", Orth. Prac. 36th year, pp. 731-737, Dec. 2000.

Radermacher et al., English Translation with Certification: "Computer-Assisted Planning and Operation in Orthopedics", Orth. Prac. 36th year, pp. 731-737, Dec. 2000.

Radermacher, "Template Based Navigation—An Efficient Technique for Hip and Knee Surgery", CAOS First Asian Meet, India, Mar. 27-28, 2004, pp. 44-50.

Rau et al., "Small and Neat", Medical Tech. Int'l, pp. 65, 67 and 69, 1993-94.

Schkommadau et al., "Clinical Application of Individual Templates for Pedicle Screw Placement in Comparison to Computer Navigation", Poster presented at CAOS, Feb. 18, 2000, 1 page.

Schkommadau et al., In German: "Clinical Experience With the Individual Template Technique", Orth. Prac., vol. 37, No. 1, pp. 19-22, 2001.

Schkommadau et al., English Translation with Certification: "Clinical Experience With the Individual Template Technique", Orth. Prac., vol. 37, No. 1, pp. 19-22, 2001.

Seel et al., "Three-Dimensional Planning and Virtual Radiographs in Revision Total Hip Arthroplasty for Instability", Clinical Orthopaedics and Related Research, No. 442, pp. 35-38, Jan. 2006.

Staudte et al., In German: "Computer-Assisted Operation Planning and Technique in Orthopedics", North Rhine-Westphalia Acad. For Sciences, Lecture N.444, ISSN 0944-8799, 2000, 17 pages.

Staudte et al., English Translation with Certification: "Computer-Assisted Operation Planning and Technique in Orthopedics", North Rhine-Westphalia Acad. For Sciences, Lecture N.444, ISSN 0944-8799, 2000, 34 pages.

European Patent Office, European Search Report—Application No. 09716738.1 dated Feb. 6, 2012, 10 pages.

European Patent Office, Extended European Search Report—Application No. 10181149.5-1526 dated Apr. 19, 2012, 9 pages.

European Patent Office, Extended European Search Report—Application No. 10181198.2-1526 dated Apr. 19, 2012, 9 pages.

United States Patent and Trademark Office, Office Action dated Jan. 13, 2012, pertaining to U.S. Appl. No. 12/776,840, 10 pages.

United States Patent and Trademark Office, Office Action dated Jan. 26, 2012, pertaining to U.S. Appl. No. 12/139,324, 14 pages.

United States Patent and Trademark Office, Office Action dated Jun. 5, 2012, pertaining to U.S. Appl. No. 12/776,984, 7 pages.

* cited by examiner

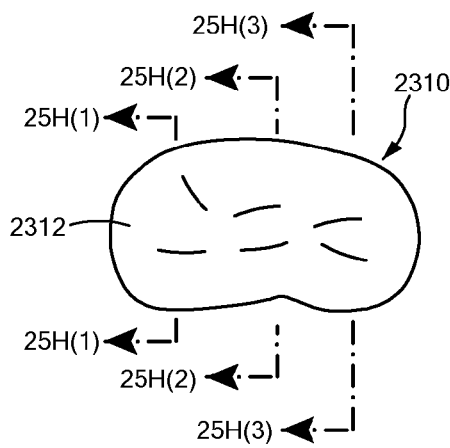
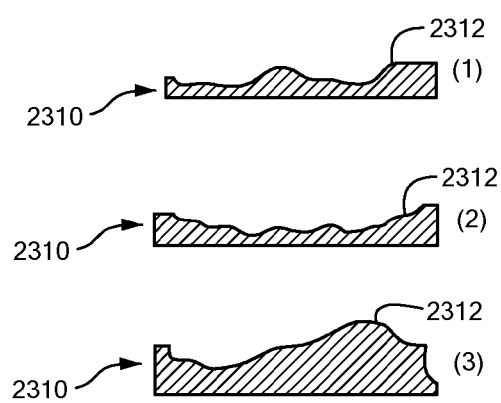
*FIG. 5G*                *FIG. 5H*
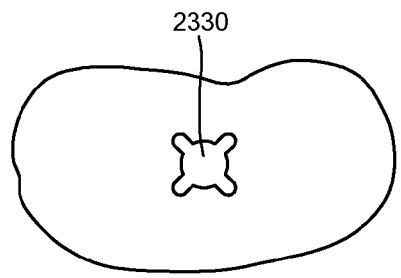
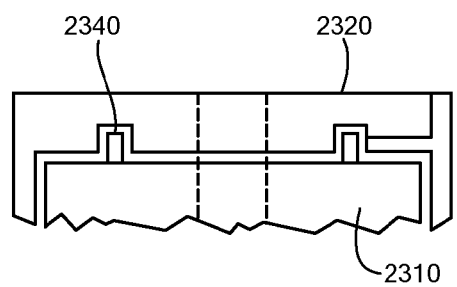
*FIG. 5I*                *FIG. 5J*
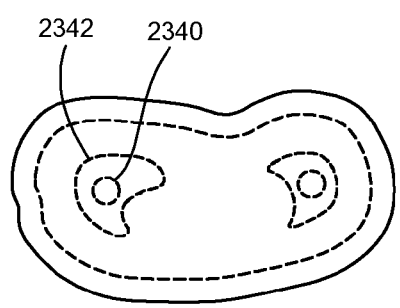
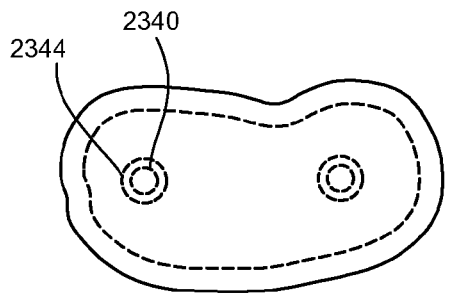
*FIG. 5K*                *FIG. 5L*

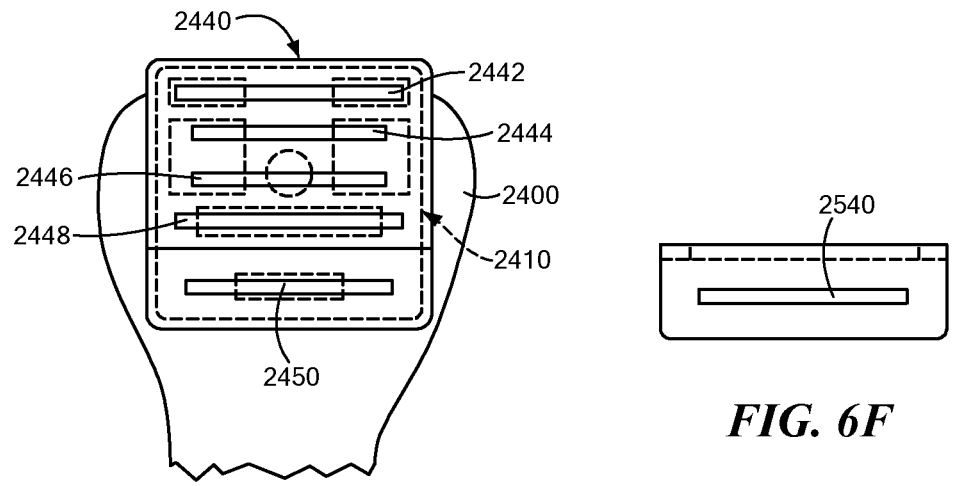
*FIG. 6E*
*FIG. 6F*
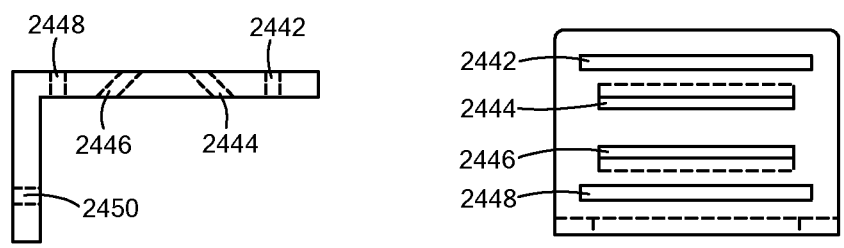
*FIG. 6G*
*FIG. 6H*
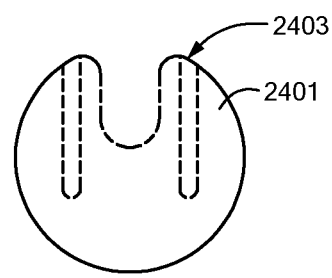
*FIG. 6I*

PATIENT SELECTABLE JOINT ARTHROPLASTY DEVICES AND SURGICAL TOOLS

CROSS-REFERENCE TO RELATED APPLICATIONS

This application claims priority from U.S. Provisional Application Ser. No. 61/034,048, filed Mar. 5, 2008, entitled "Patient Selectable Joint Arthroplasty Devices and Surgical Tools," and U.S. Provisional Application Ser. No. 61/052,430, filed May 12, 2008, entitled "Patient Selectable Joint Arthroplasty Devices and Surgical Tools."

This application is also a continuation in part of U.S. Ser. No. 11/671,745, filed Feb. 6, 2007, entitled "Patient Selectable Joint Arthroplasty Devices and Surgical Tools", which in turn claims the benefit of U.S. Ser. No. 60/765,592 entitled "SURGICAL TOOLS FOR PERFORMING JOINT ARTHROPLASTY" filed Feb. 6, 2006; U.S. Ser. No. 60/785,168, entitled "SURGICAL TOOLS FOR PERFORMING JOINT ARTHROPLASTY" filed Mar. 23, 2006; and U.S. Ser. No. 60/788,339, entitled "SURGICAL TOOLS FOR PERFORMING JOINT ARTHROPLASTY" filed Mar. 31, 2006.

U.S. Ser. No. 11/671,745 is also a continuation-in-part of U.S. Ser. No. 11/002,573 for "SURGICAL TOOLS FACILITATING INCREASED ACCURACY, SPEED AND SIMPLICITY IN PERFORMING JOINT ARTHROPLASTY" filed Dec. 2, 2004 which is a continuation-in-part of U.S. Ser. No. 10/724,010 for "PATIENT SELECTABLE JOINT ARTHROPLASTY DEVICES AND SURGICAL TOOLS FACILITATING INCREASED ACCURACY, SPEED AND SIMPLICITY IN PERFORMING TOTAL AND PARTIAL JOINT ARTHROPLASTY" filed Nov. 25, 2003 which is a continuation-in-part of U.S. Ser. No. 10/305,652 entitled "METHODS AND COMPOSITIONS FOR ARTICULAR REPAIR," filed Nov. 27, 2002, which is a continuation-in-part of U.S. Ser. No. 10/160,667, filed May 28, 2002, which in turn claims the benefit of U.S. Ser. No. 60/293,488 entitled "METHODS TO IMPROVE CARTILAGE REPAIR SYSTEMS", filed May 25, 2001, U.S. Ser. No. 60/363,527, entitled "NOVEL DEVICES FOR CARTILAGE REPAIR, filed Mar. 12, 2002 and U.S. Ser. Nos. 60/380,695 and 60/380,692, entitled "METHODS AND COMPOSITIONS FOR CARTILAGE REPAIR," and "METHODS FOR JOINT REPAIR," filed May 14, 2002.

U.S. Ser. No. 11/671,745 is also a continuation-in-part of U.S. Ser. No. 10/728,731, entitled "FUSION OF MULTIPLE IMAGING PLANES FOR ISOTROPIC IMAGING IN MRI AND QUANTITATIVE IMAGE ANALYSIS USING ISOTROPIC OR NEAR-ISOTROPIC IMAGING," filed Dec. 4, 2003, which claims the benefit of U.S. Ser. No. 60/431,176, entitled "FUSION OF MULTIPLE IMAGING PLANES FOR ISOTROPIC IMAGING IN MRI AND QUANTITATIVE IMAGE ANALYSIS USING ISOTROPIC OR NEAR ISOTROPIC IMAGING," filed Dec. 4, 2002.

U.S. Ser. No. 11/671,745 is also a continuation-in-part of U.S. Ser. No. 10/681,750, entitled "Minimally Invasive Joint Implant with 3-Dimensional Geometry Matching the Articular Surfaces," filed Oct. 7, 2003, which claims the benefit of U.S. Ser. No. 60/467,686, entitled "Joint Implants," filed May 2, 2003 and U.S. Ser. No. 60/416,601, entitled Minimally Invasive Joint Implant with 3-Dimensional Geometry Matching the Articular Surfaces," filed Oct. 7, 2002.

Each of the above-described applications is hereby incorporated by reference in their entirety.

FIELD OF THE INVENTION

The present invention relates to orthopedic methods, systems and prosthetic devices and more particularly relates to surgical templates designed to achieve optimal cut planes in a joint in preparation for installation of a joint implant.

BACKGROUND OF THE INVENTION

There are various types of cartilage, e.g., hyaline cartilage and fibrocartilage. Hyaline cartilage is found at the articular surfaces of bones, e.g., in the joints, and is responsible for providing the smooth gliding motion characteristic of moveable joints. Articular cartilage is firmly attached to the underlying bones and measures typically less than 5 mm in thickness in human joints, with considerable variation depending on joint and site within the joint. In addition, articular cartilage is aneural, avascular, and alymphatic. In adult humans, this cartilage derives its nutrition by a double diffusion system through the synovial membrane and through the dense matrix of the cartilage to reach the chondrocyte, the cells that are found in the connective tissue of cartilage.

Adult cartilage has a limited ability of repair; thus, damage to cartilage produced by disease, such as rheumatoid and/or osteoarthritis, or trauma can lead to serious physical deformity and debilitation. Furthermore, as human articular cartilage ages, its tensile properties change. The superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

For example, the superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

Once damage occurs, joint repair can be addressed through a number of approaches. One approach includes the use of matrices, tissue scaffolds or other carriers implanted with cells (e.g., chondrocytes, chondrocyte progenitors, stromal cells, mesenchymal stem cells, etc.). However, clinical outcomes with biologic replacement materials such as allograft and autograft systems and tissue scaffolds have been uncertain since most of these materials cannot achieve a morphologic arrangement or structure similar to or identical to that of normal, disease-free human tissue it is intended to replace. Moreover, the mechanical durability of these biologic replacement materials remains uncertain.

Usually, severe damage or loss of cartilage is treated by replacement of the joint with a prosthetic material, for example, silicone, e.g. for cosmetic repairs, or metal alloys. Implantation of these prosthetic devices is usually associated with loss of underlying tissue and bone without recovery of the full function allowed by the original cartilage and, with some devices, serious long-term complications associated with the loss of significant amount of tissue and bone can include infection, osteolysis and also loosening of the implant.

As can be appreciated, joint arthroplasties are highly invasive and require surgical resection of the entire, or a majority of the, articular surface of one or more bones involved in the repair. Typically with these procedures, the marrow space is fairly extensively reamed in order to fit the stem of the prosthesis within the bone. Reaming results in a loss of the patient's bone stock and over time subsequent osteolysis will frequently lead to loosening of the prosthesis. Further, the area where the implant and the bone mate degrades over time requiring the prosthesis to eventually be replaced. Since the patient's bone stock is limited, the number of possible replacement surgeries is also limited for joint arthroplasty. In short, over the course of 15 to 20 years, and in some cases even shorter time periods, the patient can run out of therapeutic options ultimately resulting in a painful, non-functional joint.

A variety of tools, such as a guide for making one or more surgical cuts, are currently available to assist surgeons. However, these devices are not designed to substantially conform to the actual shape (contour) of the remaining cartilage in vivo and/or the underlying bone. Thus, use and proper alignment of the tool and integration of the implant can be extremely difficult due to differences in thickness and curvature between the patient's surrounding cartilage and/or the underlying subchondral bone and the prosthesis. Thus, there remains a need for tools that increase the accuracy of cuts made to the bone in a joint in preparation for surgical implantation of, for example, an artificial joint.

SUMMARY OF THE INVENTION

The present invention provides novel surgical tools and methods. In accordance with one embodiment of the invention, a surgical tool includes a template. The template has at least one contact surface for engaging a surface associated with a joint. The at least one contact surface substantially conforms with the surface. The template further includes at least one guide aperture for directing movement of a surgical instrument.

One embodiment is a system for articular repair that includes a first template having a first surface and a second surface, the first surface conforming with, and substantially a negative of, at least a portion of first side of a joint; a second template having a third surface that conforms with, and is substantially a negative of, a portion of the first side of the joint, the second template including at least one guide for guiding a surgical instrument in making a cut on the first side of the joint; and an attachment mechanism for attaching the second template to the first template.

Other embodiments may include one or more of the following. The first or second template can include a guide for making a vertical cut. The second surface can be at least one of substantially flat, substantially concave, substantially convex, and matched to one of the first or second sides of the joint. The system can include at least one other template, and each of the other templates can be capable of attaching to the second template. The templates can vary in thickness. At least a portion of the first surface can substantially conforms to at least one of uncut subchondral bone, uncut cartilage, and uncut bone of a first or second side of the joint. At least a portion of the second surface can substantially conform to at least one of uncut subchondral bone, uncut cartilage, and uncut bone of a first or second side of a joint. At least a portion of the third surface can substantially conforms to at least one of uncut subchondral bone, uncut cartilage, and uncut bone of a first or second side of a joint. The attachment mechanism can include at least one of a snapfit, dovetail and a cross-pin. The attachment mechanism can allow for rotation relative to one of an anatomical and a biomechanical axis. The joint can be at least one of a hip, knee, ankle, toe joint, shoulder, elbow, wrist, finger joint, spine or spinal joint.

Another embodiment is a system for articular joint repair that includes: a first template having a first surface and a second surface, the first surface substantially a negative of at least a portion of the tibial plateau; a second template having a third surface that is substantially a negative of a portion of the tibia, the second template including at least one guide for guiding a surgical instrument in making a cut on the tibia; and an attachment mechanism for attaching the second template to the first template.

Other aspects of this embodiment may include one or more of the following. The first or second template can include a guide for making a vertical tibial cut. The second surface can be at least one of substantially flat, substantially concave, substantially convex, and matched to one of the tibia and the femur. The system can include at least one other template can have a first surface and a second surface. The first surface can conform with, and be substantially a negative of, at least a portion of the tibial plateau. Each of the other templates can be capable of attaching to the second template, wherein the first template and each of the other templates vary in thickness. At least a portion of the first surface can be substantially a negative of at least one of uncut subchondral bone, uncut cartilage, and uncut bone of a tibia. At least a portion of the second surface can be substantially a negative of at least one of uncut subchondral bone, uncut cartilage, and uncut bone of a tibia. At least a portion of the third surface can be substantially a negative of at least one of uncut subchondral bone, uncut cartilage, and uncut bone of a tibia. The attachment mechanism can include at least one of a snapfit, dovetail and a cross-pin. The attachment mechanism can allow for rotation relative to one of an anatomical and a biomechanical axis. At least one guide can guides a surgical instrument in making a cut on the tibia having a desired slope relative to at least one of a biomechanical and an anatomical axis. The articular joint repair can be a joint resurfacing, including a knee joint resurfacing, a joint replacement or other procedure.

Another embodiment is a system for articular repair that includes a first template having a first surface substantially matching at least a portion of the tibial plateau. The first template can include a medial edge that corresponds to a predetermined location for a vertical tibial cut.

Other embodiments may have one or more of the following. A second template can have a surface substantially matching at least a portion of the tibia, and can include at least one guide for guiding a surgical instrument. The second template can also have an attachment mechanism for attaching the second template to the first template. The first template can include a guide for guiding a surgical instrument. The medial edge can be adapted as a guide for making a vertical tibial cut. The system can have at least one other template having a first surface and a second surface. The first surface can substantially match at least a portion of the tibial plateau. The first template and each of the other templates can vary in thickness. At least a portion of the first surface can substantially match at least one of uncut subchondral bone, uncut cartilage, and uncut bone.

Another embodiment is a kit for testing at least one of ligament balancing and ligament tension, which includes a first template that has at least one surface substantially conforming with at least a portion of a first articular joint surface. The template is configured for placement on the first articular joint surface and between the first articular joint surface and a second articular joint surface, and it has a predefined thickness configured to provide a physical spacer for assessing at least one of ligament balance and ligament tension during a surgical procedure.

Other embodiments can include one or more of the following. The kit can include a second template that has at least one surface substantially conforming with at least the portion of the first articular joint surface. The template can be configured for placement on the first articular joint surface and between the first articular joint surface and the second articular joint surface. The template can have a second predefined thickness configured to provide a physical spacer for assessing at least one of ligament balance and ligament tension during a surgical procedure. The kit can also include additional templates of varying thicknesses. The second template can also have at least one guide for guiding a surgical instrument, and an attachment mechanism for attaching the second template to at least one of the first template and the at least one other template. The kit can be used for articular joints, including a knee joint, a hip joint, a shoulder joint, an elbow joint, a wrist joint, a finger joint, a toe joint, and an ankle joint. At least a portion of the surface can substantially conforms to at least one of uncut subchondral bone, uncut cartilage, and uncut bone.

Another embodiment is a method of partial or total knee replacement or resurfacing that includes: positioning a first surface of a first instrument onto at least a portion of the tibial plateau, the first surface being substantially a negative of at least a portion of the tibial plateau; cross-referencing a second instrument to the first instrument to align position of the second instrument on the tibia, the second instrument including at least one surgical cut guide; and directing a cut using the at least one surgical guide of the second of the second instrument.

Other embodiments can have one or more of the following. The cut can be a tibial cut. The instruments can be templates, surgical tools or other devices. The first instrument can include a guide for making a cut, which can be a vertical or horizontal cut, e.g., on the tibia. The first instrument can include a medial edge that corresponds to a predetermined location for a vertical tibial cut, the method further comprising confirming the proper location of the vertical tibial cut based on the medial edge. At least a portion of the first surface can substantially conform to at least one of uncut subchondral bone, uncut cartilage, and uncut bone. The first surface of the instrument is based, at least in part, on electronic image data of the tibial plateau. Cross-referencing can include attaching the first instrument to the second instrument. The at least one guide of the second instrument can guide a surgical instrument in making a cut on the tibia having a desired slope relative to at least one of a biomechanical and an anatomical axis.

Another embodiment is a method for testing at least one of ligament balancing and ligament tension of a joint that includes: inserting a first template having a first surface onto a first joint surface, the first surface substantially conforming to the first joint surface; and inserting a second template onto the first joint surface, the second template having a first surface that conforms with, and is substantially a negative of, the first joint surface, the second template having a thickness that varies from the first template.

Other embodiments can include one or more of the following. The method can further include selecting one of the first and second templates based on at least one of ligament balancing and ligament tension. The method can also include attaching a third template to the selected template, the third template, including at least one guide for guiding a surgical instrument; positioning the first surface of the selected template onto the first joint surface; and guiding the surgical instrument using the at least one guide. The joint can be one of a knee joint, a hip joint, a shoulder joint, an elbow joint, a wrist joint, a finger joint, a toe joint, and an ankle joint.

Another embodiment is a system for articular repair that includes first and second templates having a first surface that conforms with, and substantially is a negative of, at least a portion of a distal femur. It also includes a second template that has a third surface that conforms with, and is substantially a negative of, a portion of the distal femur. The second template can include at least one guide for guiding a surgical instrument in making a cut on the distal femur, and an attachment mechanism for attaching the second template to the first template.

Other embodiments can include one or more of the following. The first or second templates can include a guide for making a vertical femoral cut. The second surface can be at least one of substantially flat, substantially concave, substantially convex, and matched to one of the tibia and the femur. At least one other template can have a first surface that conforms with, and substantially is a negative of, the at least a portion of the distal femur. Each of the other templates can be capable of attaching to the second template. The first template and each of the other templates can vary in thickness. At least a portion of the first surface can substantially conform to at least one of uncut subchondral bone, uncut cartilage, and uncut bone of a distal femur. At least a portion of the second surface can substantially conform to at least one of uncut subchondral bone, uncut cartilage, and uncut bone of a distal femur. At least a portion of the third surface can substantially conform to at least one of uncut subchondral bone, uncut cartilage, and uncut bone of a tibia. The attachment mechanism can include at least one of a snapfit, dovetail and a cross-pin. The attachment mechanism can allow for rotation relative to one of an anatomical and a biomechanical axis.

Another embodiment is a system for articular repair that includes a first template having a first surface and a second surface, the first surface substantially conforming to at least a portion of the distal femur. The first template includes a medial edge that corresponds to a predetermined location for a vertical femoral or tibial cut.

Other embodiments can have one or more of the following. A second template can have a third surface substantially conforming to at least a portion of the distal femur or tibial plateau. The second template can include at least one guide for guiding a surgical instrument. There can also be an attachment mechanism for attaching the second template to the first template. The first template can include a guide for guiding a surgical instrument. The medial edge can be adapted as a guide for making a vertical tibial or femoral cut. At least one other template can have a first surface and a second surface. The first surface can substantially conform to at least a portion of the tibial plateau. The first template and each of the other templates can vary in thickness. At least a portion of the first surface can substantially conforms to at least one of uncut subchondral bone, uncut cartilage, and uncut bone.

Some embodiments can be used for a partial joint replacement, a total joint replacement, a partial joint resurfacing and a total joint resurfacing. Templates can vary in thickness or curvatures or can be made available in multiple different thicknesses or curvatures. The thickness of the other template can be selected to improve or optimize the position of a bone cut for ligament balancing.

BRIEF DESCRIPTION OF THE DRAWINGS

The foregoing features of the invention will be more readily understood by reference to the following detailed description, taken with reference to the accompanying drawings, in which.

DETAILED DESCRIPTION OF THE INVENTION

Figure 1A:
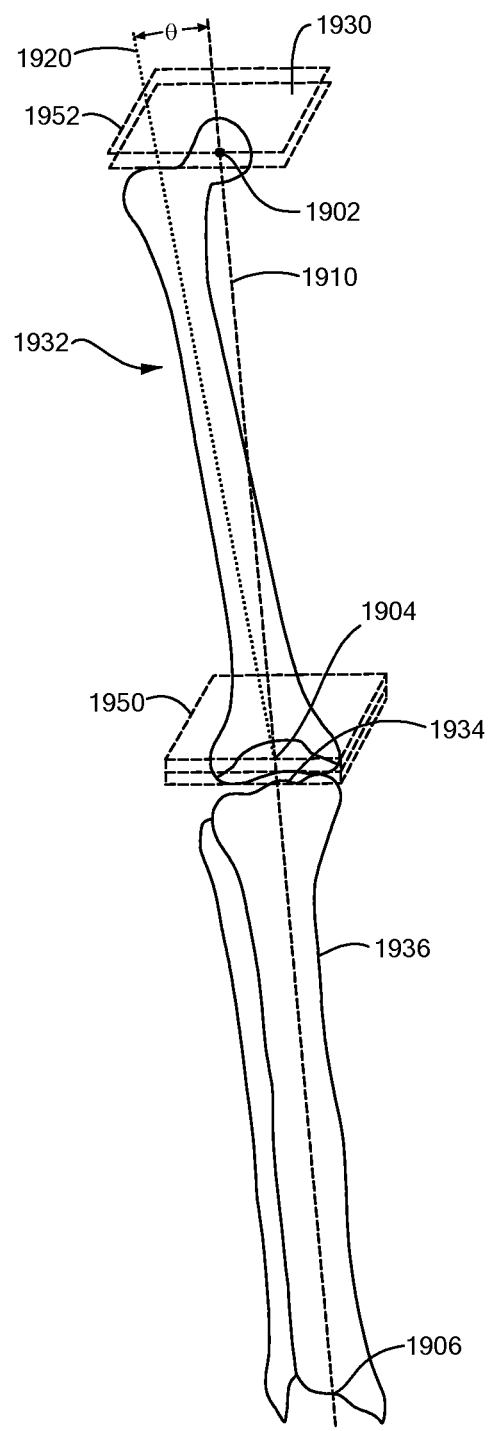
FIG. 1A illustrates a femur, tibia and fibula along with the mechanical and anatomic axes.

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

3D guidance surgical tools, referred to herein as a 3D guidance surgical templates, that may be used for surgical assistance may include, without limitation, using templates, jigs and/or molds, including 3D guidance molds. It is to be understood that the terms "template," "jig," "mold," "3D guidance mold," and "3D guidance template," shall be used interchangeably within the detailed description and appended claims to describe the tool unless the context indicates otherwise.

3D guidance surgical tools that may be used may include guide apertures. It is to be understood that the term guide aperture shall be used interchangeably within the detailed description and appended claims to describe both guide surface and guide elements.

As will be appreciated by those of skill in the art, the practice of the present invention employs, unless otherwise indicated, conventional methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. Such techniques are explained fully in the literature and need not be described herein. See, e.g., X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher. See also, The Essential Physics of Medical Imaging ($2^{nd}$ Ed.), Jerrold T. Bushberg, et al.

A. The Joint Replacement Procedure

The present invention may be applied to all joints, such as, without limitation, the knee, hip, shoulder, elbow, wrist, finger, toe, and ankle. Illustratively, the knee and hip joint procedures are discussed below, so as to teach the concept of the design as it would then apply to other joints in the body.

All of the embodiments described herein are applicable partial joint replacement, total joint replacement, and hemiarthroplasty. The embodiments may be combined with standard instrumentation known in the art as well as surgical techniques and robotics known in the art.

i. Knee Joint

Performing a total knee arthroplasty is a complicated procedure. In replacing the knee with an artificial knee, it is important to get the anatomical and mechanical axes of the lower extremity aligned correctly to ensure optimal functioning of the implanted knee.

As shown in FIG. 1A, the center of the hip 1902 (located at the head 1930 of the femur 1932), the center of the knee 1904 (located at the notch where the intercondular tubercle 1934 of the tibia 1936 meet the femur) and ankle 1906 lie approximately in a straight line 1910 which defines the mechanical axis of the lower extremity. The anatomic axis 1920 aligns 5-7° offset θ from the mechanical axis in the valgus, or outward, direction.

The long axis of the tibia 1936 is collinear with the mechanical axis of the lower extremity 1910. From a three-dimensional perspective, the lower extremity of the body ideally functions within a single plane known as the median anterior-posterior plane (MAP-plane) throughout the flexion-extension arc. In order to accomplish this, the femoral head 1930, the mechanical axis of the femur, the patellar groove, the intercondylar notch, the patellar articular crest, the tibia and the ankle remain within the MAP-plane during the flexion-extension movement. During movement, the tibia rotates as the knee flexes and extends in the epicondylar axis which is perpendicular to the MAP-plane.

A variety of image slices can be taken at each individual joint, e.g., the knee joint 1950-1950$_n$, and the hip joint 1952-1950$_n$. These image slices can be used as described above in Section I along with an image of the full leg to ascertain the axis.

With disease and malfunction of the knee, alignment of the anatomic axis is altered. Performing a total knee arthroplasty is one solution for correcting a diseased knee. Implanting a total knee joint, such as the PFC Sigma RP Knee System by Johnson & Johnson, requires that a series of resections be made to the surfaces forming the knee joint in order to facilitate installation of the artificial knee. The resections should be made to enable the installed artificial knee to achieve flexion-extension movement within the MAP-plane and to optimize the patient's anatomical and mechanical axis of the lower extremity.

First, the tibia 1930 is resected to create a flat surface to accept the tibial component of the implant. In most cases, the tibial surface is resected perpendicular to the long axis of the tibia in the coronal plane, but is typically sloped 4-7° posteriorly in the sagittal plane to match the normal slope of the tibia. As will be appreciated by those of skill in the art, the sagittal slope can be 0° where the device to be implanted does not require a sloped tibial cut. The resection line 1958 is perpendicular to the mechanical axis 1910, but the angle between the resection line and the surface plane of the plateau 1960 varies depending on the amount of damage to the knee.

Figure 1B:
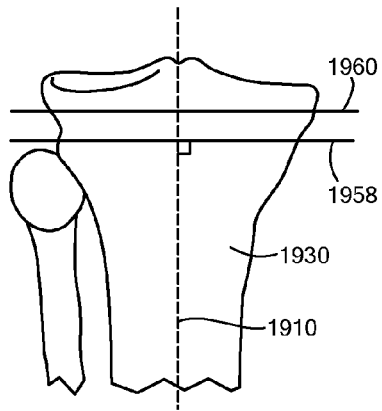
FIGS. 1B-E illustrate the tibia with the anatomic and mechanical axis used to create a cutting plane along with a cut femur and tibia.
Figure 1C:
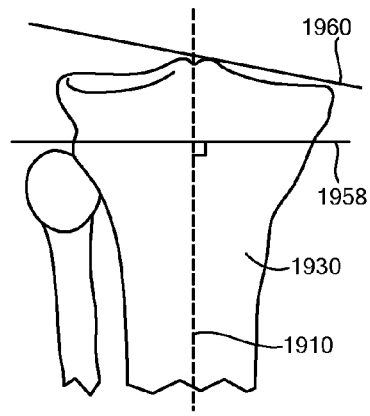
Figure 1D:
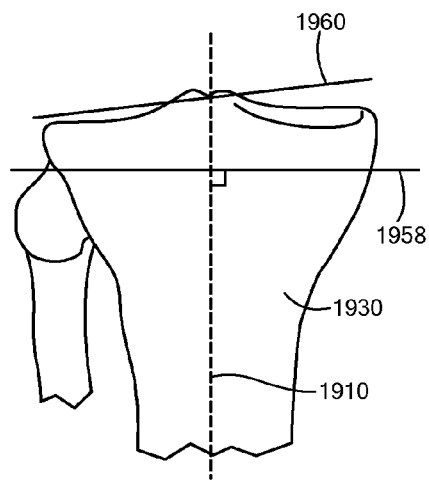

FIGS. 1B-D illustrate an anterior view of a resection of an anatomically normal tibial component, a tibial component in a varus knee, and a tibial component in a valgus knee, respectively. In each figure, the mechanical axis 1910 extends vertically through the bone and the resection line 1958 is perpendicular to the mechanical axis 1910 in the coronal plane, varying from the surface line formed by the joint depending on the amount of damage to the joint. FIG. 1B illustrates a normal knee wherein the line corresponding to the surface of the joint 1960 is parallel to the resection line 1958. FIG. 1C illustrates a varus knee wherein the line corresponding to the surface of the joint 1960 is not parallel to the resection line 1958. FIG. 1D illustrates a valgus knee wherein the line corresponding to the surface of the joint 1960 is not parallel to the resection line 1958.

Once the tibial surface has been prepared, the surgeon turns to preparing the femoral condyle.

The plateau of the femur 1970 is resected to provide flat surfaces that communicate with the interior of the femoral prosthesis. The cuts made to the femur are based on the overall height of the gap to be created between the tibia and the femur. Typically, a 20 mm gap is desirable to provide the implanted prosthesis adequate room to achieve full range of motion. The bone is resected at a 5-7° angle valgus to the mechanical axis of the femur. Resected surface 1972 forms a flat plane with an angular relationship to adjoining surfaces 1974, 1976. The angle θ', θ" between the surfaces 1972-1974, and 1972-1976 varies according to the design of the implant.

ii. Hip Joint

Figure 1E:
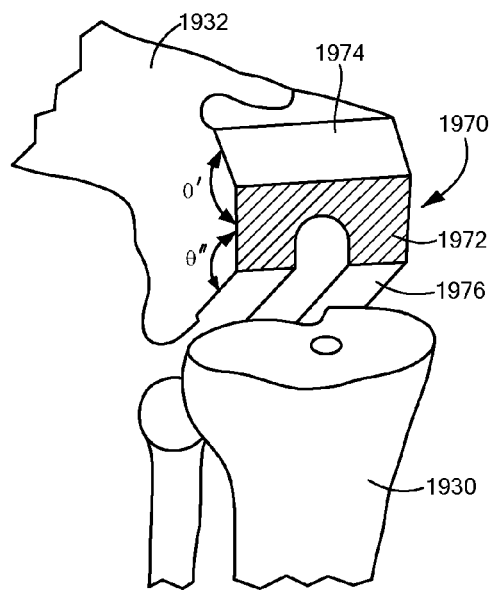
Figure 1F:
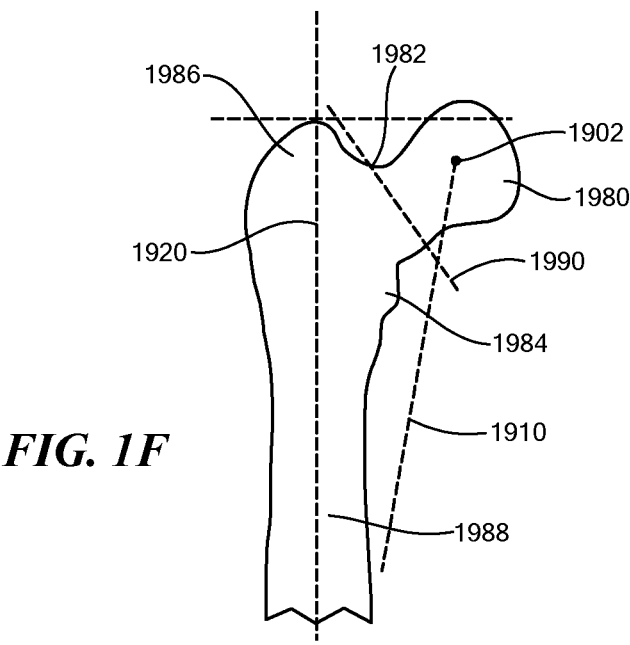
FIG. 1F illustrates the proximal end of the femur including the head of the femur.

As illustrated in FIG. 1F, the external geometry of the proximal femur includes the head 1980, the neck 1982, the lesser trochanter 1984, the greater trochanter 1986 and the proximal femoral diaphysis. The relative positions of the trochanters 1984, 1986, the femoral head center 1902 and the femoral shaft 1988 are correlated with the inclination of the neck-shaft angle. The mechanical axis 1910 and anatomic axis 1920 are also shown. Assessment of these relationships can change the reaming direction to achieve neutral alignment of the prosthesis with the femoral canal.

Using anteroposterior and lateral radiographs, measurements are made of the proximal and distal geometry to determine the size and optimal design of the implant.

Typically, after obtaining surgical access to the hip joint, the femoral neck 1982 is resected, e.g. along the line 1990. Once the neck is resected, the medullary canal is reamed. Reaming can be accomplished, for example, with a conical or straight reamer, or a flexible reamer. The depth of reaming is dictated by the specific design of the implant. Once the canal has been reamed, the proximal reamer is prepared by serial rasping, with the rasp directed down into the canal.

B. Surgical Tools

Surgical assistance can be provided by using a device, referred to also herein as a surgical tool or template, applied to the outer surface of the articular cartilage or the bone, including the subchondral bone, in order to match the alignment of the articular repair system and the recipient site or the joint. The template may be round, circular, oval, ellipsoid, curved or irregular in shape. The shape can be selected or adjusted to match or enclose an area of diseased cartilage or an area slightly larger than the area of diseased cartilage or substantially larger than the diseased cartilage. The area can encompass the entire articular surface or the weight bearing surface. Such devices are typically preferred when replacement of a majority or an entire articular surface is contemplated.

The template may include at least one guide for guiding a surgical instrument. The at least one guide may direct the surgical instrument in at least one of a cut, a milling, and a drilling. The at least one guide may be, without limitation, a drill hole, a cut planes, a saw plane and the like. The guide may be oriented in a predefined location relative to, without limitation, the contact surface of the template with the articular cartilage or bone, and may be adapted in shape, size or orientation to an implant shape.

Typically, a position of the guide will be chosen that will result in an anatomically desirable cut plane, drill hole, or general instrument orientation for subsequent placement of an articular repair system or for facilitating placement of the articular repair system. Moreover, the template may be designed so that the depth of the drill, reamer or other surgical instrument can be controlled, e.g., the drill cannot go any deeper into the tissue than defined by the device, and the size of the hole in the block can be designed to essentially match the size of the implant. Information about other joints or axis and alignment information of a joint or extremity can be included when selecting the position of these slots or holes. Alternatively, the openings in the template may be made larger than needed to accommodate these instruments. The template may also be configured to conform to the articular shape. The apertures, or openings, provided can be wide enough to allow for varying the position or angle of the surgical instrument, e.g., reamers, saws, drills, curettes and other surgical instruments. An instrument guide, typically comprised of a relatively hard material, can then be applied to the device. The device helps orient the instrument guide relative to the three-dimensional anatomy of the joint.

The template may be a mold that can be made of a plastic or polymer. The template may be produced by rapid prototyping technology, in which successive layers of plastic are laid down, as know in the art. In other embodiments, the template or portions of the template can be made of metal. The template can be milled or made using laser based manufacturing techniques.

The template may be casted using rapid prototyping and, for example, lost wax technique. It may also be milled. For example, a preformed template with a generic shape can be used at the outset, which can then be milled to the patient specific dimensions. The milling may only occur on one surface of the template, preferably the surface that faces the articular surface. Milling and rapid prototyping techniques may be combined.

Curable materials may be used which can be poured into forms that are, for example, generated using rapid prototyping. For example, liquid metal may be used. Cured materials may optionally be milled or the surface can be further refined using other techniques.

Metal inserts may be applied to plastic components. For example, a plastic mold may have at least one guide aperture to accept a reaming device or a saw. A metal insert may be used to provide a hard wall to accept the reamer or saw. Using this or similar designs can be useful to avoid the accumulation of plastic or other debris in the joint when the saw or other surgical instruments may get in contact with the mold. Other hard materials can be used to serve as inserts. These can also include, for example, hard plastics or ceramics.

In another embodiment, the template does not have metallic inserts to accept a reaming device or saw. The metal inserts or guides may be part of an attached device that is typically in contact with the template. A metallic drill guide or a metallic saw guide may thus, for example, have metallic or hard extenders that reach through the mold thereby, for example, also stabilizing any devices applied to the mold against the physical body of the mold.

One or more templates can be used during the surgery. For example, in the hip, a template can be initially applied to the proximal femur that closely approximates the 3D anatomy prior to the resection of the femoral head. The template can include an opening to accommodate a saw. The opening is positioned to achieve an optimally placed surgical cut for subsequent reaming and placement of the prosthesis. A second template can then be applied to the proximal femur after the surgical cut has been made. The second template can be useful for guiding the direction of a reamer prior to placement of the prosthesis. As can be seen in this, as well as in other examples, templates can be made for joints prior to any surgical intervention. However, it is also possible to make templates that are designed to fit to a bone or portions of a joint after the surgeon has already performed selected surgical procedures, such as cutting, reaming, drilling, etc. The template can account for the shape of the bone or the joint resulting from these procedures.

Upon imaging, a physical template of a joint, such as a knee joint, or hip joint, or ankle joint or shoulder joint is generated, in accordance with an embodiment of the invention. The template can be used to perform image guided surgical procedures such as partial or complete joint replacement, articular resurfacing, or ligament repair. The template may include reference points or opening or apertures for surgical instruments such as drills, saws, burrs and the like.

In order to derive the preferred orientation of drill holes, cut planes, saw planes and the like, openings or receptacles in said template or attachments will be adjusted to account for at least one axis. The axis can be anatomic or biomechanical, for example, for a knee joint, a hip joint, an ankle joint, a shoulder joint or an elbow joint.

In one embodiment, only a single axis is used for placing and optimizing such drill holes, saw planes, cut planes, and or other surgical interventions. This axis may be, for example, an anatomical or biomechanical axis. In a preferred embodiment, a combination of axis and/or planes can be used for optimizing the placement of the drill holes, saw planes, cut planes or other surgical interventions. For example, two axes (e.g., one anatomical and one biomechanical) can be factored into the position, shape or orientation of the 3D guided template and related attachments or linkages. For example, two axes, (e.g., one anatomical and biomechanical) and one plane (e.g., the top plane defined by the tibial plateau), can be used. Alternatively, two or more planes can be used (e.g., a coronal and a sagittal plane), as defined by the image or by the patients anatomy.

Angle and distance measurements and surface topography measurements may be performed in these one or more, preferably two or more, preferably three or more multiple planes, as necessary. These angle measurements can, for example, yield information on varus or valgus deformity, flexion or extension deficit, hyper or hypo-flexion or hyper- or hypo-extension, abduction, adduction, internal or external rotation deficit, or hyper- or hypo-abduction, hyper- or hypo-adduction, hyper- or hypo-internal or external rotation.

Single or multi-axis line or plane measurements can then be utilized to determine preferred angles of correction, e.g., by adjusting surgical cut or saw planes or other surgical interventions. Typically, two axis corrections will be preferred over a single axis correction, a two plane correction will be preferred over a single plane correction and so forth.

In accordance with another embodiment of the invention, more than one drilling, cut, boring and/or reaming or other surgical intervention is performed for a particular treatment such as the placement of a joint resurfacing or replacing implant, or components thereof. These two or more surgical interventions (e.g., drilling, cutting, reaming, sawing) are made in relationship to a biomechanical axis, and/or an anatomical axis and/or an implant axis. The 3D guidance template or attachments or linkages thereto include two or more openings, guides, apertures or reference planes to make at least two or more drillings, reamings, borings, sawings or cuts in relationship to a biomechanical axis, an anatomical axis, an implant axis or other axis derived therefrom or related thereto.

While in simple embodiments it is possible that only a single cut or drilling will be made in relationship to a biomechanical axis, an anatomical axis, an implant axis and/or an axis related thereto, in most meaningful implementations, two or more drillings, borings, reamings, cutting and/or sawings will be performed or combinations thereof in relationship to a biomechanical, anatomical and/or implant axis.

Figure 2:
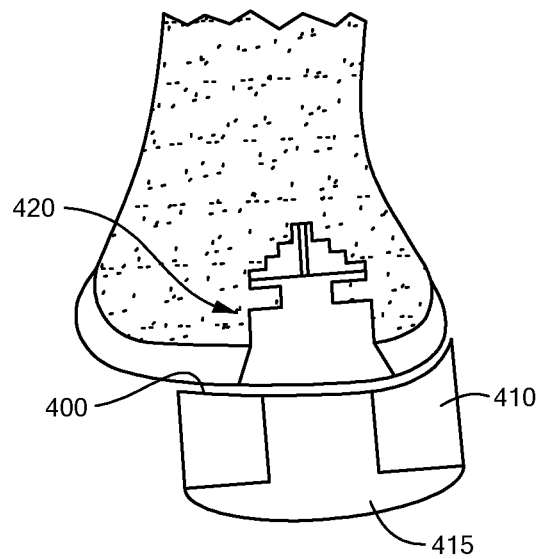
FIG. 2 shows an example of a surgical tool having one surface matching the geometry of an articular surface of the joint, in accordance with one embodiment of the invention. Also shown is an aperture in the tool capable of controlling drill depth and width of the hole and allowing implantation of an insertion of implant having a press-fit design.

FIG. 2 shows an example of a surgical tool 410 having one surface 400 matching the geometry of an articular surface of the joint. Also shown is an aperture 415 in the tool 410 capable of controlling drill depth and width of the hole and allowing implantation or insertion of implant 420 having a press-fit design.

Figure 3:
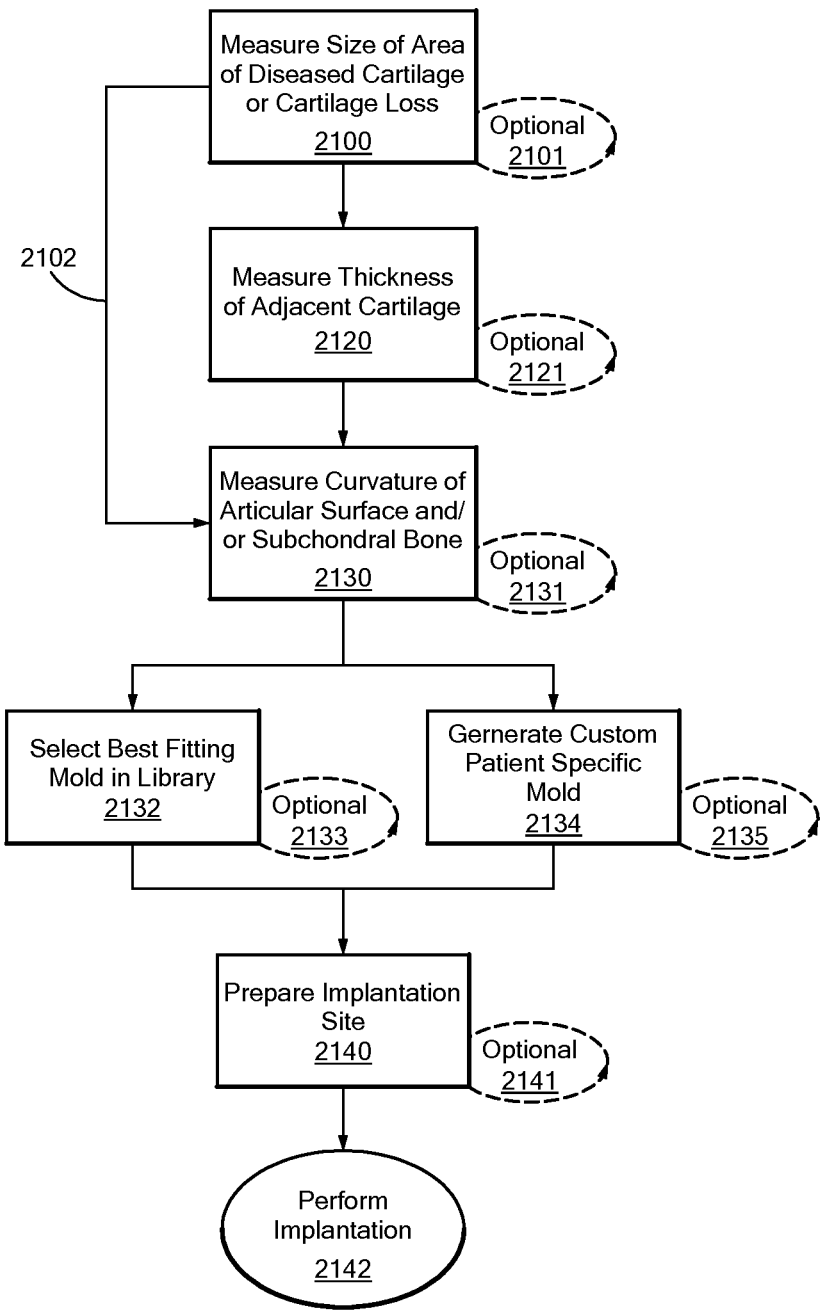
FIG. 3 is a flow chart depicting various methods of the invention used to create a mold for preparing a patient's joint for arthroscopic surgery, in accordance with one embodiment of the invention.

FIG. 3 is a flow chart illustrating the steps involved in designing a template for use in preparing a joint surface. Illustratively, the template is, without limitation, a mold. Optionally, the first step can be to measure the size of the area of the diseased cartilage or cartilage loss 2100, Once the size of the cartilage loss has been measured, the user can measure the thickness of the adjacent cartilage 2120, prior to measuring the curvature of the articular surface and/or the subchondral bone 2130. Alternatively, the user can skip the step of measuring the thickness of the adjacent cartilage 2102. Once an understanding and determination of the shape of the subchondral bone is determined, either a mold can be selected from a library of molds 3132 or a patient specific mold can be generated 2134. In either event, the implantation site is then prepared 2140 and implantation is performed 2142. Any of these steps can be repeated by the optional repeat steps 2101, 2121, 2131, 2133, 2135, 2141.

Instead of a mold, it is to be understood that the surgical tool may be made in a variety of ways, including, without limitation, machining and rapid prototyping. Rapid prototyping is a technique for fabricating a three-dimensional object from a computer model of the object. Typically, a special printer is used to fabricate the prototype from a plurality of two-dimensional layers. Computer software sections the representations of the object into a plurality of distinct two-dimensional layers and then a three-dimensional printer fabricates a layer of material for each layer sectioned by the software. Together the various fabricated layers form the desired prototype. More information about rapid prototyping techniques is available in US Patent Publication No 2002/0079601A1 to Russell et al., published Jun. 27, 2002, which is incorporated herein by reference. An advantage to using rapid prototyping is that it enables the use of free form fabrication techniques that use toxic or potent compounds safely. These compounds can be safely incorporated in an excipient envelope, which reduces worker exposure A variety of techniques can be used to derive the shape of the template, as described above. For example, a few selected CT slices through the hip joint, along with a full spiral CT through the knee joint and a few selected slices through the ankle joint can be used to help define the axes if surgery is contemplated of the knee joint. Once the axes are defined, the shape of the subchondral bone can be derived, followed by applying standardized cartilage loss.

Methodologies for stabilizing the 3D guidance templates will now be described. The 3D guide template may be stabilized using multiple surgical tools such as, without limitation: K-wires; a drill bit anchored into the bone and left within the template to stabilize it against the bone; one or more convexities or cavities on the surface facing the cartilage; bone stabilization against intra/extra articular surfaces, optionally with extenders, for example, from an articular surface onto an extra-articular surface; and/or stabilization against newly placed cuts or other surgical interventions.

Specific anatomic landmarks may be selected in the design and make of the 3D guide template in order to further optimize the anatomic stabilization. For example, a 3D guidance template may be designed to cover portions or all off an osteophyte or bone spur in order to enhance anchoring of the 3D guide template against the underlying articular anatomy. The 3D guidance template may be designed to the shape of a trochlear or intercondylar notch and can encompass multiple anatomic areas such as a trochlea, a medial and a lateral femoral condyle at the same time. In the tibia, a 3D guide template may be designed to encompass a medial and lateral tibial plateau at the same time and it can optionally include the tibial spine for optimized stabilization and cross-referencing. In a hip, the fovea capitis may be utilized in order to stabilize a 3D guide template. Optionally, the surgeon may elect to resect the ligamentum capitis femoris in order to improve the stabilization. Also in the hip, an acetabular mold can be designed to extend into the region of the tri-radiate cartilage, the medial, lateral, superior, inferior, anterior and posterior acetabular wall or ring. By having these extensions and additional features for stabilization, a more reproducible position of the 3D template can be achieved with resulted improvement in accuracy of the surgical procedure. Typically, a template with more than one convexity or concavity or multiple convexities or concavities will provide better cross-referencing in the anatomic surface and higher accuracy and higher stabilization than compared to a mold that has only few surface features such as a singular convexity. Thus, in order to improve the implementation and intraoperative accuracy, careful surgical planning and preoperative planning is desired, that encompasses preferably more than one convexity, more preferred more than two convexities and even more preferred more than three convexities, or that encompasses more than one concavity, more preferred more than two concavities or even more preferred more than three concavities on an articular surface or adjoined surface, including bone and cartilage outside the weight-bearing surface.

In an even more preferred embodiment, more than one convexity and concavity, more preferred more than two convexities and concavities and even more preferred more then three convexities and concavities are included in the surface of the mold in order to optimize the interoperative cross-referencing and in order to stabilize the mold prior to any surgical intervention.

Turning now to a particular 3D surgical template configuration for a specific joint application (knee joint), which is intended to teach the concept of the design as it would then apply to other joints in the body:

When a total knee arthroplasty is contemplated, the patient can undergo an imaging test, that will demonstrate the articular anatomy of a knee joint, e.g. width of the femoral condyles, the tibial plateau etc. Additionally, other joints can be included in the imaging test thereby yielding information on femoral and tibial axes, deformities such as varus and valgus and other articular alignment. The imaging test may be, without limitation, an x-ray image, preferably in standing, load-bearing position, a CT or spiral CT scan or an MRI scan or combinations thereof. A spiral CT scan may be advantageous over a standard CT scan due to its improved spatial resolution in z-direction in addition to x and y resolution. The articular surface and shape as well as alignment information generated with the imaging test can be used to shape the surgical assistance device, to select the surgical assistance device from a library of different devices with pre-made shapes and sizes, or can be entered into the surgical assistance device and can be used to define the preferred location and orientation of saw guides or drill holes or guides for reaming devices or other surgical instruments. Intraoperatively, the surgical assistance device is applied to the tibial plateau and subsequently the femoral condyle(s) by matching its surface with the articular surface or by attaching it to anatomic reference points on the bone or cartilage. The surgeon can then introduce a reamer or saw through the guides and prepare the joint for the implantation. By cutting the cartilage and bone along anatomically defined planes, a more reproducible placement of the implant can be achieved. This can ultimately result in improved postoperative results by optimizing biomechanical stresses applied to the implant and surrounding bone for the patient's anatomy and by minimizing axis malalignment of the implant. In addition, the surgical assistance device can greatly reduce the number of surgical instruments needed for total or unicompartmental knee arthroplasty. Thus, the use of one or more surgical assistance devices can help make joint arthroplasty more accurate, improve postoperative results, improve long-term implant survival, reduce cost by reducing the number of surgical instruments used. Moreover, the use of one or more surgical assistance device can help lower the technical difficulty of the procedure and can help decrease operating room ("OR") times.

Thus, surgical tools described herein can also be designed and used to control drill alignment, depth and width, for example when preparing a site to receive an implant. For example, the tools described herein, which typically conform to the joint surface, can provide for improved drill alignment and more accurate placement of any implant. An anatomically correct tool can be constructed by a number of methods and can be made of any material, preferably a substantially translucent and/or transparent material such as plastic, Lucite, silastic, SLA or the like, and typically is a block-like shape prior to molding.

Figure 4A:
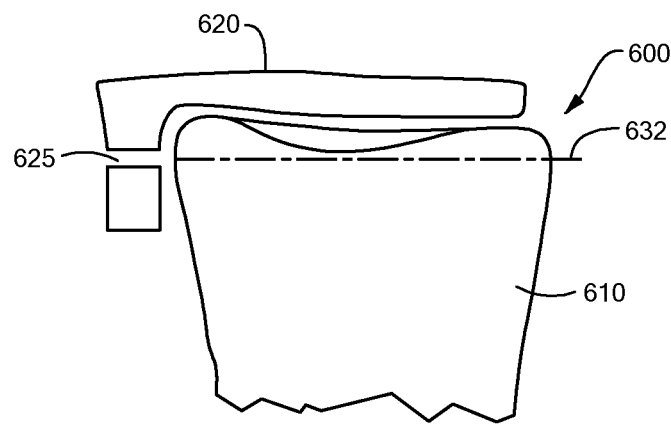
FIG. 4A depicts, in cross-section, an example of a surgical tool containing an aperture through which a surgical drill or saw can fit, in accordance with one embodiment of the invention. The aperture guides the drill or saw to make the proper hole or cut in the underlying bone. Dotted lines represent where the cut corresponding to the aperture will be made in bone.
Figure 4B:
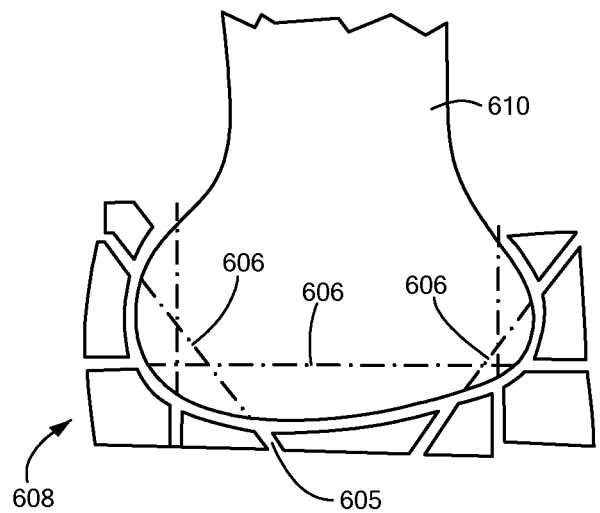
FIG. 4B depicts, in cross-section, an example of a surgical tool containing apertures through which a surgical drill or saw can fit and which guide the drill or saw to make cuts or holes in the bone, in accordance with one embodiment of the invention. Dotted lines represent where the cuts corresponding to the apertures will be made in bone.

FIG. 4A depicts, in cross-section, an example of a template 600 for use on the tibial surface having an upper surface 620. The template 600 includes an aperture 625 through which a surgical drill or saw can fit. The aperture guides the drill or saw to make the proper hole or cut in the underlying bone 610 as illustrated in FIGS. 1B-D. In various embodiments, the template may include a guide aperture, a reaming aperture, a drill aperture and a cut plane for guiding a surgical tool. Dotted lines 632 illustrate where the cut corresponding to the aperture will be made in bone. FIG. 4B depicts, a template 608 suitable for use on the femur. As can be appreciated from this perspective, additional apertures are provided to enable additional cuts to the bone surface. The apertures 605 enable cuts 606 to the surface of the femur. The resulting shape of the femur corresponds to the shape of the interior surface of the femoral implant, typically as shown in FIG. 1E. Additional shapes can be achieved, if desired, by changing the size, orientation and placement of the apertures. Such changes would be desired where, for example, the interior shape of the femoral component of the implant requires a different shape of the prepared femur surface.

Turning now to FIG. 5, a variety of illustrations are provided showing a template that includes a tibial cutting block and mold system. FIG. 5A illustrates the tibial cutting block 2300 in conjunction with a tibia 2302 that has not been resected. In this depiction, the cutting block 2300 consists of at least two pieces. The first piece is a patient specific interior piece 2310 or mold that is designed on its inferior surface 2312 to mate, or substantially mate, with the existing geography of the patient's tibia 2302. The superior surface 2314 and side surfaces 2316 of the first piece 2310 are configured to mate within the interior of an exterior piece 2320. The reusable exterior piece 2320 fits over the interior piece 2310. The system can be configured to hold the mold onto the bone.

The reusable exterior piece has a superior surface 2322 and an inferior surface 2324 that mates with the first piece 2310. The reusable exterior piece 2320 includes cutting guides 2328, to assist the surgeon in performing the tibial surface cut described above. As shown herein a plurality of cutting guides can be provided to provide the surgeon a variety of locations to choose from in making the tibial cut. If necessary, additional spacers can be provided that fit between the first patient configured, or molded, piece 2310 and the second reusable exterior piece, or cutting block, 2320.

Clearly, the mold may be a single component or multiple components. In a preferred embodiment, one or more components are patient specific while other components such as spacers or connectors to surgical instruments are generic. In one embodiment, the mold can rest on portions of the joint on the articular surface or external to the articular surface. Other surgical tools then may connect to the mold. For example, a standard surgical cut block as described for standard implants, for example in the knee the J&J PFC Sigma system, the Zimmer Nexgen system or the Stryker Duracon system, can be connected or placed on the mold. In this manner, the patient specific component can be minimized and can be made compatible with standard surgical instruments.

The mold may include receptacles for standard surgical instruments including alignment tools or guides. For example, a tibial mold for use in knee surgery may have an extender or a receptacle or an opening to receive a tibial alignment rod. In this manner, the position of the mold can be checked against the standard alignment tools and methods. Moreover, the combined use of molds and standard alignment tools including also surgical navigation techniques can help improve the accuracy of or optimize component placement in joint arthroplasty, such as hip or knee arthroplasty. For example, the mold can help define the depth of a horizontal tibial cut for placement of a tibial component. A tibial alignment guide, for example an extramedullary or intramedullary alignment guide, used in conjunction with a tibial mold can help find the optimal anteroposterior angulation, posterior slope, tibial slant, or varus-valgus angle of the tibial cut. The mold may be designed to work in conjunction with traditional alignment tools known in the art.

The template may include markers, e.g. optoelectronic or radiofrequency, for surgical navigation. The template may have receptacles to which such markers can be attached, either directly or via a linking member.

The templates can be used in combination with a surgical navigation system. They can be used to register the bones associated with a joint into the coordinate system of the surgical navigation system. For example, if a mold for a joint surface includes tracking markers for surgical navigation, the exact position and orientation of the bone can be detected by the surgical navigation system after placement of the mold in its unique position. This helps to avoid the time-consuming need to acquire the coordinates of tens to hundreds of points on the joint surface for registration.

Referring back to FIG. 5, the variable nature of the interior piece facilitates obtaining the most accurate cut despite the level of disease of the joint because it positions the exterior piece 2320 such that it can achieve a cut that is perpendicular to the mechanical axis. Either the interior piece 2310 or the exterior piece 2320 can be formed out of any of the materials discussed above in Section II, or any other suitable material. Additionally, a person of skill in the art will appreciate that the invention is not limited to the two piece configuration described herein. The reusable exterior piece 2320 and the patient specific interior piece 2310 can be a single piece that is either patient specific (where manufacturing costs of materials support such a product) or is reusable based on a library of substantially defect conforming shapes developed in response to known or common tibial surface sizes and defects.

The interior piece 2310 is typically molded to the tibia including the subchondral bone and/or the cartilage. The surgeon will typically remove any residual meniscal tissue prior to applying the mold. Optionally, the interior surface 2312 of the mold can include shape information of portions or all of the menisci.

Figure 5A:
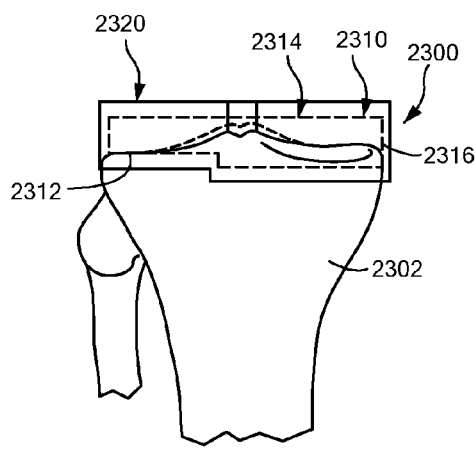
FIGS. 5A-R illustrate tibial cutting blocks and molds used to create a surface perpendicular to the anatomic axis for receiving the tibial portion of a knee implant, in accordance with various embodiments of the invention.
Figure 5B:
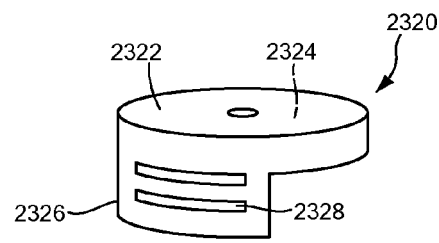
Figure 5C:
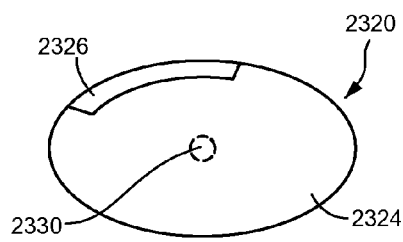
Figure 5D:
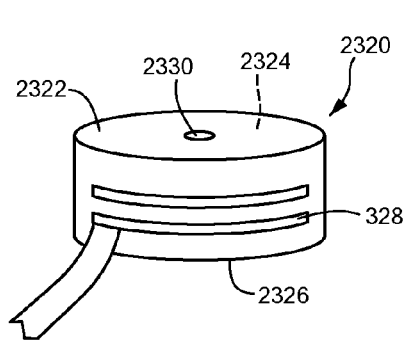

Turning now to FIG. 5B-D, a variety of views of the removable exterior piece 2320. The top surface 2322 of the exterior piece can be relatively flat. The lower surface 2324 which abuts the interior piece conforms to the shape of the upper surface of the interior piece. In this illustration the upper surface of the interior piece is flat, therefore the lower surface 2324 of the reusable exterior surface is also flat to provide an optimal mating surface.

A guide plate 2326 is provided that extends along the side of at least a portion of the exterior piece 2320. The guide plate 2326 provides one or more slots or guides 2328 through which a saw blade can be inserted to achieve the cut desired of the tibial surface. Additionally, the slot, or guide, can be configured so that the saw blade cuts at a line perpendicular to the mechanical axis, or so that it cuts at a line that is perpendicular to the mechanical axis, but has a 4-7° slope in the sagittal plane to match the normal slope of the tibia.

Optionally, a central bore 2330 can be provided that, for example, enables a drill to ream a hole into the bone for the stem of the tibial component of the knee implant.

Figure 5E:
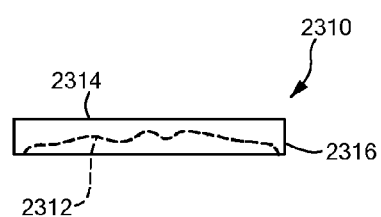
Figure 5F:
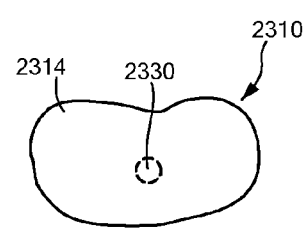

FIGS. 5E-H illustrate the interior, patient specific, piece 2310 from a variety of perspectives. FIG. 5E shows a side view of the piece showing the uniform superior surface 2314 and the uniform side surfaces 2316 along with the irregular inferior surface 2316. The inferior surface mates with the irregular surface of the tibia 2302. FIG. 5F illustrates a superior view of the interior, patient, specific piece of the mold 2310. Optionally having an aperture 2330. FIG. 5G illustrates an inferior view of the interior patient specific mold piece 2310 further illustrating the irregular surface which includes convex and concave portions to the surface, as necessary to achieve optimal mating with the surface of the tibia. FIG. 5H illustrates cross-sectional views of the interior patient specific mold piece 2310. As can be seen in the cross-sections, the surface of the interior surface changes along its length.

As is evident from the views shown in FIGS. 5B and D, the length of the guide plate 2326 can be such that it extends along all or part of the tibial plateau, e.g. where the guide plate 2326 is asymmetrically positioned as shown in FIG. 5B or symmetrical as in FIG. 3D. If total knee arthroplasty is contemplated, the length of the guide plate 2326 typically extends along all of the tibial plateau. If unicompartmental arthroplasty is contemplated, the length of the guide plate typically extends along the length of the compartment that the surgeon will operate on. Similarly, if total knee arthroplasty is contemplated, the length of the molded, interior piece 2310 typically extends along all of the tibial plateau; it can include one or both tibial spines. If unicompartmental arthroplasty is contemplated, the length of the molded interior piece typically extends along the length of the compartment that the surgeon will operate on; it can optionally include a tibial spine.

Turning now to FIG. 5I, an alternative embodiment is depicted of the aperture 2330. In this embodiment, the aperture features lateral protrusions to accommodate using a reamer or punch to create an opening in the bone that accepts a stem having flanges.

FIGS. 5J and M depict alternative embodiments of the invention designed to control the movement and rotation of the cutting block 2320 relative to the mold 2310. As shown in FIG. 5J a series of protrusions, illustrated as pegs 2340, are provided that extend from the superior surface of the mold. As will be appreciated by those of skill in the art, one or more pegs or protrusions can be used without departing from the scope of the invention. For purposes of illustration, two pegs have been shown in FIG. 5J. Depending on the control desired, the pegs 2340 are configured to fit within, for example, a curved slot 2342 that enables rotational adjustment as illustrated in FIG. 3K or within a recess 2344 that conforms in shape to the peg 2340 as shown in FIG. 5L. As will be appreciated by those of skill in the art, the recess 2344 can be sized to snugly encompass the peg or can be sized larger than the peg to allow limited lateral and rotational movement. The recess can be composed of a metal or other hard insert 544.

Figure 5M:
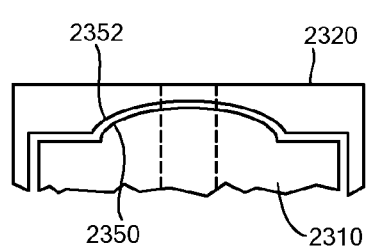

As illustrated in FIG. 5M the surface of the mold 2310 can be configured such that the upper surface forms a convex dome 2350 that fits within a concave well 2352 provided on the interior surface of the cutting block 2320. This configuration enables greater rotational movement about the mechanical axis while limiting lateral movement or translation.

Other embodiments and configurations could be used to achieve these results without departing from the scope of the invention.

As will be appreciated by those of skill in the art, more than two pieces can be used, where appropriate, to comprise the system. For example, the patient specific interior piece 2310 can be two pieces that are configured to form a single piece when placed on the tibia. Additionally, the exterior piece 2320 can be two components. The first component can have, for example, the cutting guide apertures 2328. After the resection using the cutting guide aperture 2328 is made, the exterior piece 2320 can be removed and a secondary exterior piece 2320' can be used which does not have the guide plate 2326 with the cutting guide apertures 2328, but has the aperture 2330 which facilitates boring into the tibial surface an aperture to receive a stem of the tibial component of the knee implant. Any of these designs could also feature the surface configurations shown in FIGS. 5J-M, if desired.

Figure 5N:
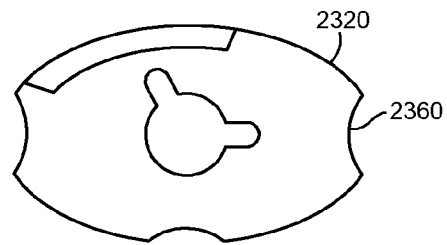

FIG. 5N illustrates an alternative design of the cutting block 2320 that provides additional structures 2360 to protect, for example, the cruciate ligaments, from being cut during the preparation of the tibial plateau. These additional structures can be in the form of indented guides 2360, as shown in FIG. 5N or other suitable structures.

Figure 5O:
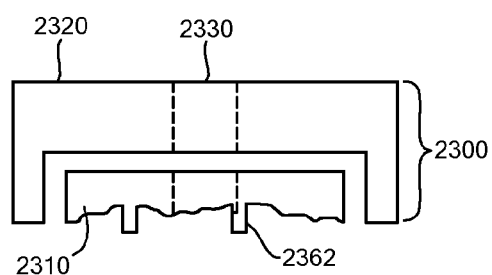

FIG. 5O illustrates a cross-section of a system having anchoring pegs 2362 on the surface of the interior piece 2310 that anchor the interior piece 2310 into the cartilage or meniscal area.

Figure 5P:
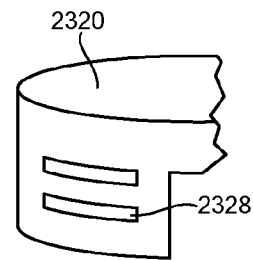
Figure 5Q:
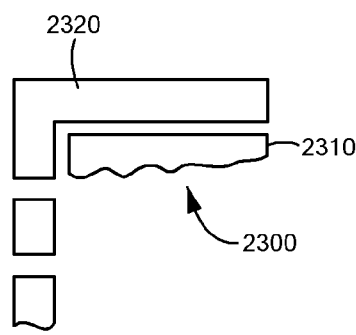

FIGS. 5P AND Q illustrate a device 2300 configured to cover half of a tibial plateau such that it is unicompartmental.

Figure 5R:
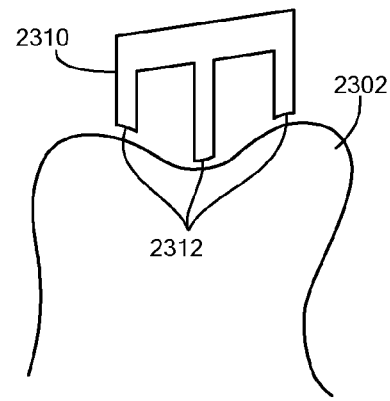

FIG. 5R illustrates an interior piece 2310 that has multiple contact surfaces 2312 with the tibial 2302, in accordance with one embodiment of the invention. As opposed to one large contact surface, the interior piece 2310 includes a plurality of smaller contact surfaces 2312. In various embodiments, the multiple contact surfaces 2312 are not on the sample plane and are at angles relative to each other to ensure proper positioning on the tibia 2302. Two or three contact surfaces 2312 may be required to ensure proper positioning. In various embodiments, only the contact surfaces 2312 of the interior piece may be molded, the molds attached to the rest of the template using methodologies known in the art, such as adhesives. The molds may be removably attached to the template. It is to be understood that multiple contact surfaces 2312 may be utilized in template embodiments that include one or a plurality of pieces.

Turning now to FIG. 6, a femoral template/mold system is depicted that facilitates preparing the surface of the femur such that the finally implanted femoral implant will achieve optimal mechanical and anatomical axis alignment.

Figure 6A:
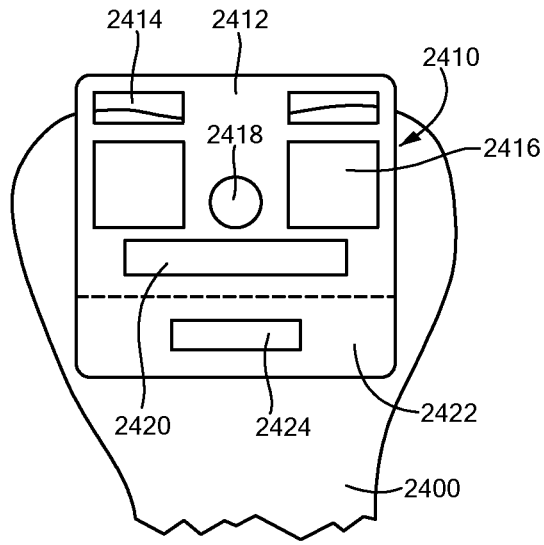
FIGS. 6A-O illustrate femur cutting blocks and molds used to create a surface for receiving the femoral portion of a knee implant, in accordance with various embodiments of the invention.

FIG. 6A illustrates the femur 2400 with a first portion 2410 of the mold placed thereon. In this depiction, the top surface of the mold 2412 is provided with a plurality of apertures. In this instance the apertures consist of a pair of rectangular apertures 2414, a pair of square apertures 2416, a central bore aperture 2418 and a long rectangular aperture 2420. The side surface 2422 of the first portion 2410 also has a rectangular aperture 2424. Each of the apertures is larger than the eventual cuts to be made on the femur so that, in the event the material the first portion of the mold is manufactured from a soft material, such as plastic, it will not be inadvertently cut during the joint surface preparation process. Additionally, the shapes can be adjusted, e.g., rectangular shapes made trapezoidal, to give a greater flexibility to the cut length along one area, without increasing flexibility in another area. As will be appreciated by those of skill in the art, other shapes for the apertures, or orifices, can be changed without departing from the scope of the invention.

Figure 6B:
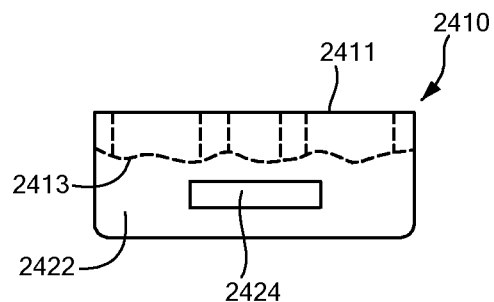
FIG. 6P illustrates an axis defined by the center of the tibial plateau and the center of the distal tibia.
FIG. 6Q shows an axis defining the center of the tibial plateau to the femoral head.
FIGS. 6R and 6S show isometric views of a femoral template and a tibial template, respectively, in accordance with various embodiments of the invention.
FIG. 6T illustrates a femoral guide reference tool attached to the femoral template, in accordance with an embodiment of the invention.
FIG. 6U illustrates a sample implant template positioned on the chondyle, in accordance with an embodiment of the invention.
FIG. 6V is an isometric view of the interior surface of the sample implant template, in accordance with an embodiment of the invention.
FIG. 6W is an isometric view of the tibial template attached to the sample implant, in accordance with an embodiment of the invention.
FIG. 6X shows a tibial template that may be used, after the tibial cut has been made, to further guide surgical tools, in accordance with an embodiment of the invention.
FIG. 6Y shows a tibial implant and femoral implant inserted onto the tibia and femur, respectively, after the above-described cuts have been made, in accordance with an embodiment of the invention.

FIG. 6B illustrates a side view of the first portion 2410 from the perspective of the side surface 2422 illustrating the aperture 2424. As illustrated, the exterior surface 2411 has a uniform surface which is flat, or relatively flat configuration while the interior surface 2413 has an irregular surface that conforms, or substantially conforms, with the surface of the femur.

Figure 6C:
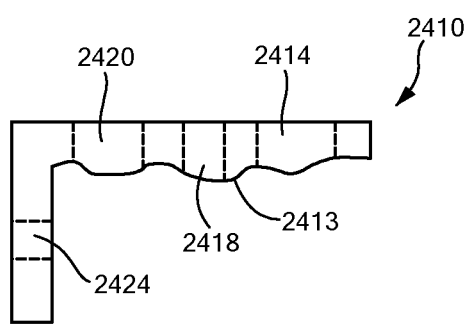
Figure 6D:
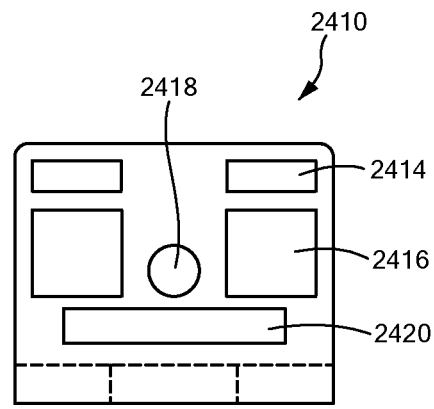

FIG. 6c illustrates another side view of the first, patient specific molded, portion 2410, more particularly illustrating the irregular surface 2413 of the interior. FIG. 6D illustrates the first portion 2410 from a top view. The center bore aperture 2418 is optionally provided to facilitate positioning the first piece and to prevent central rotation.

FIG. 6D illustrates a top view of the first portion 2410. The bottom of the illustration corresponds to an anterior location relative to the knee joint. From the top view, each of the apertures is illustrated as described above. As will be appreciated by those of skill in the art, the apertures can be shaped differently without departing from the scope of the invention.

Turning now to FIG. 6E, the femur 2400 with a first portion 2410 of the cutting block placed on the femur and a second, exterior, portion 2440 placed over the first portion 2410 is illustrated. The second, exterior, portion 2440 features a series of rectangular grooves (2442-2450) that facilitate inserting a saw blade therethrough to make the cuts necessary to achieve the femur shape illustrated in FIG. 1E. These grooves can enable the blade to access at a 90° angle to the surface of the exterior portion, or, for example, at a 45° angle. Other angles are also possible without departing from the scope of the invention.

As shown by the dashed lines, the grooves (2442-2450) of the second portion 2440, overlay the apertures of the first layer.

Figure 26:
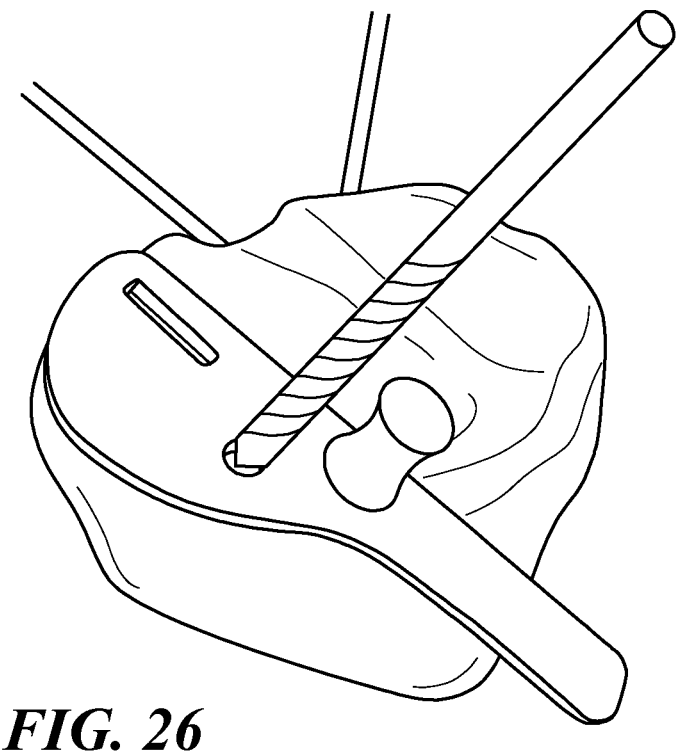
Figure 27:
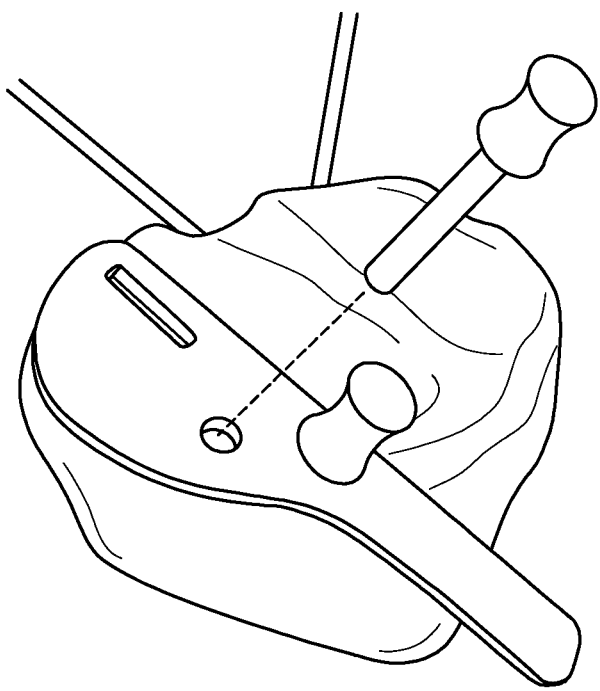

FIG. 6F illustrates a side view of the second, exterior, cutting block portion 2440. From the side view a single aperture 2450 is provided to access the femur cut. FIG. 26G is another side view of the second, exterior, portion 2440 showing the location and relative angles of the rectangular grooves. As evidenced from this view, the orientation of the grooves 2442, 2448 and 2450 is perpendicular to at least one surface of the second, exterior, portion 2440. The orientation of the grooves 2444, 2446 is at an angle that is not perpendicular to at least one surface of the second, exterior portion 2440. These grooves (2444, 2446) facilitate making the angled chamfer cuts to the femur. FIG. 6H is a top view of the second, exterior portion 2440. As will be appreciated by those of skill in the art, the location and orientation of the grooves will change depending upon the design of the femoral implant and the shape required of the femur to communicate with the implant.

FIG. 6I illustrates a spacer 2401 for use between the first portion 2410 and the second portion 2440. The spacer 2401 raises the second portion relative to the first portion, thus raising the area at which the cut through groove 2424 is made relative to the surface of the femur. As will be appreciated by those of skill in the art, more than one spacer can be employed without departing from the scope of the invention. Spacers can also be used for making the tibial cuts. Optional grooves or channels 2403 can be provided to accommodate, for example, pins 2460 shown in FIG. 6J.

Figure 6J:
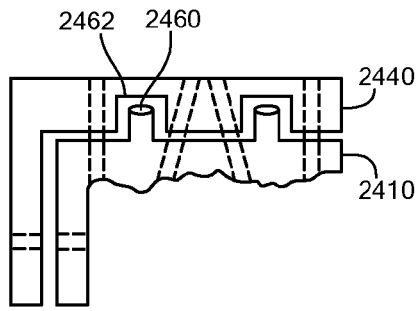

Similar to the designs discussed above with respect to FIG. 5, alternative designs can be used to control the movement and rotation of the cutting block 2440 relative to the mold 2410. As shown in FIG. 6J a series of protrusions, illustrated as pegs 2460, are provided that extend from the superior surface of the mold. These pegs or protrusions can be telescoping to facilitate the use of molds if necessary. As will be appreciated by those of skill in the art, one or more pegs or protrusions can be used without departing from the scope of the invention. For purposes of illustration, two pegs have been shown in FIG. 6J. Depending on the control desired, the pegs 2460 are configured to fit within, for example, a curved slot that enables rotational adjustment similar to the slots illustrated in FIG. 5K or within a recess that conforms in shape to the peg, similar to that shown in FIG. 5L and described with respect to the tibial cutting system. As will be appreciated by those of skill in the art, the recess 2462 can be sized to snugly encompass the peg or can be sized larger than the peg to allow limited lateral and rotational movement.

Figure 6K:
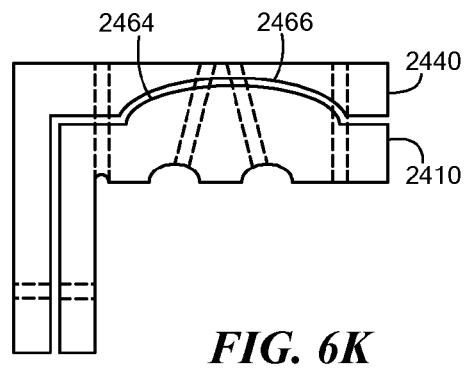
Figure 6L:
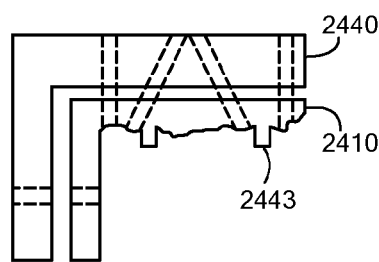
Figure 6M:
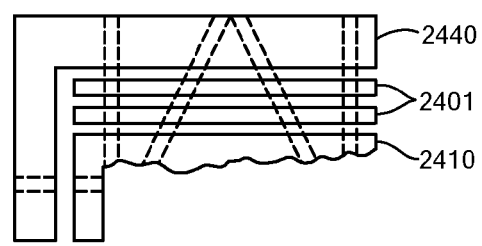

As illustrated in FIG. 6K the surface of the mold 2410 can be configured such that the upper surface forms a convex dome 2464 that fits within a concave well 2466 provided on the interior surface of the cutting block 2440. This configuration enables greater rotational movement about the mechanical axis while limiting lateral movement or translation.

In installing an implant, first the tibial surface is cut using a tibial block, such as those shown in FIG. 6. The patient specific mold is placed on the femur. The knee is then placed in extension and spacers 2401, such as those shown in FIG. 6M, or shims are used, if required, until the joint optimal function is achieved in both extension and flexion. The spacers, or shims, are typically of an incremental size, e.g., 5 mm thick to provide increasing distance as the leg is placed in extension and flexion. A tensiometer can be used to assist in this determination or can be incorporated into the mold or spacers in order to provide optimal results. The design of tensiometers are known in the art and are not included herein to avoid obscuring the invention. Suitable designs include, for example, those described in U.S. Pat. No. 5,630,820 to Todd issued May 20, 1997.

Figure 6N:
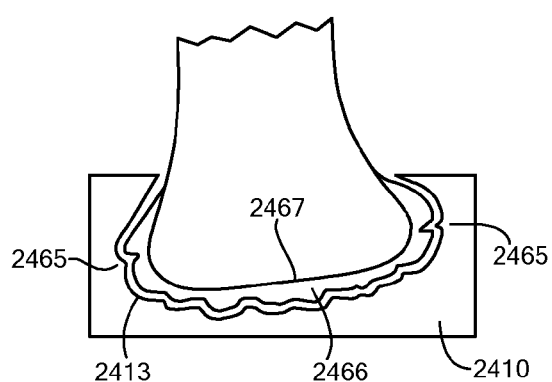
Figure 6O:
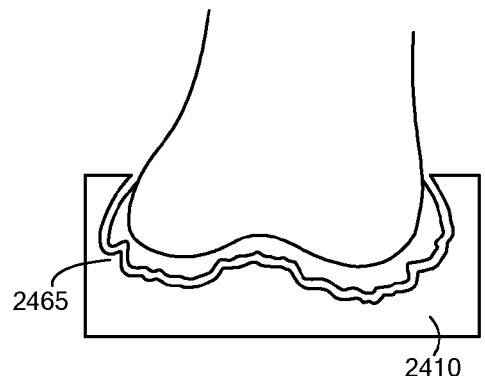

As illustrated in FIGS. 6N (sagittal view) and 6O (coronal view), the interior surface 2413 of the mold 2410 can include small teeth 2465 or extensions that can help stabilize the mold against the cartilage 2466 or subchondral bone 2467.

3D guidance templates may be used to create more that one cut on the same and/or on the opposite articular surface or opposite articular bone, in accordance with an embodiment of the invention. These cuts may be cross-referenced with other cuts using one or more guidance template(s).

In accordance with one embodiment of the invention, the 3D guidance template(s) are utilized to perform more than one cut on the same articular side such as the femoral side of a knee joint. In another embodiment, a 3D guidance template may be utilized to cross reference surgical interventions on an opposing articular surface. In a knee, for example, the first articular surface can be the femoral surface. The opposing articular surface can be the tibial surface or the patella surface. In a hip, the first articular surface can be the acetabulum. The opposing articular surface or the opposing bone can be the proximal femur.

Thus, in a knee, a horizontal femur cut can be cross-referenced with an anterior or posterior femur cut or optionally also chamfer, oblique cuts. Similarly, a tibial horizontal cut can be cross-referenced with any tibial oblique or vertical cuts on the same articular side or surface.

In accordance with another embodiment, one or more femur cuts can be crossed-referenced with one or more tibial cuts. Or, in a hip, one or more acetabular cuts or surgical interventions can be cross-referenced with one or more femoral cuts or surgical interventions such as drilling, reaming or boring. Similarly, in a knee again, one or more femur cuts can be cross-referenced with one or more patella cuts. Any combination and order is possible.

The cross-referencing can occur via attachments or linkages including spacers or hinge or ratchet like devices from a first articular bone and/or cartilage surface, to a second articular, bone and/or cartilage surface. The resulting positioning of the cut on the opposing articular, bone or cartilage surface can be optimized by testing the cut for multiple pose angles or joint positions such as flexion, extension, internal or external rotation, abduction or adduction. Thus, for example, in a knee a distal femur cut can be performed with a mold. Via a linkage or an attachment, a tibial template may be attached thereto or to the cut or other surgical intervention, thus a cross-reference can be related from the femoral cut to a tibial cut or other surgical intervention. Cross-referencing from a first articular surface to a second articular surface via, without limitation, attachments or linkages to a template has the advantage of insuring an optimal alignment between the implant or other therapeutic device components of the first articular surface to that on a second articular surface. Moreover, by cross-referencing surgical interventions on a first articular surface to a second articular surface, improved efficiencies and time savings can be obtained with the resulted surgical procedure.

Cross-referencing the first, the second and, optionally a third or more articular surface, such as in a knee joint, may be performed with a single linkage or attachment or multiple linkages or attachments. A single pose angle or position of a joint or multiple pose angles or positions of a joint may be tested and optimized during the entire surgical intervention. Moreover, any resulting surgical interventions on the opposite, second articular surface, bone or cartilage may be further optimized by optionally cross-referencing to additional measurement tools such as standard alignment guides.

For example, in a knee joint, a 3D template may be utilized to perform one or more surgical interventions on the femoral side, such as a femoral cut. This can then be utilized via a linkage, an attachment or via indirect cross-referencing directly onto the site of surgical intervention, to guide a surgical intervention such as a cut of the tibial side. Prior to performing the surgical intervention on the tibial side, a traditional tibial alignment guide with cross-reference to the medial and lateral malleolus of the ankle turn may be used to optimize the position, orientation and/or depth and extent of the planned surgical intervention such as the cut. For example, cross-referencing to the femoral cut can aid in defining the relative superior inferior height of the tibial cut, while cross-referencing a tibial alignment guide can optionally be utilized to determine the slant of the cut in the interior posterior direction.

An exemplary system and methodology is now described in which a femoral template is used to make a cut on the femur, which is then cross-referenced to properly align a tibial template for making a cut on the tibial plateau. Initially, an electronic image(s) of the leg is obtained using imaging techniques elaborated in above-described embodiments. For example, a pre-operative CT scan of a patient's leg may be obtained to obtain electronic image data.

Image processing is then applied to the image data to derive, without limitation, relevant joint surfaces, axis, and/or cut planes. Image processing techniques may include, without limitation, segmentation and propagation of point clouds.

Figure 6P:
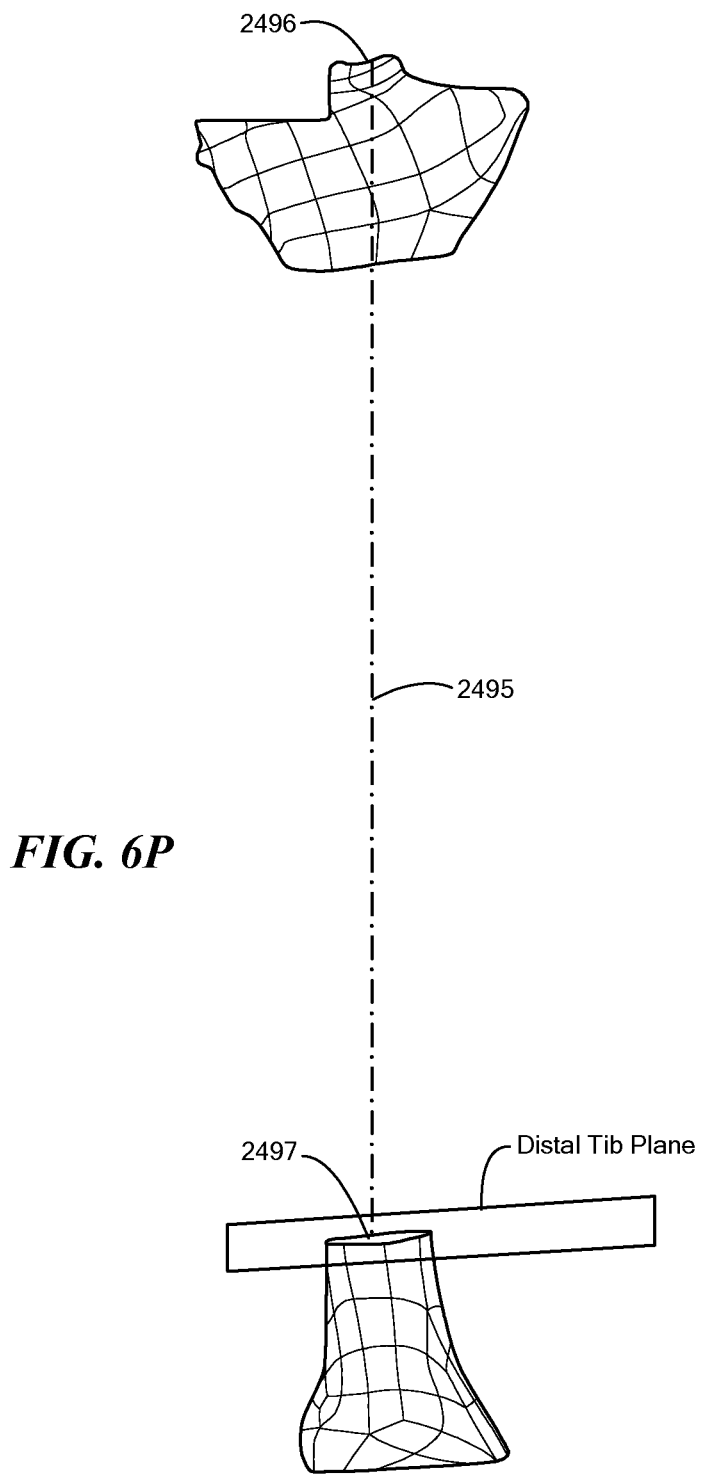
Figure 6Q:
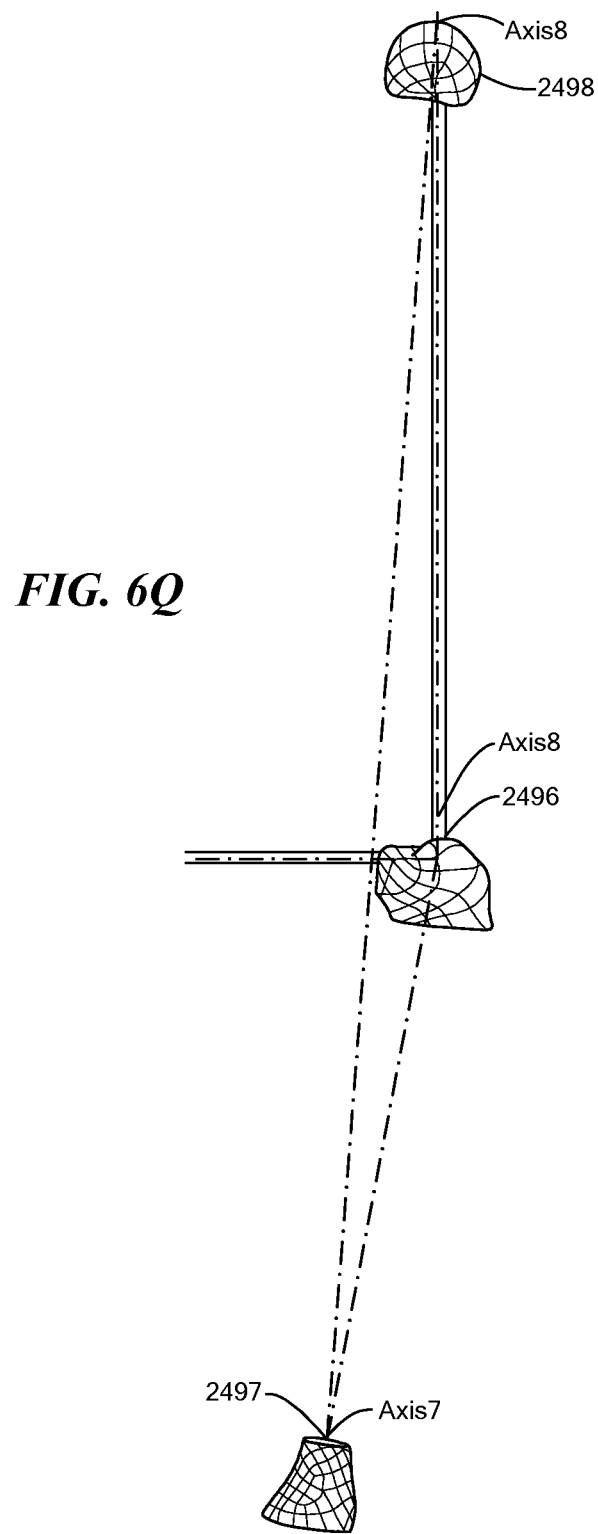

Relevant biomechanical and/or anatomical axis data may be obtained by identifying, for example, the central femoral head, central knee joint and center of the distal tibia. The cutting planes may then be defined based on at least one of these axis. For example, the tibial implant bearing surface may be defined as being perpendicular to the axis defined by the center of the tibial plateau 2496 and the center of the distal tibia 2497, as illustrated in FIG. 6P; the tibial implant's medial margin may project towards the femoral head, as illustrated in FIG. 6Q; and the anterior to posterior slope of the tibia may be approximated by the natural anatomical slope (alternatively, excessive tibial slope may be corrected).

Figure 6R:
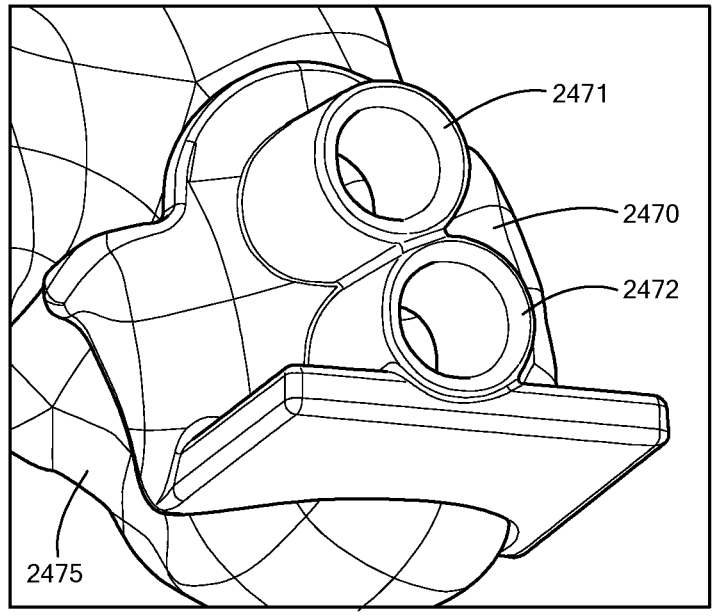
Figure 6S:
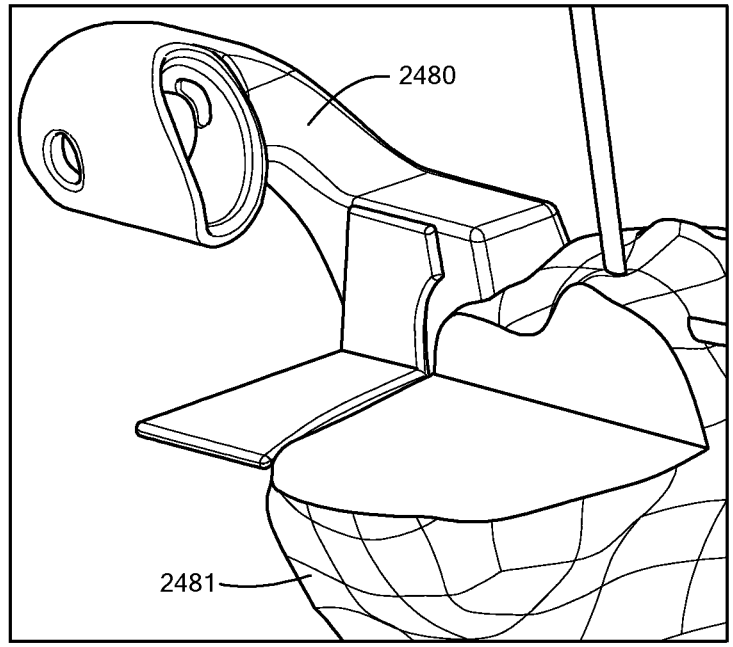

The tibial and femoral templates and implants may be designed based, at least in part, on the derived joint surfaces, axis and/or cut planes. FIGS. 6R and 6S show isometric views of a femoral template 2470 and a tibial template 2480, respectively, in accordance with an embodiment of the invention. The femoral template 2470 has an interior surface that, in various embodiments, conforms, or substantially conforms, with the anatomic surface (bone and/or cartilage) of the femur 2475. Furthermore, the interior surface of the femoral template may extend a desired amount around the anatomical bony surfaces of the condyle to further ensure proper fixation. The interior surface of the tibial cutting block 2480 may conform, or substantially conform to the surface (bone and/or cartilage) of the tibia 2481.

In an exemplary use, the femoral template 2470 is placed on the femoral condyle 2475, for example, when the knee is flexed. The femoral template 2470 may be fixed to the femoral condyle 2475 using, without limitation, anchoring screws/drill pins inserted through drill bushing holes 2471 and 2472. The position of holes 2471 and 2472 on the condyle may be the same used to anchor the final implant to the femur. In various embodiments, the holes 2471 and 2472 may include metal inserts/bushings to prevent degradation when drilling. Fixing the template 2470 to the femoral condyle 2475 advantageously prevents movement of the template during subsequent cutting or other surgical interventions thereby ensuring the accuracy of the resultant surgical cuts.

Figure 6T:
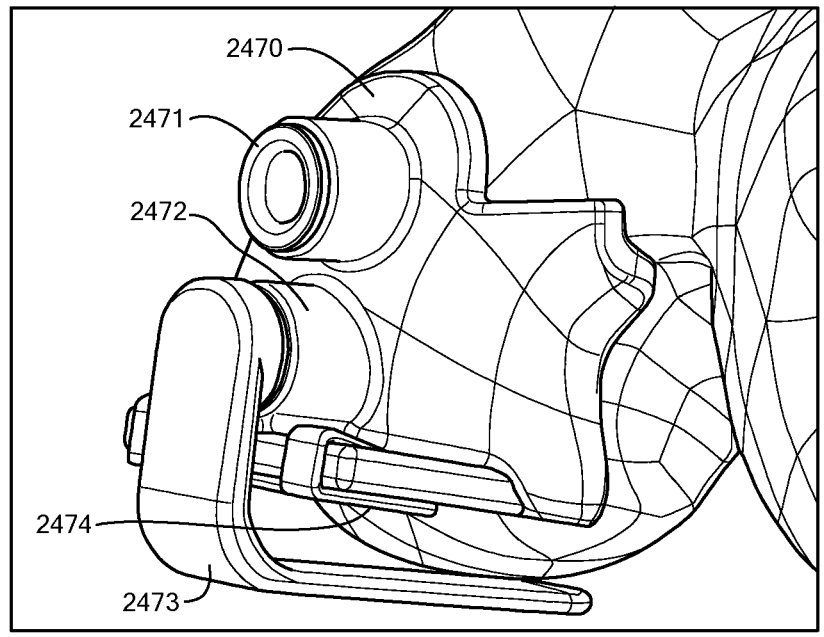

To assist in accurately positioning the femoral template 2470, a femoral guide reference tool 2473 may be attached to the femoral template 2470, as shown in FIG. 6T. The femoral guide reference tool 2473 may, without limitation, attach to one of holes 2471 and 2472. The femoral guide reference tool 2473 may reference off the tangential margin of the posterior condyle, and aid, for example, in correct anterior-posterior positioning of the femoral template 2470.

Upon proper fixation of the femoral template 2470 to the femoral condyle 2475, a cut to the femoral condyle is made using cut guide surface or element 2474. The cut guide surface or element 2474 may be integral to the femoral template 2470, or may be an attachment to the femoral template 2470, with the attachment made of a harder material than the femoral template 2470. For example, the cut guide surface or element 2474 may be a metal tab that slides onto the femoral template 2470, which may be made, without limitation, of a softer, plastic material.

Figure 6U:
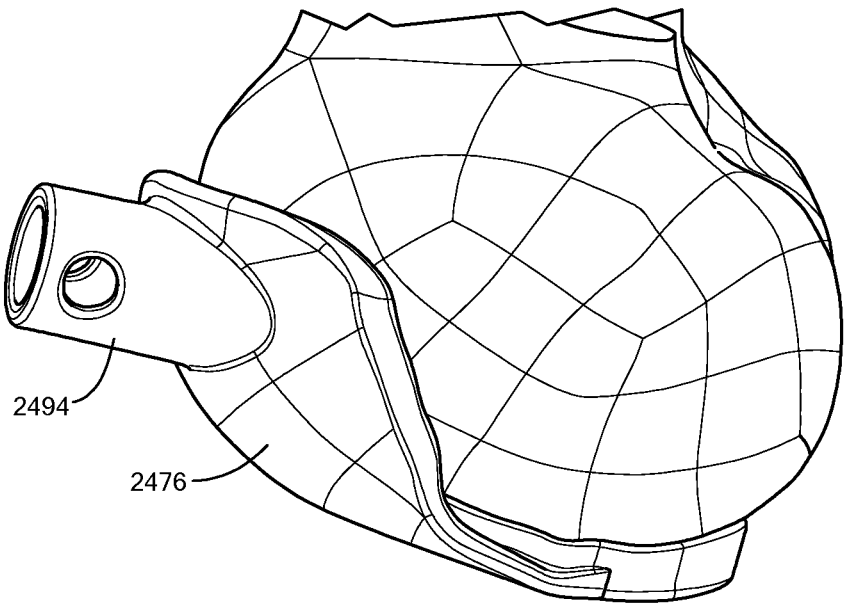

Upon making the femoral cut and removing the femoral template 2475, a sample implant template 2476 (not the final implant) is optionally positioned on the condyle, as shown in FIG. 6u, in accordance with an embodiment of the invention. The sample implant template 2474 may be attached to the condyle by using without limitation, anchoring screws/drill pins inserted through the same holes used to anchor the final implant to the femur.

The sample implant template 2476 includes an attachment mechanism 2494 for attaching the tibial template 2480, thereby cross-referencing the placement of the distal tibial cut with respect to the femoral cut/implant's placement. The attachment mechanism 2494 may be, without limitation, a boss, as shown in FIG. 6U, or other attachment mechanism known in the art, such as a snap-fit mechanism. Note that in alternative embodiments, a sample implant template 2476 is not required. For example, the tibial template 2480 may attach directly to the femoral template 2470. However, in the subject embodiment, the drill bushing features of the femoral template 2475 will interfere with the knee going into extension, preventing the tibial cut.

In illustrative embodiments, the thickness of the sample implant template 2476 may not only include the thickness of the final femoral implant, but may include an additional thickness that corresponds to a preferred joint space between tibial and femoral implants. For example, the additional thickness may advantageously provide a desired joint space identified for proper ligament balancing or for flexion, extension, rotation, abduction, adduction, anteversion, retroversion and other joint or bone positions and motion.

Figure 6V:
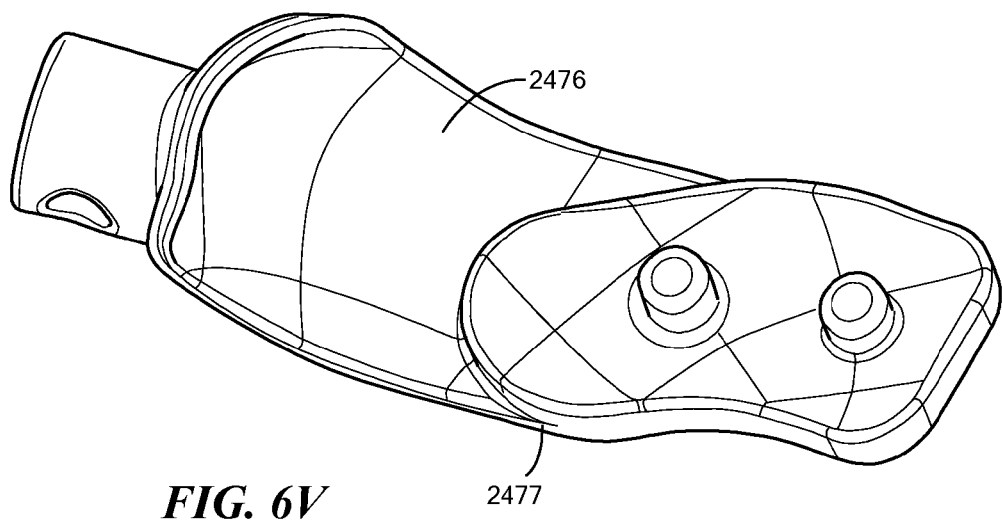

FIG. 6V is an isometric view of the interior surface of the sample implant template 2476, in accordance with an embodiment of the invention. In various embodiments, the femoral implant often rests on subchondral bone, with the cartilage being excised. In embodiments where the sample implant template 2474 extends beyond the dimensions of the femoral implant such that portions of the sample implant template 2476 rests on cartilage, an offset 2477 in the interior surface of the sample implant template 2476 may be provided.

Figure 6W:
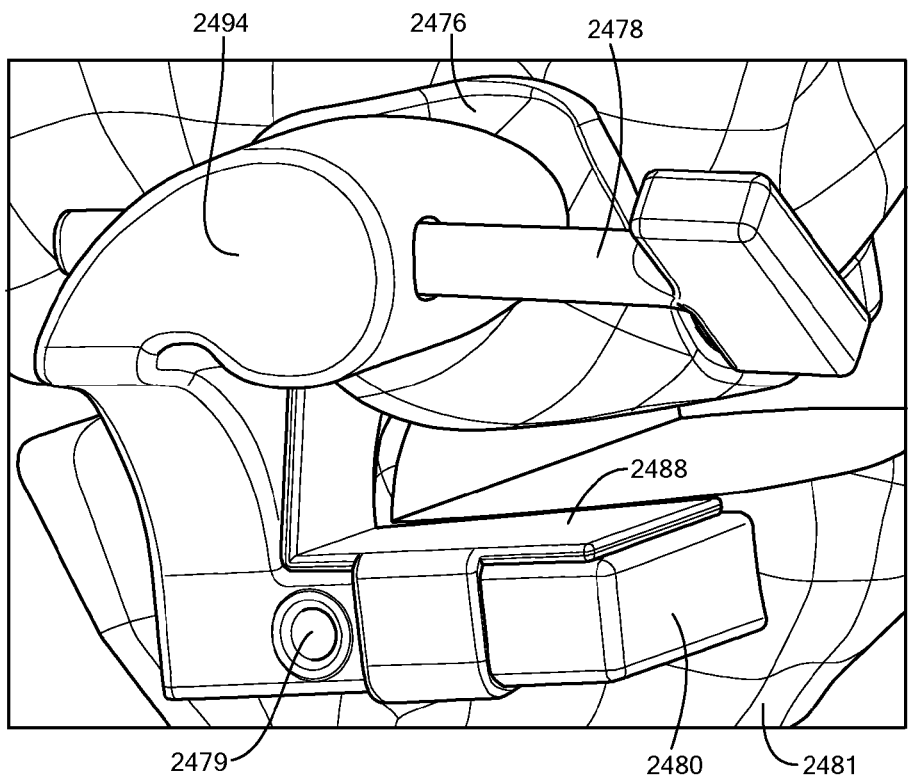

FIG. 6W is an isometric view of the tibial template 2480 attached to the sample implant 2476 when the knee is in extension, in accordance with an embodiment of the invention. A crosspin 2478 inserted through boss 2494 fixes the tibial template 2480 to the sample implant template 2474. Of course, other attachment mechanisms may be used, as described above. In preferred embodiments, the tibial template 2480 may also be fixed to the tibia 2481 using, without limitation, anchoring screws/drill pins inserted through drill bushing hole 2479. In various embodiments, the holes 2479 include metal inserts (or other hard material) to prevent degradation when drilling. As with the femoral template 2475, the cut guide surface or element of the tibial template 2480 may be integral to the tibial template 2475, or may be an attachment to the tibial template 2480, the attachment made of a harder material than the tibial template 2480. Upon fixing the position of the tibial template 2480, the cut guide of the tibial template 2475 assists in guiding the desired cut on the tibia.

Figure 6X:
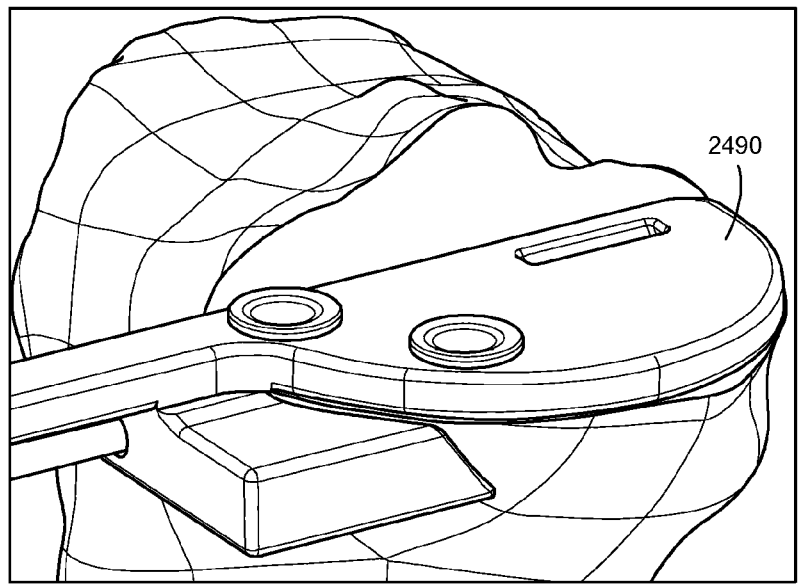

FIG. 6X shows a tibial template 2490 that may be used, after the tibial cut has been made, to further guide surgical tools in forming anchoring apertures in the tibia for utilization by the tibial implant (e.g., the tibial implant may include pegs and/or keels that are used to anchor the tibial implant into the tibia), in accordance with an embodiment of the invention. The outer perimeter of a portion of the tibial template 2490 may mimic the perimeter of the tibial implant. Guide apertures in the tibial template 2490 correspond to the tibial implants fixation features. A portion of the tibial template 2490 conforms to, without limitation, the anterior surface of the tibia to facilitate positioning and anchoring of the template 2490.

Figure 6Y:
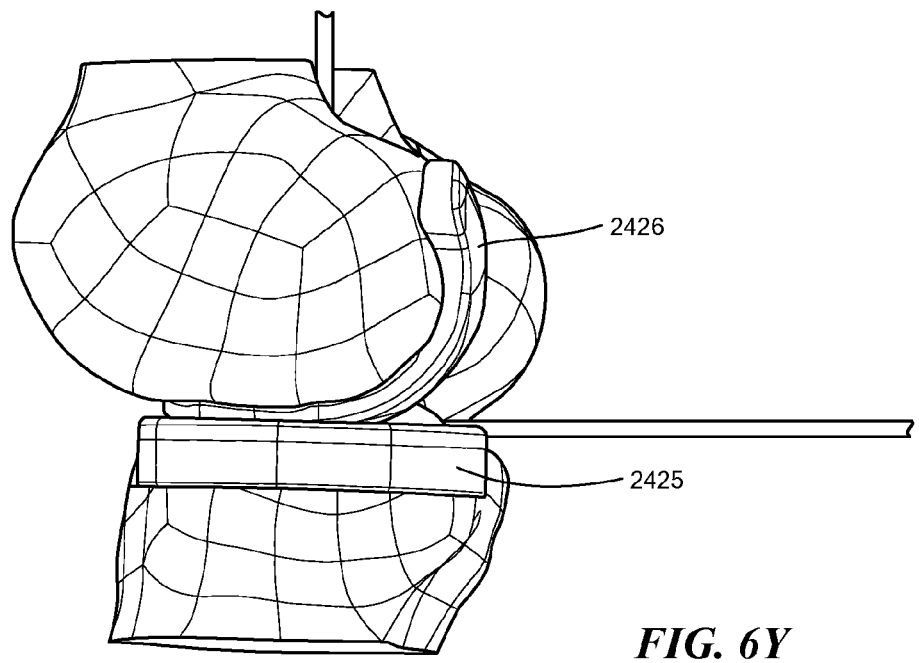

FIG. 6Y shows a tibial implant 2425 and femoral implant 2426 inserted onto the tibia and femur, respectively, after the above-described cuts have been made, in accordance with an embodiment of the invention.

Thus, the tibial template 2480 used on the tibia can be cross-referenced to the femoral template 2476, femoral cut and/or sample implant 2474. Similarly, in the hip, femoral templates can be placed in reference to an acetabular mold or vice versa. In general, when two or more articular surfaces will be repaired or replaced, a template can be placed on one or more of them and surgical procedures including cutting, drilling, sawing or rasping can be performed on the other surface or other surfaces in reference to said first surface(s).

An alternative embodiment of a knee implant, system and method is presented herein below. In this embodiment, a library of patient-specific femoral spacing templates are utilized to provide accurate and anatomically-correct ligament balancing, and patient-specific templates, including an alignment tool for placing the vertical cut for the medial edge of the tibial component on tibial plateau, provide precise positioning of the femoral and tibial implants. In a procedure for installing an implant, the joint surfaces are first prepared to receive the templates and the implants. A line may desirably drawn on the femoral end, using, e.g., a marker or electrosurgical pencil, to mark the anterior sulcus. Thereafter, soft tissue cartilage is desirably removed from the anterior sulcus, e.g., using a curved elevator/osteotome, and posterior cartilage is removed also, e.g., using a, e.g., 10 mm blade. Anterior cartilage removal is desirably started in this procedure a small distance, e.g., 1 or 2 mm, below the sulcus line. Cartilage removal may be completed using, e.g., a 5 mm ringed/open curette.

Figure 7:
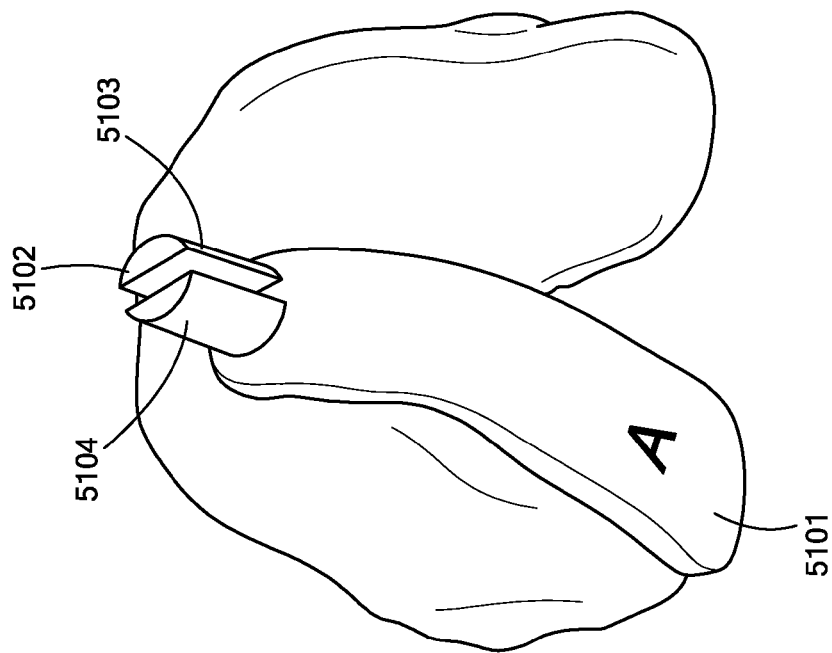
FIG. 7 illustrates a femoral balancing template on a femur, in accordance with one embodiment of the invention.

Next, the knee is placed into extension and patient-specific femoral balancing templates are used to properly balance the ligaments in the knee, and in so doing determine the correct locations for the femoral and tibial components. The design (e.g., surface contours, outer geometry) of the femoral balancing templates is desirably derived from patient-specific data, e.g., a CT image of the joint in question. Desirably a plurality of femoral balancing templates, each with a characteristically larger thickness, is provided to enable convenient but accurate ligament balancing. A greater number of femoral balancing templates (i.e., smaller incremental thickness from one template to the next) provides more control over ligament balancing, but fewer femoral balancing templates may be sufficient and also will have the advantage of a less-complex tool set for the surgeon to deal with. A representation of a femoral balancing template 5101 on a femur, featuring split lug 5102, and through-holes 5103 and 5104, is depicted in FIG. 7. The design of the femoral balancing template may desirably mimic that of the permanent femoral implant.

Figure 8:
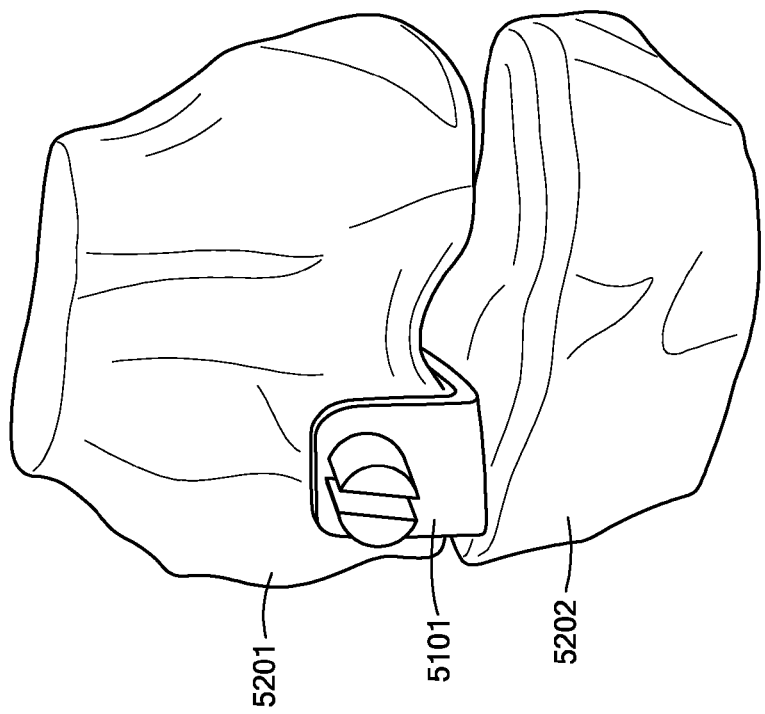
FIG. 8 illustrates a knee in balanced extension with femoral balancing template fitted on the femoral condyle, in accordance with an embodiment of the invention.

The surgeon determines the appropriate femoral balancing template to achieve the desired ligament tensioning in extension, from the choices at hand, and the template is placed on the condylar surface for which it is intended, while the knee is in flexion. Once the femoral balancing template is securely placed in its intended location on the condylar surface (which may include bone and/or cartilage), the knee is placed into extension. Some cartilage may be removed from the tibia if the fit in extension is too tight. FIG. 8 shows a view of a knee in balanced extension with femoral balancing template 5101 fitted on femoral condyle 5201 and between femoral condyle 5201 and tibial plateau 5202.

Figure 9:
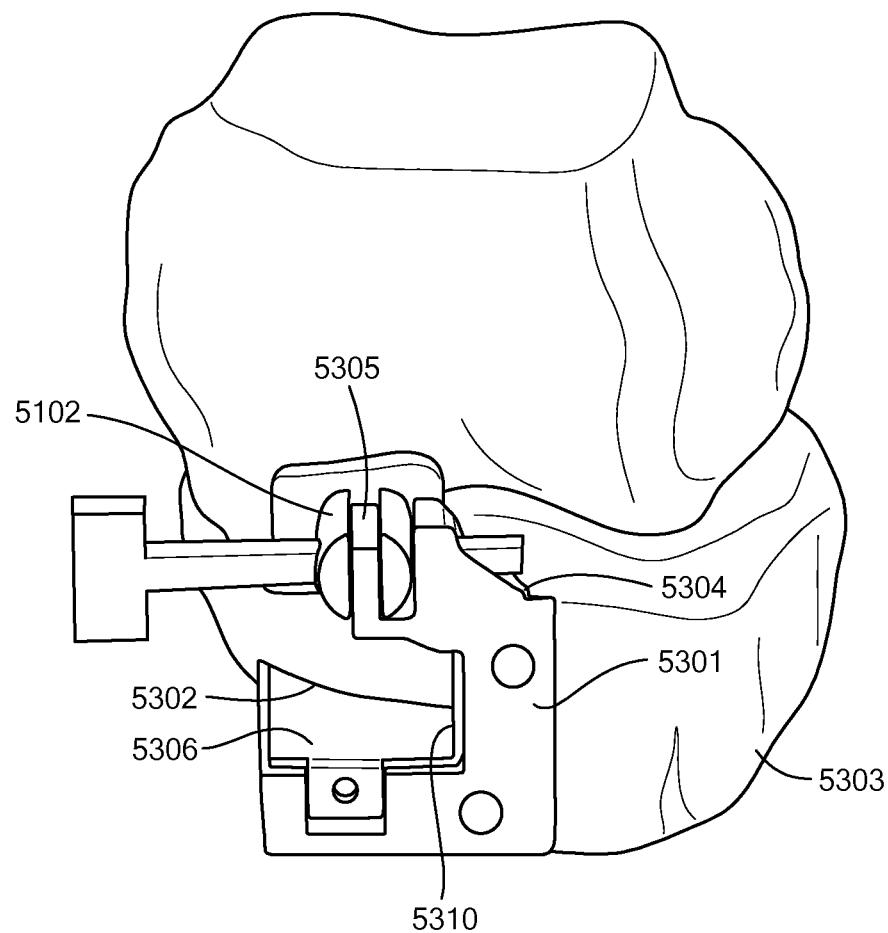
FIG. 9 illustrates a tibial cutting guide fitted to the tibia when balanced in extension, in accordance with an embodiment of the invention.

Once the knee has been balanced in extension, a tibial cutting guide 5301, having an interface surface 5302 which conforms to an anterior surface of the tibia 5303, is fitted to the tibia, as shown in FIG. 9. Interface surface 5302 is desirably derived from patient-specific data. Locking arm 5304 is designed to fit tab 5305 into the slot of split lug 5102. Horizontal cutting guide 5306 and stop 5310 are provided to enable the horizontal cut for the tibial implant, and pin holes 5307 and 5308 are provided so guide 5301 may be secured to the anterior tibial face. Tab 5305 is fitted into the slot of split lug 5102, and secured to femoral balancing template 5101 with cross-pin 5309. A tibial alignment guide (not shown) may be desirably attached to the tibial cutting guide at this point in time to confirm slope (tibial axial alignment). Such a tibial alignment guide comprises an ankle clamping means at one end of the alignment guide, distal to the knee; a rod attached to and spanning from the ankle clamping means to the tibial cutting guide; and attachment means to attach the rod to the tibial cutting guide.

Figure 10:
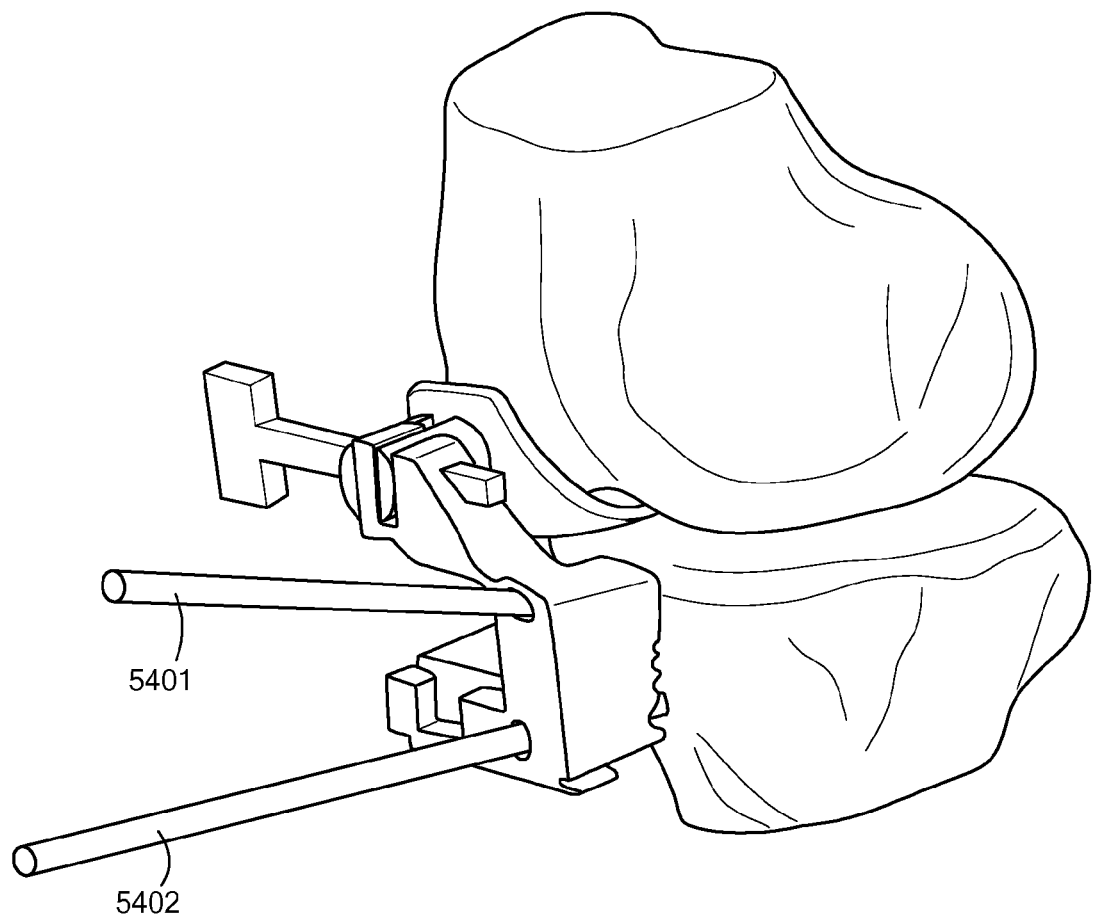
FIGS. 10 and 11 illustrate the tibial cutting guide pinned in place, in accordance with an embodiment of the invention.
Figure 11:
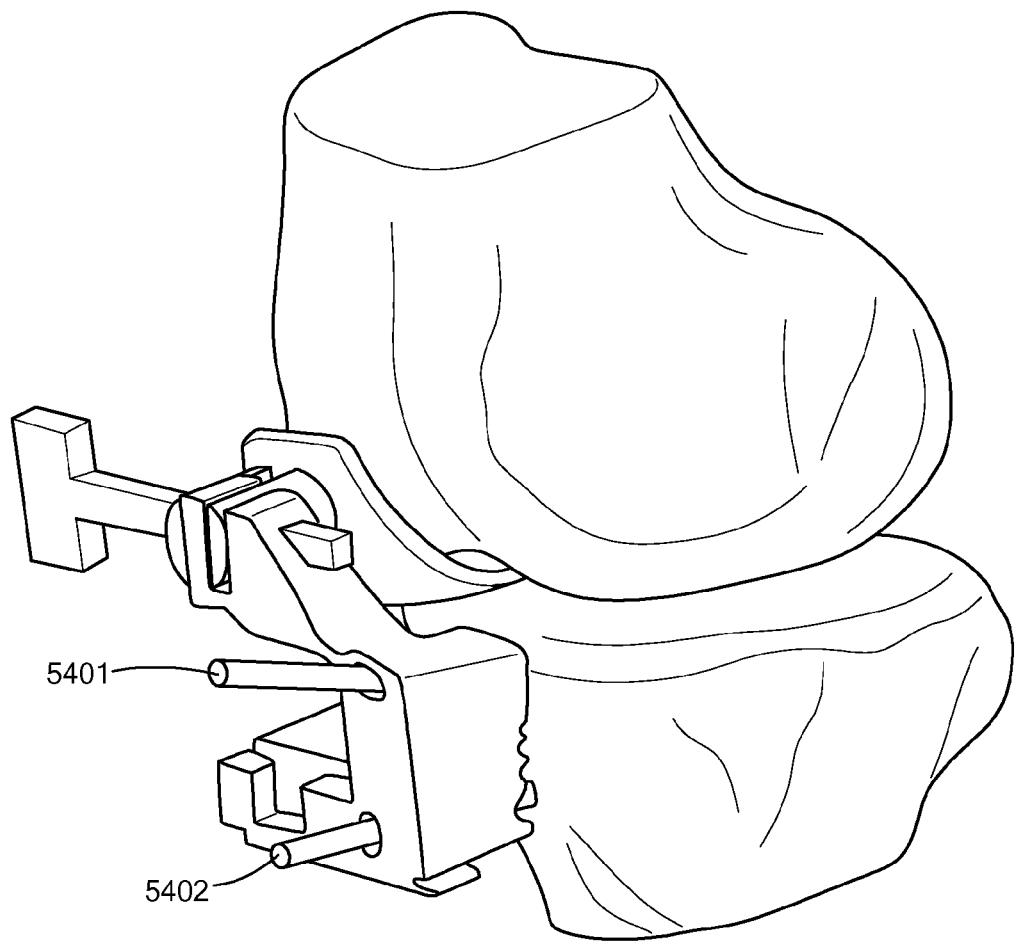

Once proper alignment of tibial cutting guide 5301 is confirmed, drill holes are made through pin holes 5307 and 5308, and the guide is pinned in place by inserting pins 5401 and 5402 into the drill holes, as seen in FIGS. 10 and 11.

Figure 12:
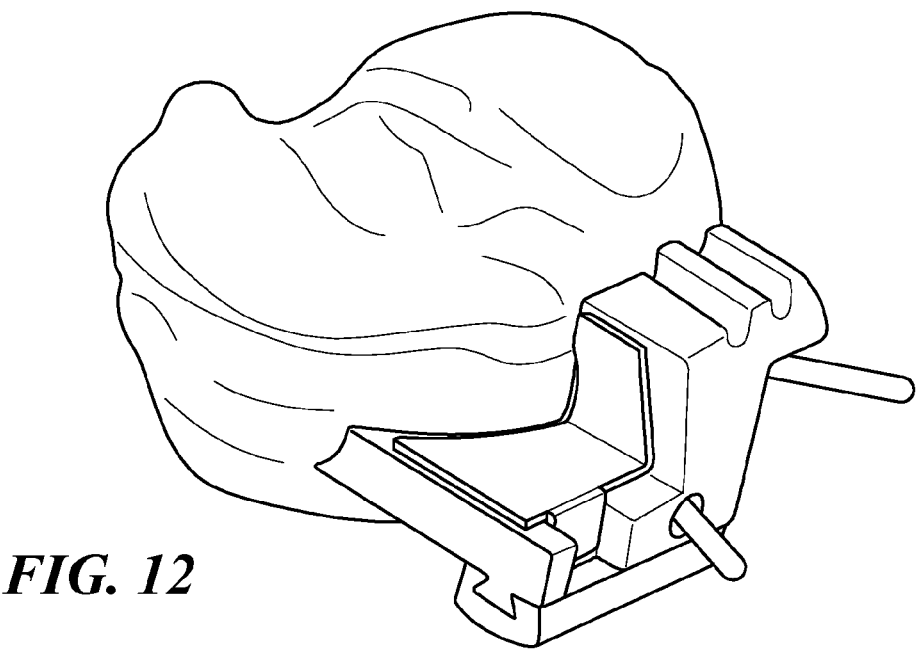
FIG. 12 illustrates the tibial cutting guide with femoral balancing template removed, in accordance with an embodiment of the invention.
Figure 13:
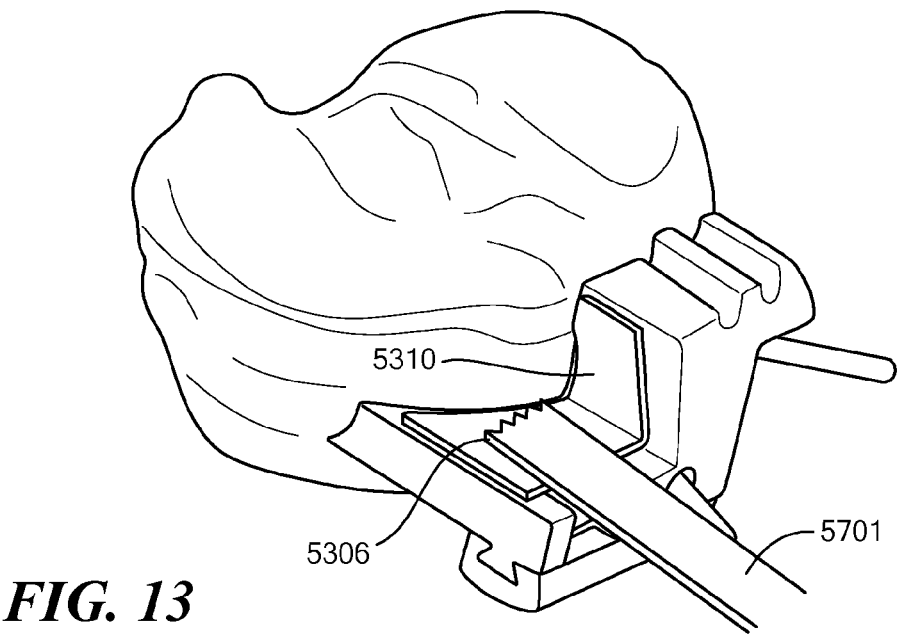
FIG. 13 illustrates the coronal tibial cut being made, in accordance with an embodiment of the invention.

Next, the horizontal tibial cut for the tibial implant is made. Cross-pin 5309 is removed, the knee is brought into flexion, and femoral balancing template 5101 is removed, as depicted in FIG. 12. The coronal tibial cut is made by guiding oscillating saw blade 5701 (FIG. 13) against horizontal cutting guide 5306; stop 5310 keeps the horizontal cut from proceeding past the desired end. Once the horizontal cut is made, the tibial cutting guide is removed.

Figure 14:
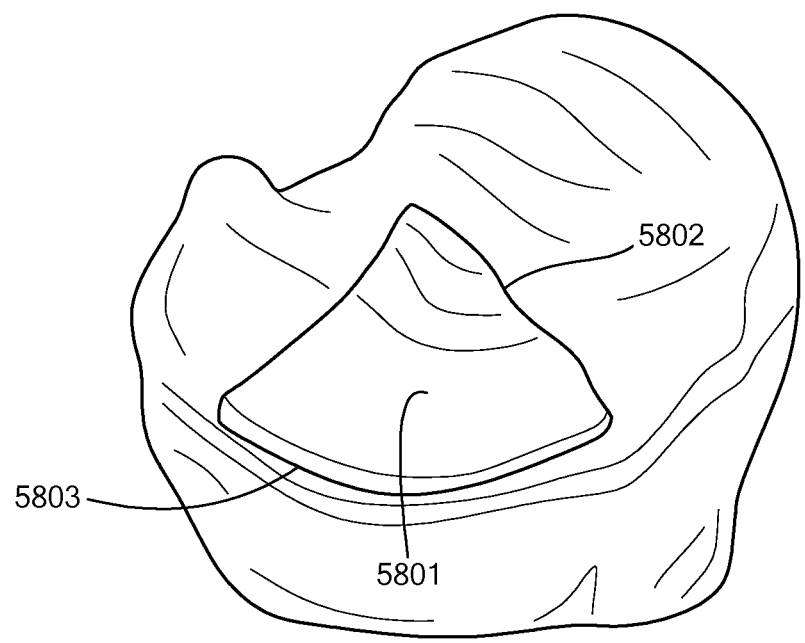
FIGS. 14 and 15 illustrate the use of a patient-specific vertical cut alignment tool to place the vertical tibial cut, in accordance with an embodiment of the invention.
Figure 15:
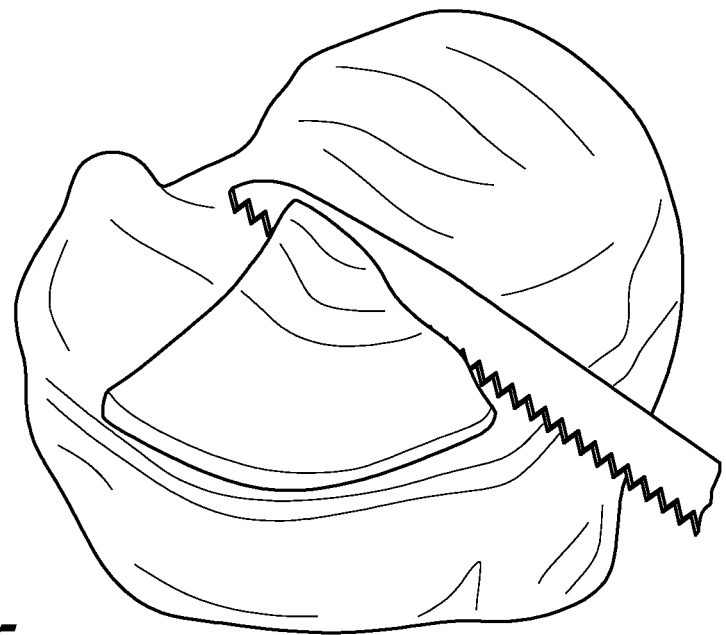

FIGS. 14 and 15 illustrate the use of a patient-specific cut alignment tool 5801 (also referred to herein as a navigation chip) to precisely place, without limitation, at least one of a vertical tibial cut or a horizontal tibial cut. Tool 5801 may have a straight medial edge 5802 that may correspond to the line where the vertical cut for the tibial implant is to be placed, and patient-specific surface 5803 that is a mirror image of the tibial surface (which may include bone and/or cartilage) to which it is to mate. The patient-specific surface 5803 may be substantially a mirror image of the articular of the articular cartilage, including normal or diseased cartilage, the subchondral bone, or, optionally, exposed endosteal bone or bone marrow, or combinations thereof. In other words, when surface 5803 is fitted to the tibial plateau, the desired location for the vertical cut, and, by extension, the external edge of the tibial implant, is precisely determined. For example, in a medial unicompartmental implant, the external edge can include the medial aspect of the tibial cortical bone. In a lateral unicompartmental implant, the external edge can include the lateral aspect of the tibial cortical bone. In various embodiments, the patient-specific cut alignment tool 5801 may conform to a weight bearing surface, a non-weight bearing surface, and/or an anatomical landmark. In further embodiments, the patient patient-specific cut alignment tool 5801 may have a periphery or an outer edge that matches the rim or outer periphery of the surface it contacts (e.g., the outer periphery of the tibial plateau), allowing, for example, further visual confirmation of proper alignment. In still further embodiments, the tibial cut alignment tools disclosed herein have the benefit of ensuring that the outer edge of the tibial implant to does not overhang or underhang the cut edge of the tibial plateau. In still further embodiments the patient specific alignment tools can rest on the articular surface, but can also extend to or include cortical bone and can even rest against soft-tissue including ligamentous structures.

In various embodiments, the top surface of the alignment tool 5801 may be flat, convex, or concave or combinations thereof. The top surface may be, at least in part, patient matched to the tibia or the femur. For example, the top surface may be, at least in part, a copy or near copy of the tibial surface. Alternatively, the top surface of the alignment tool may be, at least in part, a mirror image of one or more femoral condyles. In all of these embodiments, the top surface of the tibial alignment tool 5801 may be derived from the articular cartilage, including normal or diseased cartilage, the subchondral bone, or, optionally, exposed endosteal bone or bone marrow, or combinations thereof.

In another embodiment, the top surface of the alignment tool 5801 may be a mirror image of, at least in part, a femoral implant bearing surface. The femoral implant bearing surface can be a standard (off-the-shelf) bearing surface or can be patient individualized, e.g. to the patient's bone or cartilage or combinations thereof. The top surface of the alignment tool 5801 may be a mirror image to, at least in part, a femoral implant bearing surface in at least one of a coronal plane, a sagittal plane, or combinations thereof, Before the alignment tool 5801 is placed on the plateau of FIGS. 14 and 15, cartilage may be optionally removed from the plateau, e.g., the anterior two thirds of the tibia. The alignment tool 5801 is placed on the plateau, and a vertical cut is made as illustrated in FIG. 15. Alternatively, the tool 5801 may be kept in place, a line made along edge 5802 with an electrosurgical pencil, and the cut may be made along the pencil line with the tool 5801 removed. The profile of the tibial cut may be confirmed using a spacer block as described below.

Figure 29:
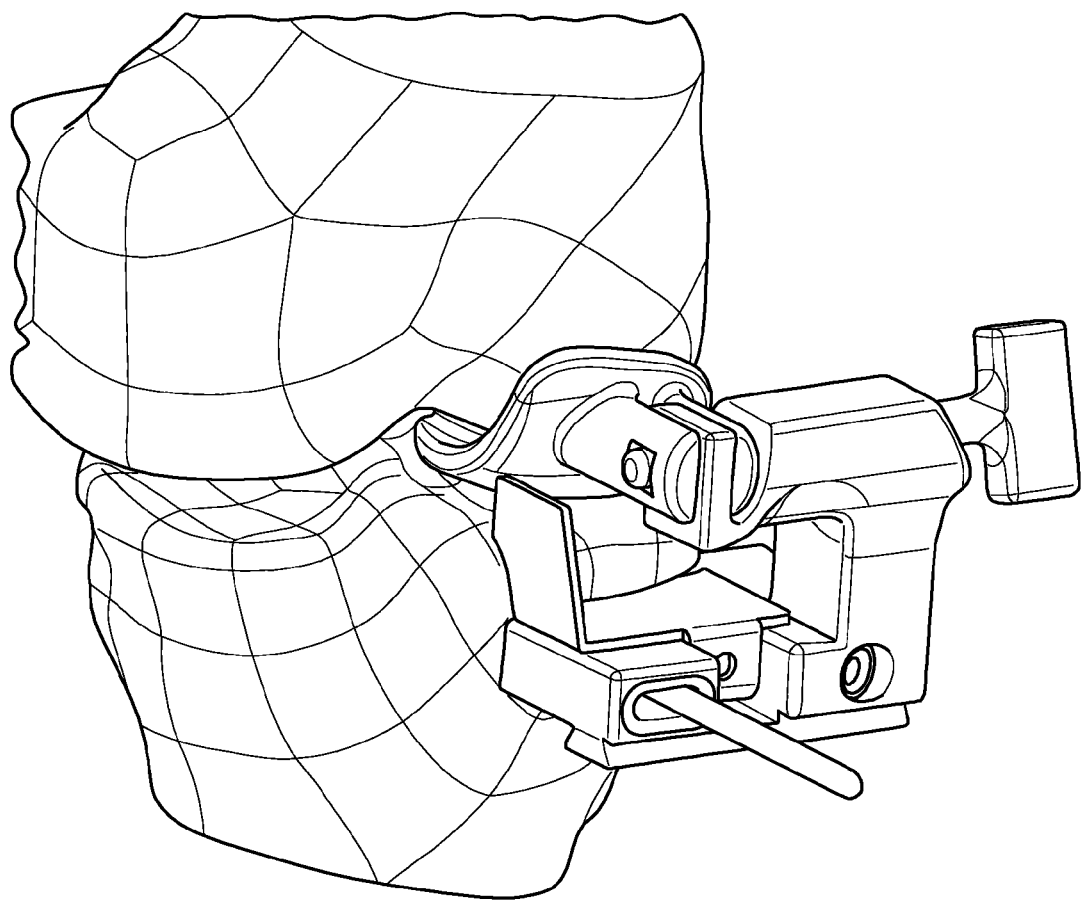
FIG. 29 illustrates a fin created using an osteotome, in accordance with an embodiment of the invention.
Figure 30:
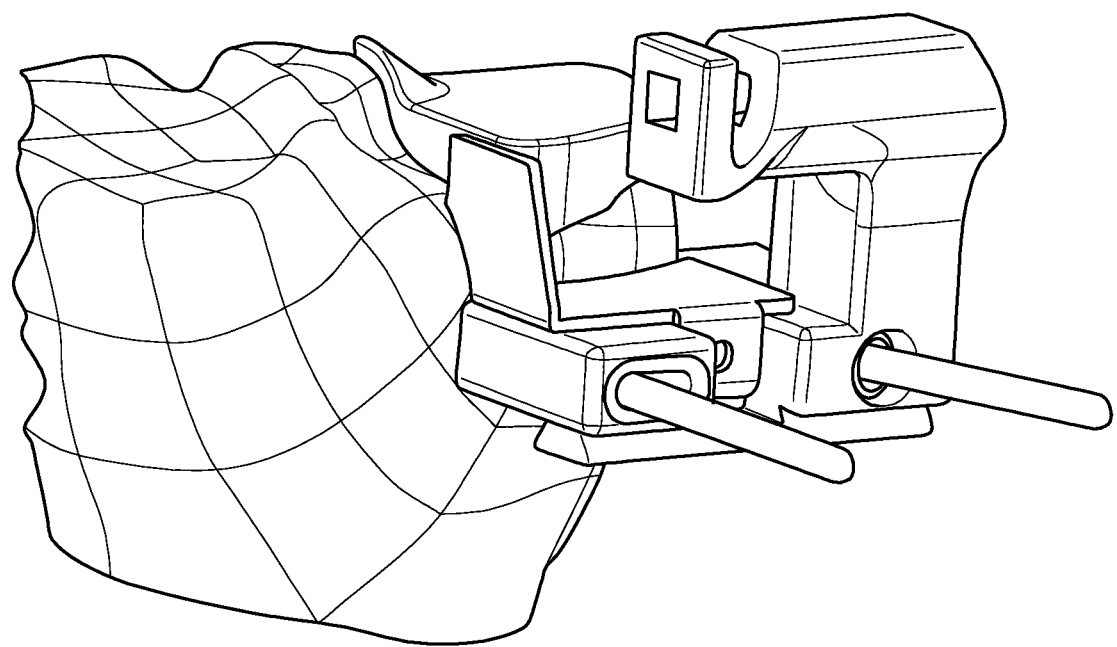
FIG. 30 shows a tibial cut guide pinned in extension, in accordance with one embodiment of the invention.

In still other embodiments, the patient-specific cut alignment tool 5801 may be used to simply visually confirm the location of a cut, with another cut guide used to actually direct the surgical instrument in making the cut. FIG. 29 shows a tibial cut guide pinned in extension, in accordance with one embodiment of the invention. FIG. 30 shows the femoral balancing template removed, the patient specific alignment tool 5801 positioned on the tibial plateau, and a cutting guide attached to the tibia. The cutting guide may be used to make both the horizontal and vertical cuts on the tibial plateau, in accordance with one embodiment of the invention. In FIG. 29, the cutting guide is secured to the tibia using, in part, an optional pin hole or a linkage or joint that is shaped so as to allow limited or direct movement of the cutting guide when the femoral balancing template is removed. The patient-specific cut alignment tool 5801 is used to confirm the location of the cut, and the position of the cutting guide is adjusted to align with the confirmed location. Once in the proper position, the cutting guide can be fixed in position via another pin/pin hole, as shown in FIG. 29, and the cut can be made.

In yet other embodiments, the patient-specific cut alignment tool 5801 may be used to properly balance the ligaments in the knee, with or without, for example, the use of the femoral balancing template(s). A plurality of patient-specific cut alignment tools 5801 may be provided, each with a characteristically larger thickness. The top surface of the patient-specific cut alignment tools 5801 may be flat to allow for easier balancing. It may also have a slight curvature to it, which may be convex or concave. Various chips may be inserted, with a chip selected that provides the desired ligament tensioning. For example, each chip may be inserted in turn from, without limitation, thinnest to thickest with the knee in flexion or extension and then taken through the desired range of motion. The anatomic shape of the balancer allows for simplified balancing without the typical complexity of most balancing procedures.

Thus, the patient-specific alignment tool 5801 may fulfill multiple functions: It may be used for guiding a vertical tibial cut, if a partial tibial replacement is contemplated. It may be used for referencing a horizontal tibial cut, when a partial or total knee system is contemplated. In this case, it may be combined it with spacer blocks or femoral balancing tools. It may be used for ligament balancing. Moreover, the patient specific alignment tool 5801 may be made available in various thicknesses, e.g. 1, 2, 3 or 4 mm for testing ligament tension in at least one of flexion or extension or combinations thereof for achieving optimal ligament balancing or soft-tissue or ligament tensioning. The thickness of the balancing chip that is inserted will determine the level at which the horizontal tibial cut is made. For example, with a thicker balancing or navigation chip, the tibial cut will be more superior, i.e. more tibial bone is preserved. With a thinner navigation chip, the tibial cut will be more inferior, i.e. more tibial bone is resected.

In various embodiments, the tibial cut guide may connect to, a selected patient-specific cut alignment tool 5801, which may be applied to one or both articular sides, instead of, or in addition to, the femoral balancing template 5101. For example, a tibial cut guide may include, without limitation, a dovetail feature or other linkage or joint that slides into the patient-specific cut alignment tool 5801. Other interface/connector means known in the art may be used, such as, without limitation, a snap-fit, joints, and/or cross-pins. Any linkage known in the art may be utilized. Some of these joints or linkages may allow for movement or adjustment in one or more directions. The connection between the patient-specific cut alignment tool 5801 and a tibial cut guide may be made at a set distance from, for example, the top of each of the patient-specific cut alignment tools 5801. Subsequently, the thicker the patient-specific cut alignment tool 5801, the less bone is resected off the tibia. The tibial cutting guide may be used to make either or both the horizontal and vertical cuts on the tibial plateau. Thus, the patient specific alignment tool is used to not only determine the location and orientation of the vertical cut, but also the location and height of the horizontal cut. The thickness of the selected patient-specific cut alignment tool 5801, combined with the set position of the connected tibial cut guide relative to the patient-specific cut alignment tool 5801, correctly positions the horizontal cut on the tibia with regard to ligament balancing or ligament tension or soft-tissue tension, taking into account the thickness of the femoral and/or tibial implants to be inserted.

In illustrative embodiments, the interface between the patient-specific cut alignment tool 5801 and the tibial cut guide may impart a desired slope on the cut guide. For example, the top surface of the patient-specific cut alignment tool 5801 to which the tibial cut guide may dovetail into, may be sloped (with the slope determined via patient specific information), such that, without limitation, the tibial surface is resected perpendicular to the long axis of the tibia in the coronal plane, but sloped posteriorly in the sagittal plane to match the normal slope of the tibia. The slope may be imposed by the patient specific cut alignment tool 5801, with the slope transferred into the cut guide via a linkage. The slope may also be set in the tibial cut guide based on patient specific information included in and/or derived from the patient specific cut alignment tool 5801. For example, the slope of the tibial cut guide may be adjustable based on the configuration or other information associated with the patient specific cut alignment tool 5801. The patient specific information can be derived from a preoperative scan or an intraoperative measurement. It will typically be the slope that the patient's tibia showed on the preoperative scan. The scan may be of the same joint or a contra lateral healthy joint. An offset or a threshold may be applied. For example, if the anteroposterior slope in a patient exceeds 7 mm, the maximum allowable value of slope determined by the patient specific alignment tool may be set at 7 mm, i.e. the selected maximum. The maximum can optionally be derived as a function of the measured slope in that patient. If a patient has a preoperative tibial slope of less than 7 degrees, e.g. 4 degrees, the tibial slope in the patient specific alignment tool may be set at a number corresponding to the measured slope, i.e. in this example 4 degrees. Thus, the patient specific alignment tool may not only yield a reference for the orientation of the vertical cut and optionally horizontal cuts of a tibia, but also on the anteroposterior slope desirable in a patient. If a patient has a preoperative tibial slope of greater than 7 degrees, 7 degrees may be set as the maximum and the horizontal tibial cut may be made at a slope of 7 degrees. Other thresholds may be used, e.g. 6 degrees, 8 degrees, etc.

All of the embodiments pertaining to the balancing chip and all other embodiments may be applied to partial knee systems, e.g. medial or lateral unicompartmental tibiofemoral implants, as well as to total knee arthroplasty systems.

The embodiments may be used in the context of a femur first technique, i.e. the femur is prepared prior to preparing the tibia, or a tibia first technique, i.e. the tibia is prepared prior to preparing the femur, or combinations thereof. For example, the alignment tool 5801 may be used initially to balance the joint and to place a horizontal tibial cut, while then moving to the femoral preparation, and finishing the tibia at the end.

All of the embodiments pertaining to the balancing chip and all other embodiments may be applied to a knee joint, but also any other joint in the body. The terms "femur" or "femoral" and "tibia" and "tibial" are strictly illustrative and can also represent other bone or joint geometries. For example, the embodiments and the navigation chip can be applied in a hip (in which case the terms "tibia" and "tibial" can be replaced with "acetabulum" and "acetabular", and "femur" and "femoral" can be replaced with "femoral head" and "femoral"). The embodiments may be applied in a shoulder (in which case the terms "tibia" and "tibial" can be replaced with "glenoid" and "glenoid", and "femur" and "femoral" can be replaced with "humeral head" and "humeral"). The same analogies apply to other joints including the elbow, wrist, ankle, foot and hand.

All of the embodiments pertaining to the balancing chip and all other embodiments may be applied to hemiarthroplasty.

All of the embodiments pertaining to the balancing chip and all other embodiments may be used in combination with surgical navigation or robotic surgery. For example, radiofrequency and optical markers may be used for planning femoral and tibial bone cuts, while a balancing chip as described above may be used for ligament balancing or soft-tissue or ligament tensioning. The markers may optionally be connected, directly or via a linkage, to the balancing chip. Moreover, in another example, a robot may be used for planning or directing tibial or femoral bone cuts, while a balancing chip as described above may be used for ligament balancing or soft-tissue or ligament tensioning. The robot may optionally be connected, directly or via a linkage, to the balancing chip or to any other patient specific alignment tool.

Figure 16:
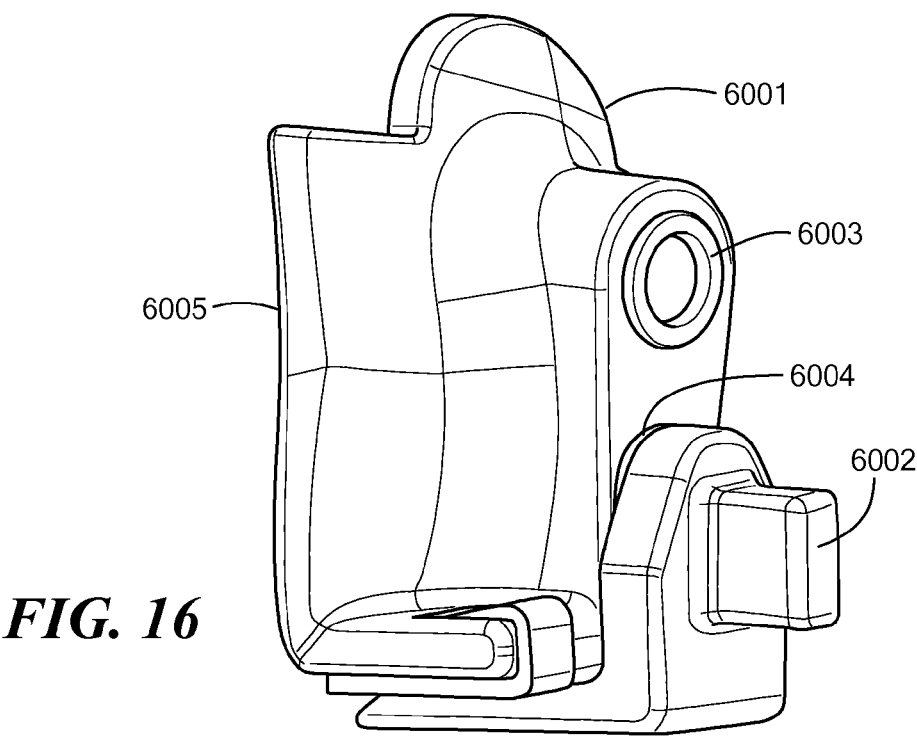
FIGS. 16-23 illustrate the procedure and tools for installing the femoral implant
Figure 17:
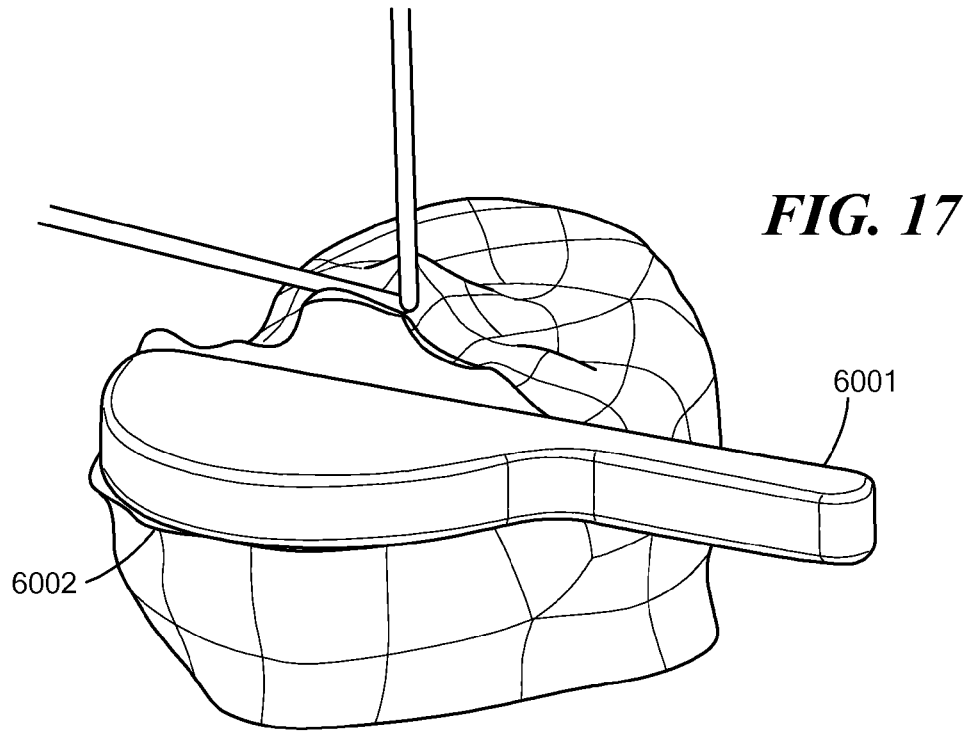
Figure 18:
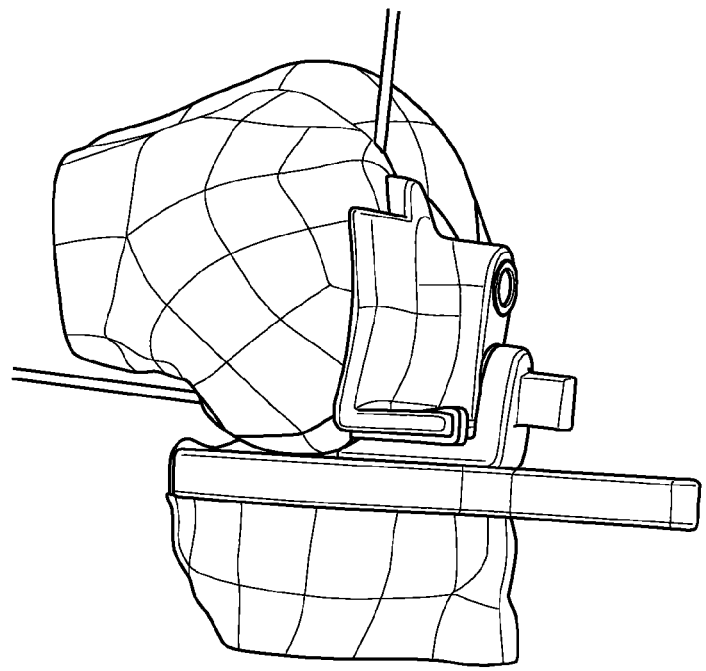
Figure 19:
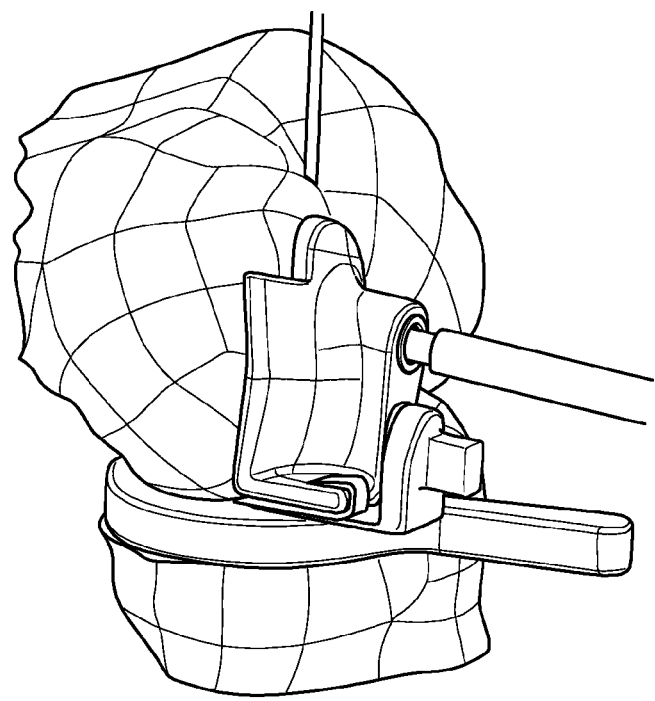
Figure 20:
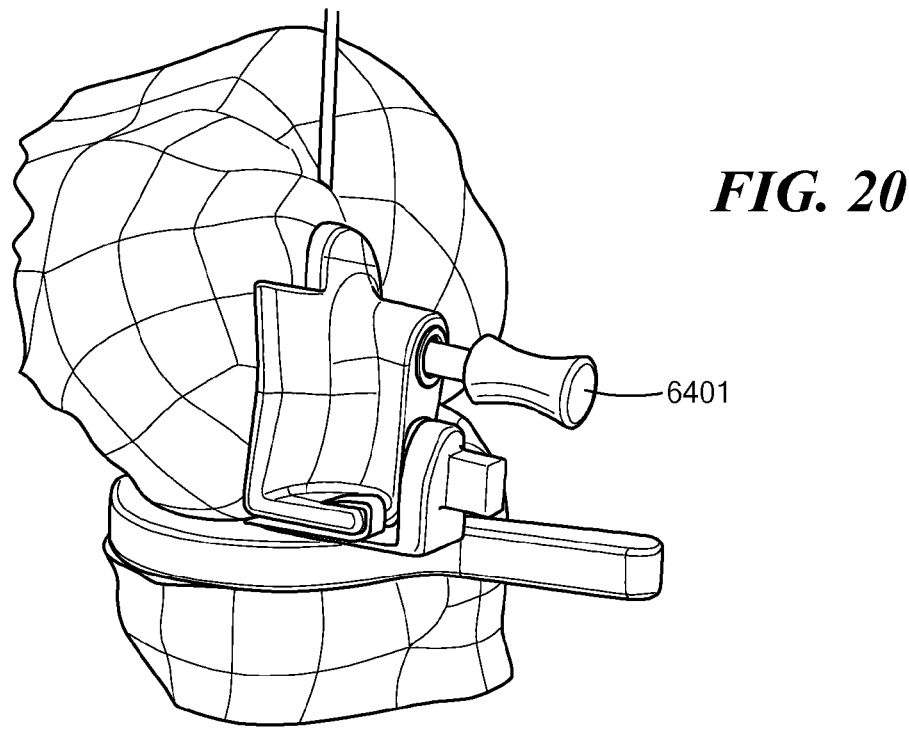
Figure 21:
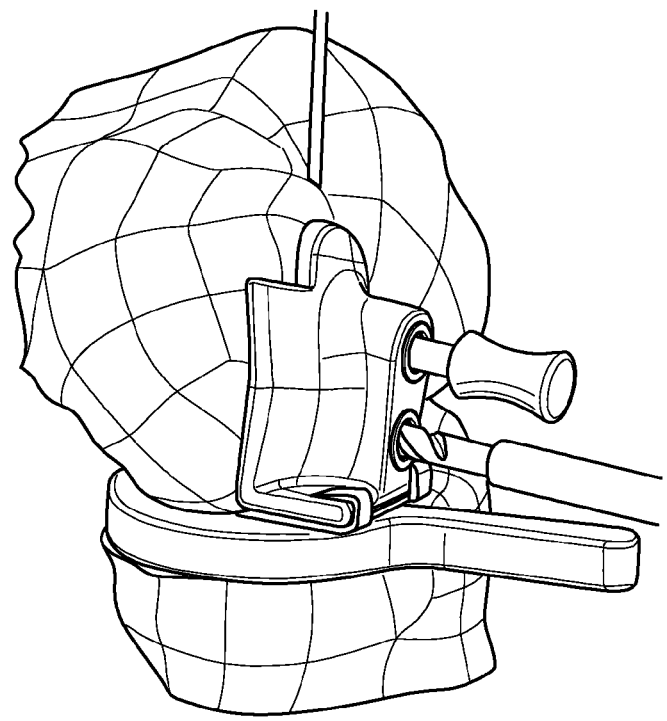
Figure 22:
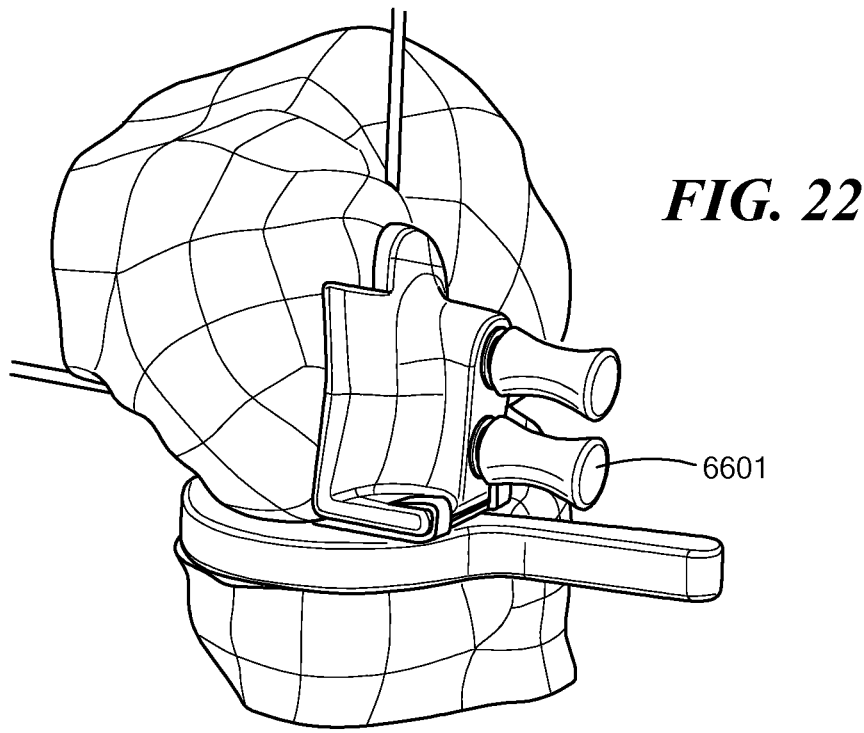
Figure 23:
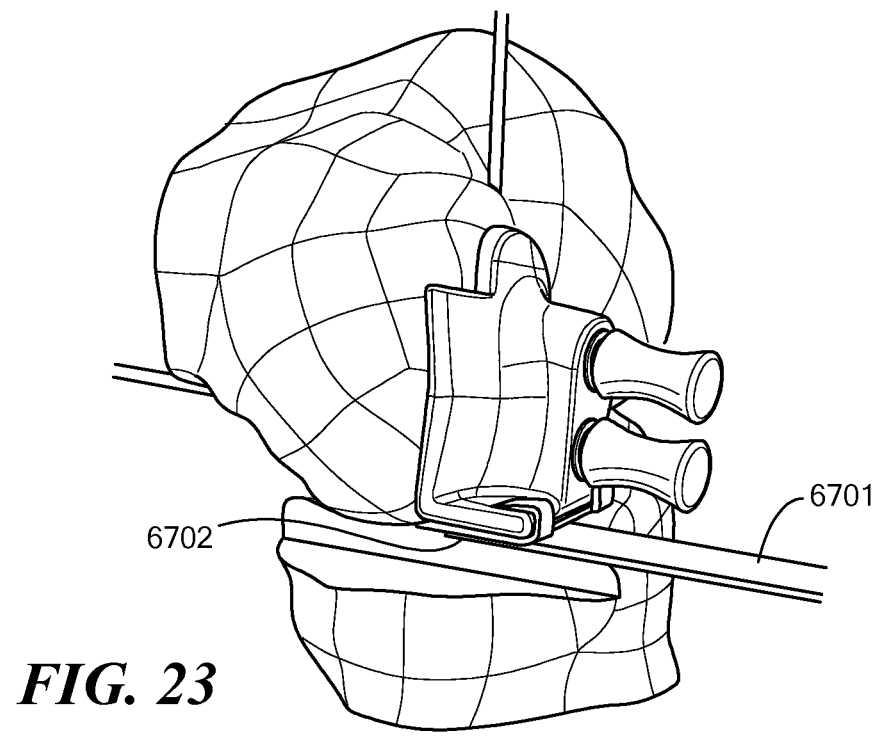
Figure 24:
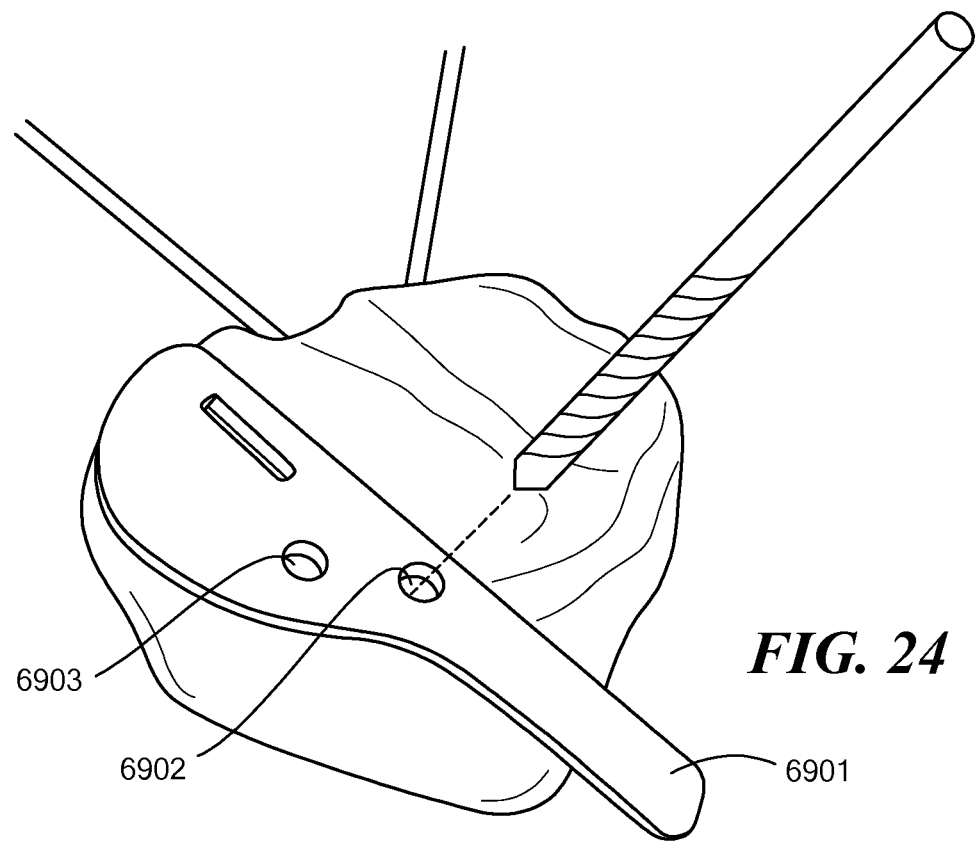
FIG. 24 shows the femoral guide removed, and a trough for the anterior margin of the femoral implant, in accordance with an embodiment of the invention.
Figure 25:
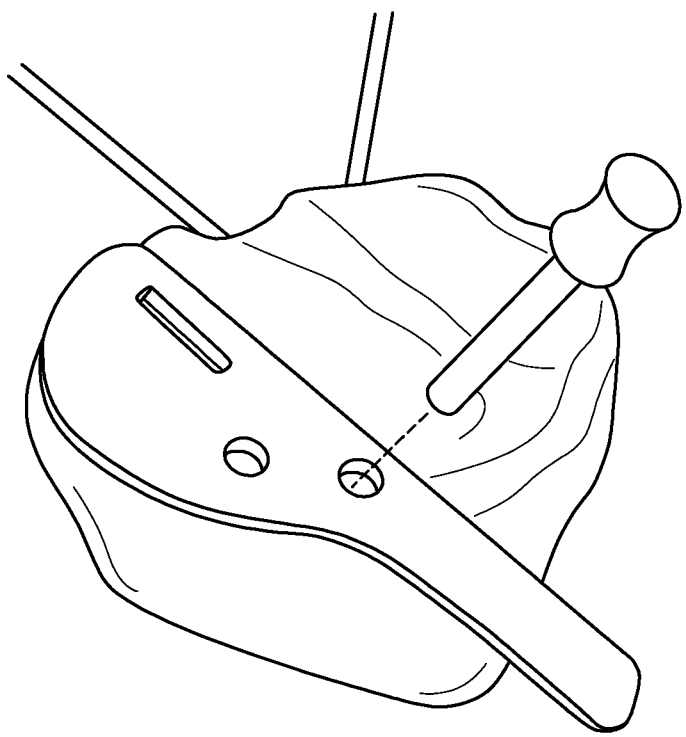
FIGS. 25-28 illustrate a procedure and tools for installing the tibial implant, in accordance with an embodiment.

FIGS. 16-23 illustrate the procedure and tools for installing the femoral implant of this embodiment. FIG. 16 illustrates femoral guide 6001 and removable L guide 6002 which has a short pin which fits into lower pin hole 6004, and around which L guide 6002 may rotate for alignment purposes. The knee is placed into flexion. Guides 6001 and 6002 are assembled, and patient-specific surface 6005 is mated to the femoral surface. Spacer block 6010, which has a patient-specific outer edge, i.e., the horizontal geometry replicates the area of the cut tibial plateau, is placed onto the cut tibial surface 6002. Spacer block 6010 may be provided in a number of thicknesses to ensure proper spacing with the knee in flexion. L guide 6002 is adjusted to sit flat on spacer block with knee in flexion (FIG. 18), adjusting the flexion angle if necessary to facilitate this. A drill hole in the femur is made through pin hole 6003 (FIG. 19), and a pin 6401 is inserted to fix guide 6001 to the femur (FIG. 20). L guide 6002 is removed, and a drill hole in the femur is made through pin hole 6004 (FIG. 21), and a pin 6601 is inserted in pin hole 6004 of guide 6001 (FIG. 22).

With the femoral guide 6001 thus pinned to the femur, a posterior femoral cut in preparation for receiving a femoral implant is made; oscillating saw blade 6701 is moved against horizontal cutting guide 6702 to remove bone in the posterior portion of the condyle (FIG. 22.) The femoral guide 6001 is removed, and a trough for the anterior margin of the femoral implant is made.

Figure 28:
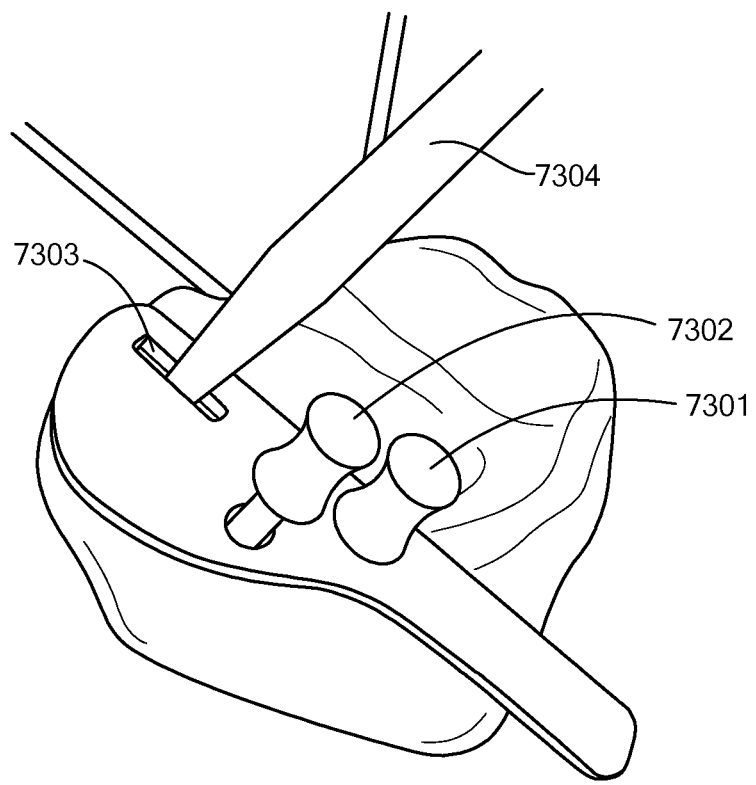

FIGS. 24-27 illustrate a procedure and tools for installing the tibial implant of this embodiment, wherein patient-specific template 6901, having drill holes 6902 and 6903 is placed in the cut tibial area, holes are drilled, and pins 7302 and 7301 are inserted to fix the template in place. In FIG. 28, a fin is created using an osteotome (e.g., about 5 mm in width), using guide slot 7303. Template 6901 can then be removed to widen and finish the fin hole preparation. The implants may now be installed.

In illustrative embodiments, three-dimensional guidance templates may be utilized to determine an optimized implant rotation. Examples are provided below with reference to the knee, however it is to be understood that optimizing implant rotation may be applied to other joints as well.

Femoral Rotation:

The optimal rotation of a femoral component or femoral implant for a uni-compartmental, patello femoral replacement or total knee replacement may be ascertained in a number of different ways. Implant rotation is typically defined using various anatomic axes or planes. These anatomic axes may include, without limitation, the transepicondylar axis; the Whiteside line, i.e. the trochlea anteroposterior axis, which is typically perpendicular to at least one of the cuts; and/or the posterior condylar axis. Other axes include but are not limited to Blumensaat's line, femoral shaft axis, femoral neck axis, acetabular angle, lines tangent to the superior and inferior acetabular margin, lines tangent to the anterior or posterior acetabular margin, femoral shaft axis, tibial shaft axis, transmalleolar axis, posterior condylar line, tangent(s) to the trochlea of the knee joint, tangents to the medial or lateral patellar facet, lines tangent or perpendicular to the medial and lateral posterior condyles, lines tangent or perpendicular to central weight-bearing zone of the medial and lateral femoral condyles, lines transsecting the medial and lateral posterior condyles, for example through their respective centerpoints, lines tangent or perpendicular to the tibial tuberosity, lines vertical or at an angle to any of said lines, lines tangent to or intersecting the cortical bone of any bone adjacent to or enclosed in a joint.

Another approach for optimizing femoral component rotation is a so-called balancing gap technique. With the balancing gap technique, a femoral cut is made parallel to the tibia, i.e. the tibia is cut first typically. Prior to performing the femoral cut, the femoral cut plate is optimized so that the medial and lateral ligament and soft tissue tension are approximately equal.

By measuring the relevant anatomic axis or planes, the optimal implant rotation may be determined. The measurement may be factored into the shape, position or orientation of the 3D guidance template, in accordance with an embodiment of the invention. Any resultant surgical interventions including cuts, drilling, or sawings are then made incorporating this measurement, thereby achieving an optimal femoral component rotation.

Moreover in order to achieve an optimal balancing, the rotation of the template may be changed so that the cuts are parallel to the tibial cut with substantially equal tension medially and laterally applied.

Tibial Rotation:

A 3D guidance template may also be utilized to optimize tibial component rotation for uni-compartmental or total knee replacements, in accordance with an embodiment of the invention. Tibial component rotation may be measured using a number of different approaches known in the art. In one example of a tibial component rotation measurement, the anteroposterior axis of the tibia is determined. For a total knee replacement, the tibial component can be placed so that the axis of the implant coincides with the medial one-third of the tibial tuberosity. This approach can work well when the tibia is symmetrical.

In another embodiment, the symmetrical tibial component is placed as far as possible posterolateral and externally rotated so that the posteromedial corner of the tibial plateau is uncovered to an extent of between three (3) and five (5) millimeters.

The above examples are only representative of the different approaches that have been developed in the literature. Clearly, other various anatomic, biomechanical axis, plane and area measurements may be performed in order to optimize implant rotation.

In illustrative embodiments, these measurements may be factored into the design of a 3D guidance template and the position, shape or orientation of the 3D guidance template may be optimized utilizing this information. Thus, any subsequent surgical intervention such as cutting, sawing and/or drilling will result in an optimized implant rotation, for example, in the horizontal or in a near horizontal plane.

Example 1 below is included to more fully illustrate the present invention. Additionally, this example provides a single embodiment of the invention and is not meant to limit the scope thereof.

Example 1

Unicompartmental Knee Resurfacing Using Patient-Specific Implants and Instrumentation An exemplary surgical technique for use in implanting a novel partial knee resurfacing UKA using customized, single-use instrumentation is described below, in accordance with one embodiment of the invention.

CT scans of a patient's knee and partial scans of the hip and ankle are utilized to create patient-specific implants and instrumentation. Based on the CT images, the knee anatomy is digitally recreated, the surface topography of the femur and tibia are mapped, and axis deformity is corrected. The same data is used to create cutting and placement guides that are pre-sized and pre-navigated to work with the patient's anatomy and custom implants.

Figure 31:
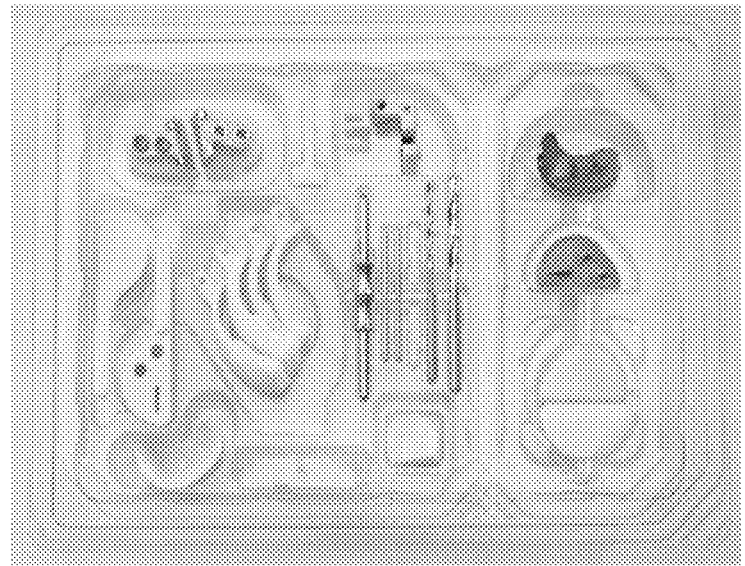
FIG. 31 shows the femoral balancing template removed, the patient specific alignment tool positioned on the tibial plateau, and a cutting guide attached to the tibia, in accordance with one embodiment of the invention.

A kit may be provided with the resurfacing implants and disposable instrumentation in a single sterile tray, as shown in FIG. 31, in accordance with one embodiment of the invention. The various instruments in the kit may be patient-specific instruments or non-patient specific instruments, for example, standardized tools, templates and other devices that may be used during the course of the surgery and in conjunction with other patient-specific instruments and other devices.

The surgical technique may illustratively include the following steps, described in more detail below: patient positioning and preparation; balancing of the knee; axial & sagittal tibial cuts; femoral preparation; balancing verification & tibial preparation; and trialing & cementing of implant.

Patient Positioning and Preparation

The patient is positioned supine on the table with the leg resting on a foot support around 90 degrees flexion. After a standard short midline skin incision, a medial or lateral parapatellar arthrotomy is performed. The medial (or lateral) sleeve is not released, but typically all femoral and tibial osteophytes, including those in the intercondylar notch are removed.

In extension the sulcus terminalis is marked with a marking pen, where the anterior tibial lip hits the femoral condyle. The femoral cutting block, which is shaped to substantially fit the condyle and represents the size and geometry of the femoral implant is placed on the femoral condyle. Typically, the anterior edge of the femoral cutting block seats about 2-3 mm inferior to the Sulcus terminalis. The round anterior silhouette of the femoral cutting block is marked on the femoral condyle.

Figure 32:
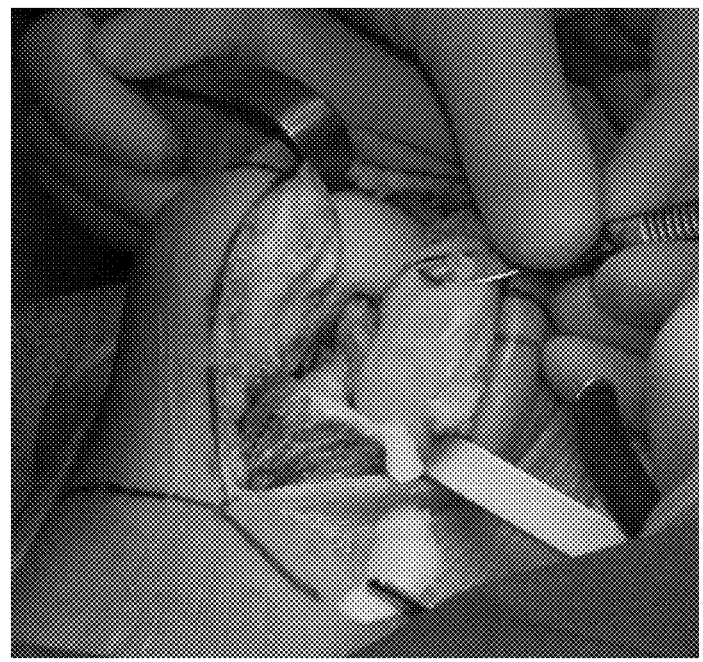
FIG. 32 shows a kit that may be provided with the resurfacing implants and disposable instrumentation in a single sterile tray, in accordance with one embodiment of the invention.
Figure 33:
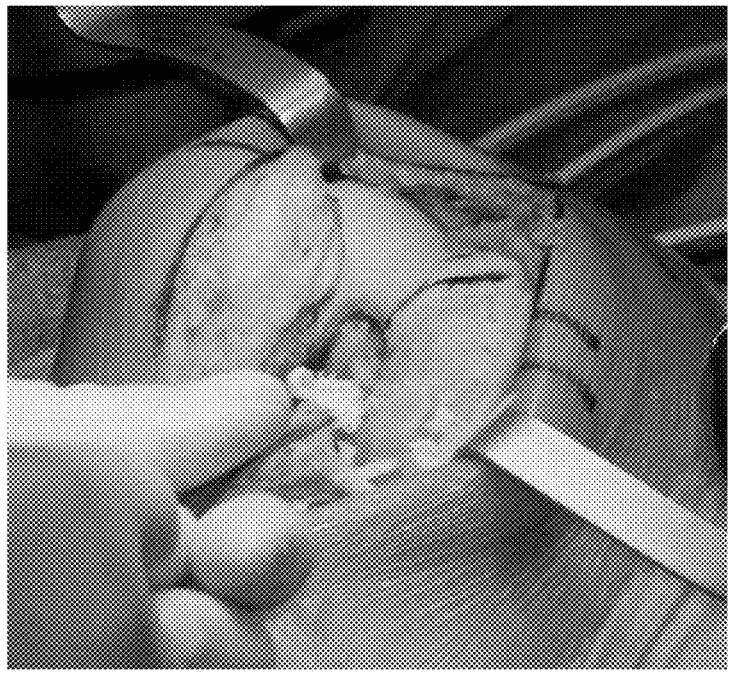
FIG. 33 shows cartilage removal on the condyle, in accordance with one embodiment of the invention.

The implant is typically designed to the surface of the subchondral bone with a thickness of 3.5 mm. Since it resurfaces the bone plate, substantially all cartilage posterior to the sulcus terminalis, including the posterior condyle, is removed. This may be facilitated, for example, using a 10 millimeter blade, curved elevator, osteotome or a ring-currette, as shown in FIGS. 32 and 33, in accordance with one embodiment of the invention. That the femoral jig conforms to the condyle after cartilage removal is then confirmed.

Once removal of all residual cartilage on the femur has been concluded, residual cartilage is scraped off the tibial plateau and balancing of the knee is started.

Balancing of the Knee

Figure 34:
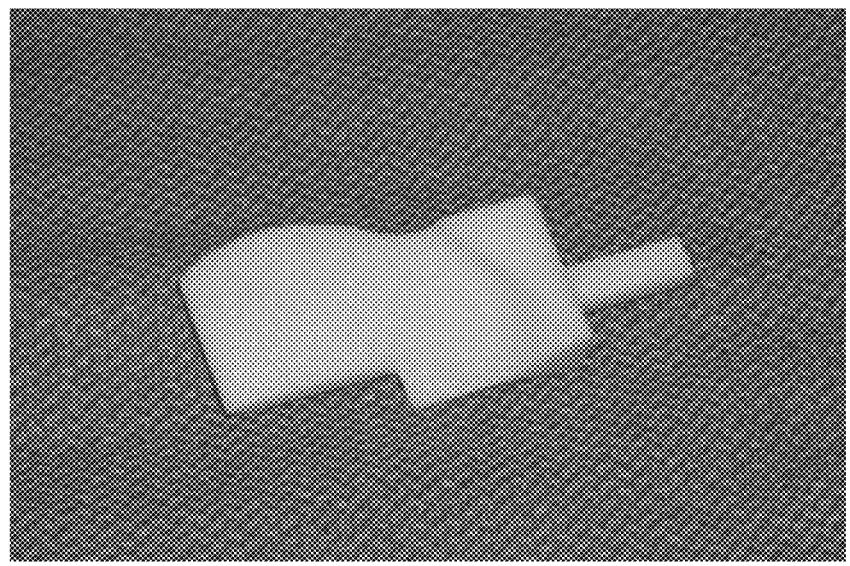
FIG. 34 shows cartilage removal on the condyle, in accordance with one embodiment of the invention.

Four navigation "chips" of varying thicknesses in 1 mm increasing increments are included in the instrument tray. Each chip has an underside that substantially matches the shape and topography of the patient's tibial surface. When inserted into the compartment, the chip will self-seat into a stable position due to its conformity with the anatomic landmarks on the tibia. The top surface of this chip is flat to allow referencing off the distal femor condylar surface during balancing. FIG. 34 shows an exemplary navigation chip, in accordance with one embodiment of the invention.

Figure 35:
FIG. 35 shows an exemplary navigation chip, in accordance with one embodiment of the invention.

Each chip may be inserted in turn, from thinnest to thickest, with the knee in flexion and then taken through the desired range of motion. A chip is then selected that provides the desired ligament tensioning. FIG. 35 shows a navigation chip in-situ, in accordance with one embodiment of the invention.

Illustratively, an opening under valgus stress of about 1 mm is recommended medially in extension and 90 degrees flexion and about 1-3 mm under varus stress laterally in extension and about 3-5 mm in 90 degrees flexion. The thicker the chip, the less bone is resected off the tibia.

Axial & Sagittal Tibial Cuts

Figure 36:
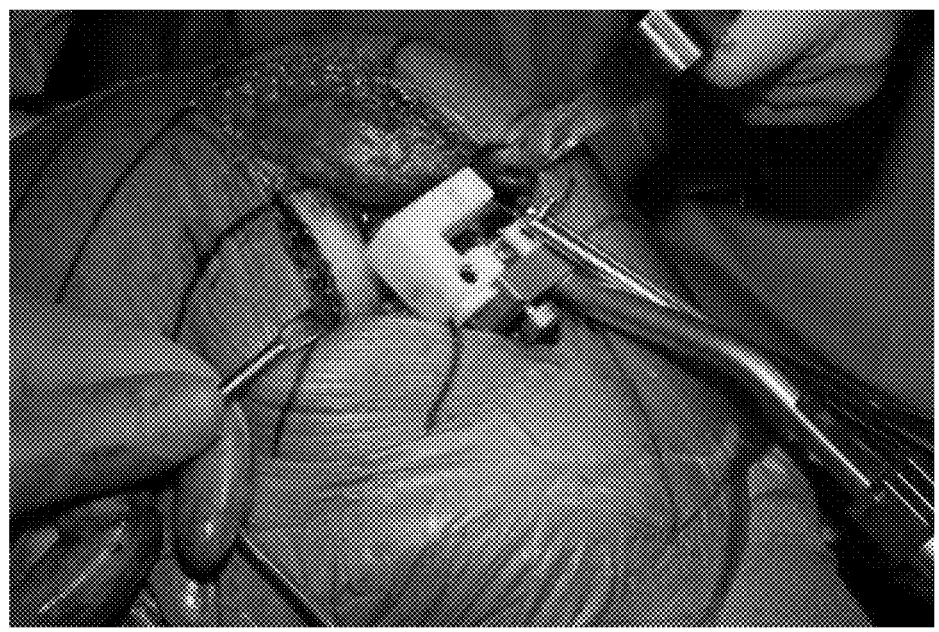
FIG. 36 shows a navigation chip in-situ, in accordance with one embodiment of the invention.

The selected navigation chip connects to a tibial cutting block (also referred herein as the tibial jig). The tibial jig may also optionally connect to an extramedullary alignment guide. The alignment guide may be placed on the leg and the tibial jig is attached to the navigation chip to establish its placement. The tibial jig may then be pinned flush to the anterior tibia. FIG. 36 shows the tibial jig placed in the knee, in accordance with one embodiment of the invention.

Figure 37:
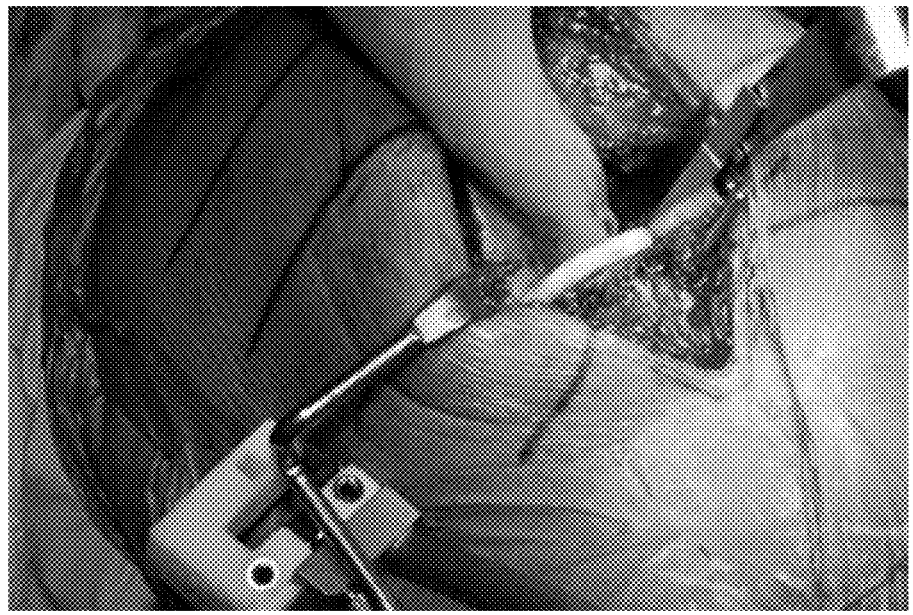
FIG. 37 shows the tibial jig placed in the knee, in accordance with one embodiment of the invention.

The tibial cut planes are confirmed with the navigation chip, as shown in FIG. 37, in accordance with one embodiment of the invention: the sagittal cut, the axial cut—90 degrees relative to the tibial mechanical axis—and the posterior slope. The tibial cutting block may be repositioned if necessary, whereupon the tibial cutting block is pinned in place.

The sagittal tibial cut is performed using the tibial cutting block. The reciprocating saw blade may be left in as shown in FIG. 34 to protect the ACL while performing the axial cut. The axial tibial cut is performed referencing off the tibial jig.

Figure 38:
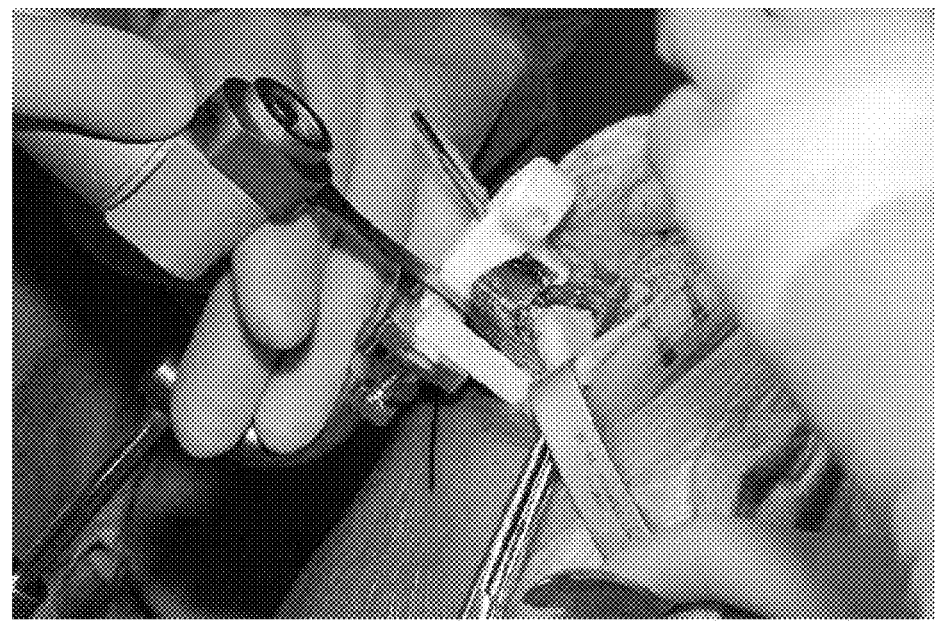
FIG. 38 shows confirmation of the tibial cut planes, in accordance with one embodiment of the invention.

FIG. 38 shows the tibial axial cut, in accordance with one embodiment of the invention. The Alignment Guide and the Tibial Jig may then be removed.

Femoral Preparation

Figure 39:
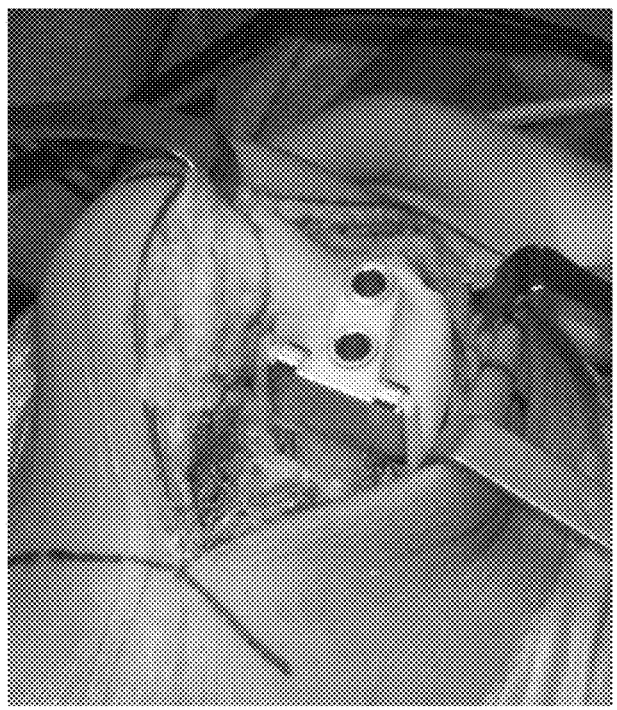
FIG. 39 shows the tibial axial cut, in accordance with one embodiment of the invention.

The femoral jig is placed on the distal femur and its position is verified. The femoral jig is designed to conform to the femur in only one location so as to aid in proper positioning. FIG. 39 shows the femoral jig placed on the distal femur, in accordance with one embodiment of the invention. Any additional cartilage or osteophytes that were missed previously are removed until the fit is snug and secure. Illustratively, the peg-holes may be drilled in 15 degrees flexion relative to the sagittal anatomical femoral axis and the amount to be removed off the posterior condyle may be 3-5 mm.

Figure 40:
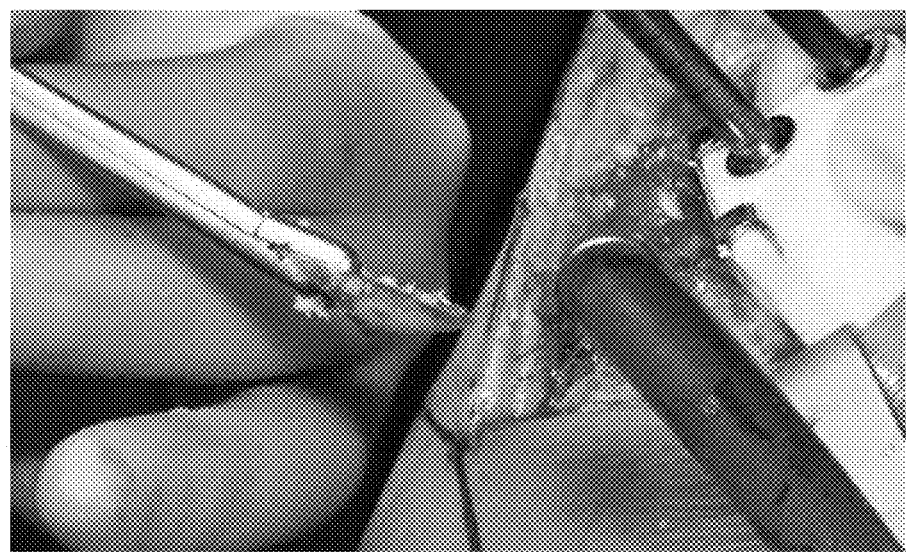
FIG. 40 shows the femoral jig placed on the distal femur, in accordance with one embodiment of the invention.

The femoral jig is then drilled and pinned in place and the posterior femoral cut is performed, as shown in FIG. 40 in accordance with one embodiment of the invention. In various embodiments, this is the only bone resection required on the femur.

To complete femoral preparation, an anterior recess may be prepared using a curved osteotome or a 5 mm burr. Illustratively, the most anterior edge of the component submerges 3.5 mm below the subchondral bone plate. The taper starts 10 mm inferior to it. Also the transition from the subchondral bone to the anterior edge of the posterior cut may be rounded, using either a file, burr or osteotome. Smoothening of the edge and placement and depth of recess may then be verified with a femoral trial implant.

Balancing Verification & Tibial Preparation

Figure 41:
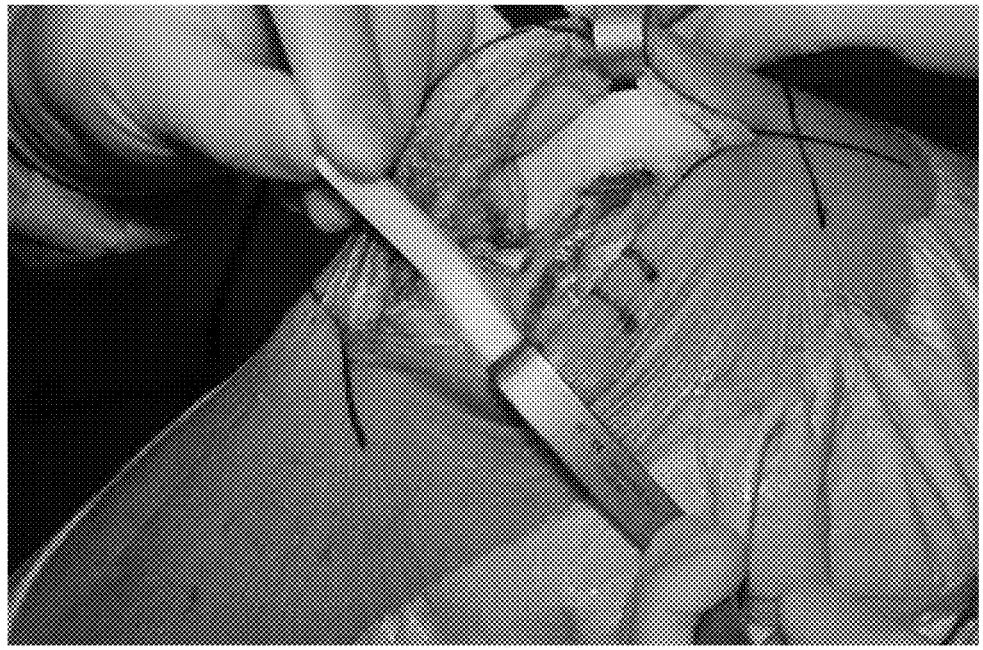
FIG. 41 shows the posterior femoral cut performed, in accordance with one embodiment of the invention.

With the femoral trial implant in place, a spacer block is inserted, such as an 8 mm spacer block, and balance in flexion and extension is evaluated. FIG. 41 shows flexion and extension balance verification, in accordance with one embodiment of the invention. If the knee is too tight, an additional 1 to 2 millimeters may be resected from the tibia. If too loose, the 10 millimeter spacer block may be inserted, with balance in flexion and extension reevaluated.

Figure 42:
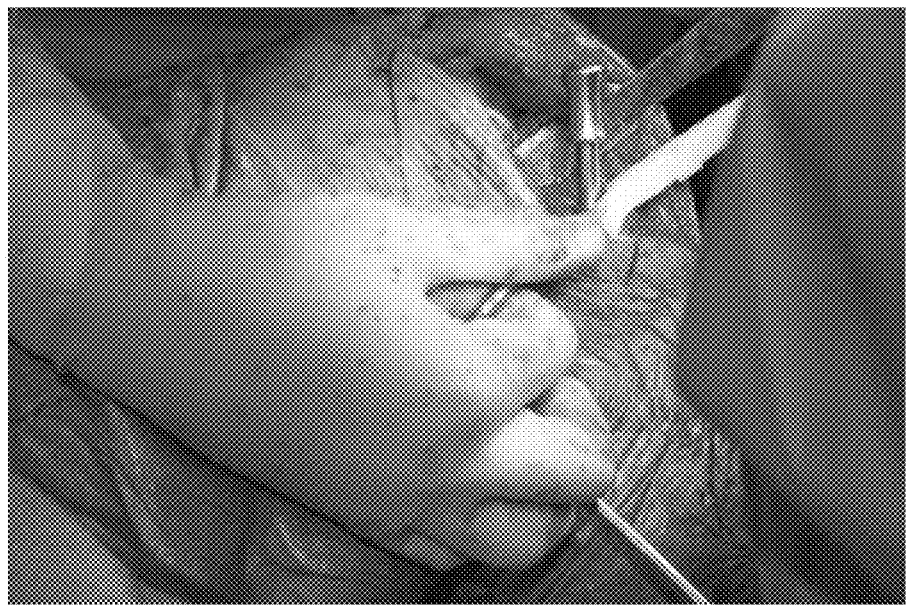
FIG. 42 shows flexion and extension balance verification, in accordance with one embodiment of the invention.

The Tibial Template is placed on the tibia and both holes are drilled, pinning the anterior hole only to accommodate instruments for the upcoming fin hole preparation. FIG. 42 shows tibial template placement, in accordance with one embodiment of the invention. Next, the fin hole is created using, for example, a 5 millimeter osteotome. The tibial implant is designed to match the patient anatomy and should cover the tibia cortex without overhang or undercoverage. The outline of the tibial template provides visual confirmation of the match.

Trialing & Cementing of Implant

Figure 43:
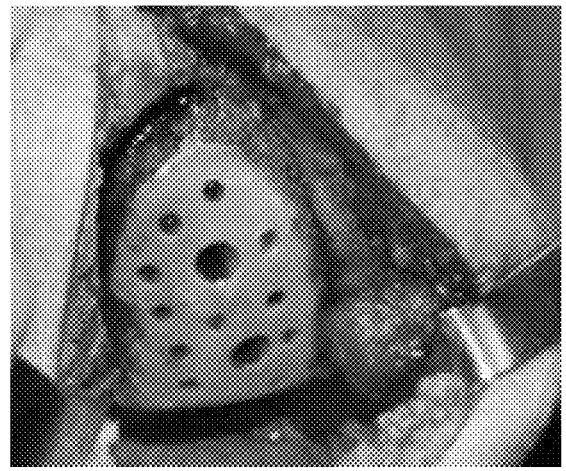
FIG. 43 shows tibial template placement, in accordance with one embodiment of the invention.

Multiple 1.5 to 2 mm cement holes may be drilled to enhance cement interdigitation with the femoral cortical surface, and the joint is thoroughly irrigated. FIG. 43 shows the femoral cement holes, in accordance with one embodiment of the invention. Next, the metal implants are placed into position and the trial poly is inserted which provides optimal balancing. Illustratively, two different thicknesses may be provided, 6 mm or 8 mm. Combined with the 2 millimeter thickness of the tibial tray, the 6 and 8 mm trials will correspond to the 8 and 10 millimeter Spacer Blocks used to confirm proper balance.

Figure 44:
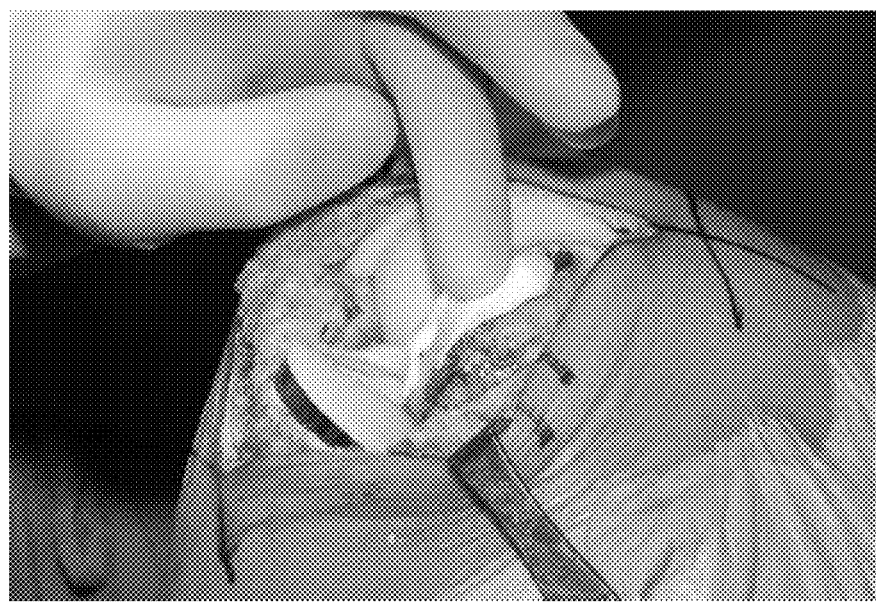
FIG. 44 shows the implants being cemented, in accordance with one embodiment of the invention.
Figure 45:
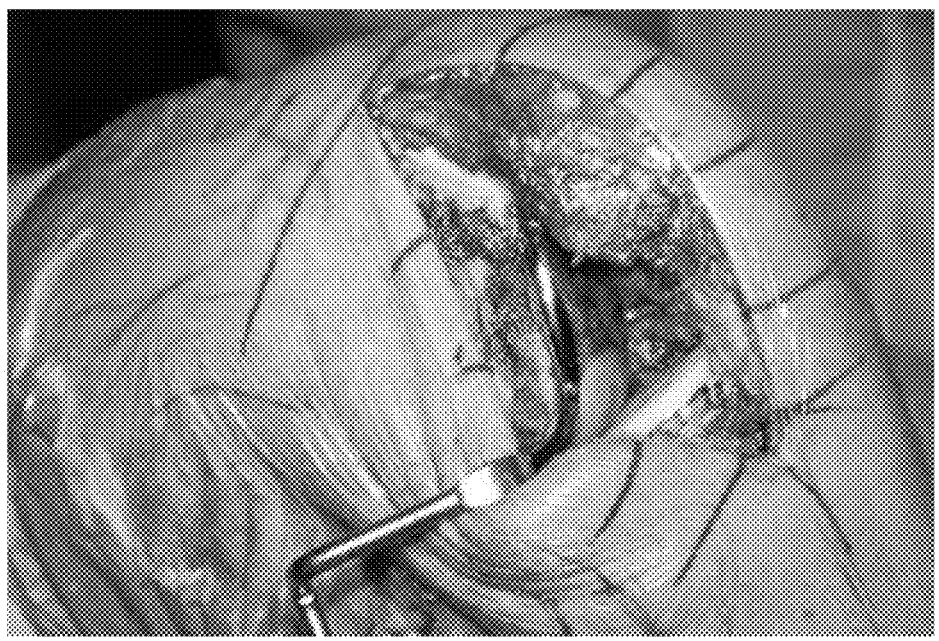
FIG. 45 shows the implants cemented in place, in accordance with one embodiment of the invention.

The tibial tray may be cemented first, with all extruded cement removed and then the femoral component may be inserted. FIG. 44 shows the implants being cemented, in accordance with one embodiment of the invention. The knee is brought in 45 degrees and the trial tibial insert is inserted, allowing equal pressurization of the femoral component in flexion and in extension. All extruded cement is removed and the cement is allowed to harden. FIG. 45 shows the implants cemented in place, in accordance with one embodiment of the invention. The trial insert is removed along with any residual extruded cement and the real polyethylene insert is inserted. Wound closure of the arthrotomy is recommended in flexion and multiple layers.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims equivalents thereof

What is claimed is:

1. A patient-specific surgical tool for use in partial replacement of a knee joint of a patient, comprising:
a block having a patient-specific surface and a guide,
at least a portion of the patient-specific surface having a shape that is substantially a negative of a corresponding surface portion of a proximal end of a tibia of the knee joint of the patient; and
the guide having a shape to accommodate a cutting or drilling tool and being oriented in a substantially vertical position relative to a tibial plateau,
wherein the guide defines a cutting or drilling path extending through at least a portion of the proximal end of the tibia in a substantially vertical plane relative to the tibial plateau.

2. The patient-specific surgical tool of claim 1, wherein the at least a portion of the patient-specific surface has a shape that is substantially a negative of a corresponding surface portion of at least one of subchondral bone, cartilage, and bone of the tibial plateau.

3. The patient-specific surgical tool of claim 1, wherein the at least a portion of the patient-specific surface has a shape that is substantially a negative of a corresponding portion of a diseased or damaged cartilage surface of the tibial plateau.

4. The patient-specific surgical tool of claim 1, wherein the at least a portion of the patient-specific surface has a shape that is substantially a negative of a corresponding anterior surface portion of the proximal end of the tibia.

5. The patient-specific surgical tool of claim 1, wherein the at least a portion of the patient-specific surface has an outer edge that substantially matches with a corresponding portion of the outer periphery of the tibial plateau.

6. The patient-specific surgical tool of claim 1, wherein the guide is configured to include a stop that defines a desired end of the cutting or drilling path.

7. The patient-specific surgical tool of claim 1, further including a second guide configured to accommodate a cutting or drilling tool and being oriented at a predetermined slope relative to the tibial plateau, wherein the second guide defines a cutting or drilling path extending through at least a portion of the proximal end of the tibia in a substantially horizontal plane at a predetermined slope relative to the tibial plateau.

8. The patient-specific surgical tool of claim 7, wherein the predetermined slope is configured based on patient-specific information.

9. The patient-specific surgical tool of claim 8, wherein the patient-specific information includes information derived from a preoperative scan or an intraoperative measurement.

10. The patient-specific surgical tool of claim 1, further including a linkage configured to cross reference a femoral surgical tool configured to prepare a femur of the knee joint of the patient.

11. The patient-specific surgical tool of claim 10, wherein the linkage is configured to cross reference a guide of the femoral surgical tool configured to direct a cutting or drilling tool for preparing the femur of the knee joint of the patient.

12. The patient-specific surgical tool of claim 11, wherein the linkage is configured to cross reference at least a portion of the prepared femur of the knee joint of the patient.

13. The patient-specific surgical tool of claim 10, wherein the linkage is configured to cross reference a sample implant configured for the femur of the knee joint of the patient.

14. The patient-specific surgical tool of claim 10, wherein the linkage includes an attachment.

15. The patient-specific surgical tool of claim 1, wherein the substantially vertical plane relative to the tibial plateau is configured to match a medial edge of a tibial component for the partial replacement of the knee joint of the patient.

16. The patient-specific surgical tool of claim 1, wherein the surgical tool is configured to include patient-specific information that defines optimal implant rotation.

17. The patient-specific surgical tool of claim 1, wherein the patient-specific surface includes joint information derived from image data of the knee joint of the patient.

18. The patient-specific surgical tool of claim 17, wherein the joint information includes cartilage information.

19. A patient-specific surgical tool for use in partial replacement of a knee joint of a patient, comprising:
   a block having a patient-specific surface and a guide,
      at least a portion of the patient-specific surface including joint information derived from image data of a proximal end of a tibia of the knee joint of the patient; and
      the guide having a shape to accommodate a cutting or drilling tool and being oriented in a generally vertical position relative to a tibial plateau,
      wherein the guide defines a cutting or drilling path extending through at least a portion of the proximal end of the tibia in a generally vertical plane relative to the tibial plateau.

20. The patient-specific surgical tool of claim 19, wherein the guide is orientated in a substantially vertical position relative to the tibial plateau and defines a cutting or drilling path extending through at least a portion of the proximal end of the tibia in a substantially vertical plane relative to the tibial plateau.

21. The patient-specific surgical tool of claim 19, wherein the at least a portion of the patient-specific surface has a shape that is substantially a negative of a corresponding surface portion of at least one of subchondral bone, cartilage, and bone of the tibial plateau.

22. The patient-specific surgical tool of claim 19, wherein the at least a portion of the patient-specific surface has a shape that is substantially a negative of a corresponding portion of a diseased or damaged cartilage surface of the tibial plateau.

23. The patient-specific surgical tool of claim 19, wherein the at least a portion of the patient-specific surface has a shape that is substantially a negative of a corresponding anterior surface portion of the proximal end of the tibia.

24. The patient-specific surgical tool of claim 1, wherein the at least a portion of the patient-specific surface has an outer edge that substantially matches with a corresponding portion of the outer periphery of the tibial plateau.

25. The patient-specific surgical tool of claim 19, wherein a portion of the patient-specific surface has a shape that is substantially a negative of a corresponding surface portion of a proximal end of the tibia of the knee joint of the patient.

26. A patient-specific surgical tool for use in partial replacement of a knee joint of a patient, comprising:
   a block having a patient-specific surface and a guide;
      at least a portion of the patient-specific surface including information derived from image data of a diseased or damaged cartilage surface of a tibial plateau of a tibia of the knee joint of the patient; and
      the guide having a shape to accommodate a cutting or drilling tool and being oriented in a substantially vertical position,
      wherein the guide defines a cutting or drilling path extending through at least a portion of the proximal end of the tibia in a substantially vertical plane.

27. The patient-specific surgical tool of claim 26, wherein the at least a portion of the patient-specific surface has a shape that is substantially a negative of a corresponding anterior surface portion of the proximal end of the tibia.

28. The patient-specific surgical tool of claim 26, wherein the at least a portion of the patient-specific surface has an outer edge that substantially matches with a corresponding portion of the outer periphery of the tibial plateau.

29. The patient-specific surgical tool of claim 26, wherein a portion of the patient-specific surface has a shape that is substantially a negative of a corresponding portion of the diseased or damaged cartilage surface of the tibial plateau.

\* \* \* \* \*